(12) United States Patent
Sauvageau et al.

(10) Patent No.: US 10,273,503 B2
(45) Date of Patent: Apr. 30, 2019

(54) COMPOUNDS AND METHODS FOR ENHANCING VIRAL GENE TRANSFER TO HUMAN HEMATOPOIETIC CELLS

(71) Applicants: UNIVERSTÉ DE MONTRÉAL, Montréal, Québec (CA); BRITISH COLUMBIA CANCER AGENCY BRANCH, Vancouver, British Columbia (CA); FRED HUTCHINSON CANCER RESEARCH CENTER, Seattle, WA (US)

(72) Inventors: Guy Sauvageau, Montréal (CA); Keith Richard Humphries, Vancouver (CA); Hans-Peter Kiem, Seattle, WA (US); Iman Fares, Montréal (CA); Jalila Chagraoui, Montréal (CA)

(73) Assignees: UNIVERSITE DE MONTREAL, Montreal, Quebec (CA); BRITISH COLUMBIA CANCER AGENCY BRANCH, Vancouver, British Columbia (CA); FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 15/512,361

(22) PCT Filed: Sep. 17, 2015

(86) PCT No.: PCT/CA2015/050907
§ 371 (c)(1),
(2) Date: Mar. 17, 2017

(87) PCT Pub. No.: WO2016/041080
PCT Pub. Date: Mar. 24, 2016

(65) Prior Publication Data
US 2018/0201953 A1    Jul. 19, 2018

(51) Int. Cl.
| | | |
|---|---|---|
| *C12N 15/86* | (2006.01) |
| *C12N 5/0789* | (2010.01) |
| *C12N 15/87* | (2006.01) |
| *A61K 48/00* | (2006.01) |
| *A61K 35/28* | (2015.01) |
| *C07D 487/04* | (2006.01) |
| *C07D 519/00* | (2006.01) |
| *C07K 5/083* | (2006.01) |

(52) U.S. Cl.
CPC .............. *C12N 15/86* (2013.01); *A61K 35/28* (2013.01); *A61K 48/00* (2013.01); *C07D 487/04* (2013.01); *C07D 519/00* (2013.01); *C07K 5/0806* (2013.01); *C12N 5/0647* (2013.01); *C12N 15/87* (2013.01); *C12N 2501/999* (2013.01); *C12N 2510/00* (2013.01); *C12N 2740/15043* (2013.01)

(58) Field of Classification Search
CPC ...... C12N 15/87; C12N 15/86; C12N 15/867; C12N 5/0789; A61K 35/12; A61K 35/28; A61K 48/00; C07K 5/10; C07K 5/083; C07D 487/04
See application file for complete search history.

(56) References Cited

U.S. PATENT DOCUMENTS

| | | | |
|---|---|---|---|
| 5,686,278 A | * | 11/1997 | Williams ........... A01K 67/0271 435/372 |
| 5,994,136 A | | 11/1999 | Naldini et al. |
| 6,013,516 A | | 1/2000 | Verma et al. |
| 2003/0044978 A1 | | 3/2003 | Young et al. |
| 2015/0011543 A1 | | 1/2015 | Sauvageau et al. |

FOREIGN PATENT DOCUMENTS

| | | |
|---|---|---|
| WO | WO 99/40180 A2 | 8/1999 |
| WO | WO 2007/145227 A1 | 12/2007 |
| WO | WO 2013/110198 A1 | 8/2013 |
| WO | WO 2014/026110 A2 | 2/2014 |
| WO | 2015/161373 A1 | 10/2015 |

OTHER PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*
Banker, Gilbert S. et al., Modem Pharmaceutics, Marcel Dekker, New York, 1996. (Year: 1996).*
International Search Report (PCT/ISA/210) dated Nov. 30, 2015, by the Canadian Patent Office as the International Searching Authority for International Application No. PCT/CA2015/050907.
Di Nunzio F. et al,"Transduction of Human Hematopoietic Stem Cells by Lentiviral Vectors Pseudotyped with the RD114-TR Chimeric Envelope Glycoprotein" Human Gene Therapy, vol. 18, No. 9, pp. 811-820, Sep. 2007.
Aiuti A. et al.,"Lentivirus-based Gene Therapy of Hematopoietic Stem Cells in Wiskott-Aldrich Syndrome" Science, vol. 341, No. 6148, pp. 1-29.
Astori G. et al., Evaluation of ex vivo expansion and engraftment in NOD-SCID mice of umbilical cord blood CD34 + cells using the Dideco 'Pluricell System' Bone Marrow Transplant. vol. 35, 1101-1106, 2005.

(Continued)

*Primary Examiner* — Erich A Leeser
(74) *Attorney, Agent, or Firm* — Buchanan Ingersoll & Rooney P.C.

(57) ABSTRACT

Methods and compositions for enhancing viral gene transfer, such as lentiviral gene transfer, and improving the efficacy of gene delivery to cells such as primitive hematopoietic cells, are described. These methods and compositions are based on the use of pyrimido[4,5-b]indole derivatives. Cell-based compositions and methods useful for therapeutic indications amenable to treatment with gene therapies, including hematopoietic stem cell therapies, are also described.

22 Claims, 27 Drawing Sheets

(56) References Cited

OTHER PUBLICATIONS

Biffi A. et al.,"Lentiviral Hematopoietic Stem Cell Gene Therapy Benefits Metachromatic Leukodystrophy" Science, vol. 341, No. 6148, pp. 1233158-0-1233158-12, Aug. 23, 2013.
Cavazzana-Calvo M. et al.,"Transfusion independence and HMGA2 activation after gene therapy of human β-thalassaemia" Nature, vol. 467, No. 7313, pp. 318-322, Sep. 16, 2010.
Chono, H. et al.,"Optimization of lentiviral vector transduction into peripheral blood mononuclear cells in combination with the fibronectin fragment CH-296 stimulation" J Biochem. Mar. vol. 149, No. 3, pp. 285-292, 2011.
Cronin J. et al.,"Altering the Tropism of Lentiviral Vectors through Pseudotyping" Curr. Gene Ther, vol. 5, No. 4, pp. 1-19, Aug. 2005.
Hannum, C. C.,"Ligand for FLT3/FLK2 receptor tyrosine kinase regulates growth of haematopietic stem cells and is ecoded by variant RNAs" Nature, vol. 368, No. 6472, pp. 643-648, Apr. 14, 1994.
Dull T. et al.,"A Third-Generation Lentivirus Vector with a Conditional Packaging System" Journal of Virology, vol. 72, No. 11, pp. 8463-8471, Nov. 1998.
Fares, I. et al."Pyrimidoindole derivatives are agonists of human hematopoietic stem cell self-renewal". Science. vol. 345, No. 6203, pp. 1509-1512, Sep. 19, 2014.
Fenard, D. et al."Vectofusin-1, a New Viral Entry Enhancer, Strongly Promotes Lentiviral Transduction of Human Hematopoietic Stem Cells" Mol Ther Nucleic Acids. vol. 2, pp. 1-10, May 2013.
Géronimi, F et al."Highly Efficient Lentiviral Gene Transfer in CD34+ and CD34+/38-/lin-Cells from Mobilized Peripheral Blood after Cytokine PrestimulationStem" Cells, vol. 21, No. 4, pp. 472-480, 2003.
Kiem, H.P. et al."Improved Gene Transfer Into Baboon Marrow Repopulating Cells Using Recombinant Human Fibronectin Fragment CH-296 in Combination With Interleukin-6, Stem Cell Factor, FLT-3 Ligand, and Megakaryocyte Growth and Development Factor" Blood, vol. 92, No. 6, pp. 1878-1886, Sep. 15, 1998.
Imren S. et al."Permanent and panerythroid correction of murine thalassemia by multiple lentiviral integration in hematopoietic stem cells" Proc Natl Acad Sci USA. 99. 2002. pp. 14380-14385.
Joglekar, A.V. et al."Integrase-defective Lentiviral Vectors as aDelivery Platform for Targeted Modification of Adenosine Deaminase Locus" Mol Ther, vol. 21, No. 9, pp. 1705-1717, Sep. 2013, PMID 23857176.
Kaushansky, K."Lineage-Specific Hematopoietic Growth Factors" N. Engl. J. Med, vol. 354, No. 9, pp. 2034-2045, May 11, 2006.
Kishimoto, A. "Interleukin-6: From Basic Science to Medicine—40 Years in Immunology" Annu. Rev. Immunol, vol. 23, pp. 1-21, 2005.
Koller, M.R. et al."Clinical-scale human umbilical cord cell expansion in a novel automated perfusion culture system" Bone Marrow Transplant, vol. 21, pp. 653-663, 1998.
Koller, M.R. et al."Large-scale expansion of human stem and progenitor cells from bone marrow mononuclear cells in continuous perfusion cultures" Blood, vol. 82, No. 2, pp. 378-384, Jul. 15, 1993.
Naldini, L. et al."In Vivo Gene Delivery and Stable Transduction of Nondividing Cells by a Lentiviral Vector". Science. New Series. vol. 272, No. 5259, pp. 263-267, Apr. 12, 1996.
Nappi, F. et al."Immobilized HIV-1 Tat protein promotes gene transfer via a transactivation-independent mechanism which requires binding of Tat to viral particles" Gene Med, vol. 11, pp. 955-965, 2009.
Pawliuk et al."Correction of Sickle Cell Disease in Transgenic Mouse Models by Gene Therapy" Science, vol. 294, pp. 2368-2371, Dec. 14, 2001.
Ravot, E. et al."High efficiency lentiviral gene delivery in nondividing cells by deoxynucleoside treatment" J Gene Med, vol. 4, No. 4, pp. 161-169, Feb. 18, 2002.
Landau, N.R. et al."Packaging System for Rapid Production of Murine Leukemia Virus Vectors with Variable Tropism" J. Virol, vol. 66, pp. 5110-5113, Aug. 1992.
Lee, H.J., Lee, Y.S. et al."Retronectin enhances lentivirus-mediated gene delivery into hematopoietic progenitor cells" Biologicals, vol. 37, No. 4, pp. 203-209, 2009.
Logan, A.C. et al."Factors Influencing the Titer and Infectivity of Lentiviral Vectors" Human Gene Therapy, vol. 15, pp. 976-988, Oct. 2004.
Malik et al."Successful Correction of the Human Cooley's Anemia β-Thalassemia Major Phenotype Using a Lentiviral Vector Flanked by the Chicken Hypersensitive Site 4 Chromatin Insulator" NY Acad Sci, vol. 1054. pp. 238-249, 2005.
May, C. et al"Therapeutic haemoglobin synthesis in β-thalassaemic mice expressing lentivirus-encoded human β-globin" Nature, vol. 406, pp. 82-86, Jul. 6, 2000.
Naldini, L."Lentiviruses as gene transfer agents for delivery to non-dividing cells" Current Opinion in Biotechnology, vol. 9, pp. 457-463, 1998.
Naldini, L. et al."Efficient transfer, integration, and sustained long-term expression of the transgene in adult rat brains injected with a lentiviral vector" Proc. Natl. Acad. Sci. USA, vol. 93, pp. 11382-11388, Oct. 1996.
Shaw A. et al."Design and Potential of Non-Integrating Lentiviral Vectors" Biomedicines, vol. 2. pp. 14-35, 2014.
Smith, M.A. et al."Stem Cell Factor. Biology and Relevance to Clinical Practice" ACTA Haematologica, vol. 105, No. 3, pp. 143-150, 2001.
Soneoka Y. et al."A transient three plasmid expression system for the production of high titer retroviral vectors" Nucl. Acids Res, vol. 23, No. 4, pp. 628-633, 1995.
Watts K. L. et al."Hematopoietic Stem Cell Expansion and Gene Therapy" Cytotherapy, vol. 13, No. 10, pp. 1164-1171, Nov. 2011.
Zufferey R. et al."Multiply attenuated lentiviral vector achieves efficient gene delivery in vivo" Nature Biotechnology, vol. 15, pp. 871-875, Sep. 1997.
Schwartz, R.M. et al."Rapid medium perfusion rate significantly increases the productivity and longevity of human bone marrow cultures" Proc. Natl. Acad. Sci. U.S.A, vol. 88, pp. 6760-6764, Aug. 1991.

* cited by examiner

| Mice tag no. | Transduction + culture condition | Lentivirus envelope | MOI | %huCD45+ from total NSG bone marrow cells (Considered positive for % ≤0.1) | %huCD45+ GFP+ from total NSG bone marrow cells | %huCD45+ GFP- from total NSG bone marrow cells |
|---|---|---|---|---|---|---|
| 14406 | DMSO | VSV | 50 | 0.10 | 0.02 | 0.08 |
| 14407 | DMSO | VSV | 100 | 0.80 | 0.14 | 0.66 |
| 14408 | DMSO | RDT114 | 50 | 5.80 | 0.30 | 5.50 |
| 14409 | DMSO | RDT114 | 100 | 6.10 | 0.33 | 5.77 |
| 14410 | DMSO | VSV | 50 | 0.80 | 0.47 | 0.33 |
| 14411 | DMSO | VSV | 100 | 1.60 | 1.11 | 0.49 |
| 14412 | DMSO | untransduced | 0 | 0.20 | 0.00 | 0.20 |
| 14413 | DMSO | untransduced | 0 | 0.60 | 0.00 | 0.59 |
| 14414 | CMPD1 | VSV | 50 | 11.20 | 3.47 | 7.73 |
| 14415 | CMPD1 | VSV | 50 | 13.60 | 4.99 | 8.61 |
| 14416 | CMPD1 | VSV | 100 | 17.50 | 6.70 | 10.80 |
| 14417 | CMPD1 | VSV | 100 | 5.50 | 2.20 | 3.30 |
| 14418 | CMPD1 | RDT114 | 50 | 7.30 | 2.66 | 4.64 |
| 14419 | CMPD1 | RDT114 | 100 | 5.20 | 1.43 | 3.77 |
| 14420 | CMPD1 | VSV | 50 | 3.10 | 2.15 | 0.95 |
| 14421 | CMPD1 | VSV | 50 | 4.00 | 2.98 | 1.02 |
| 14422 | CMPD1 | VSV | 100 | 0.60 | 0.42 | 0.18 |
| 14423 | CMPD1 | VSV | 100 | 3.60 | 2.46 | 1.14 |
| 14424 | CMPD1 | untransduced | 0 | 2.80 | 0.00 | 2.80 |
| 14425 | CMPD1 | untransduced | 0 | 4.40 | 0.00 | 4.40 |

FIG. 4

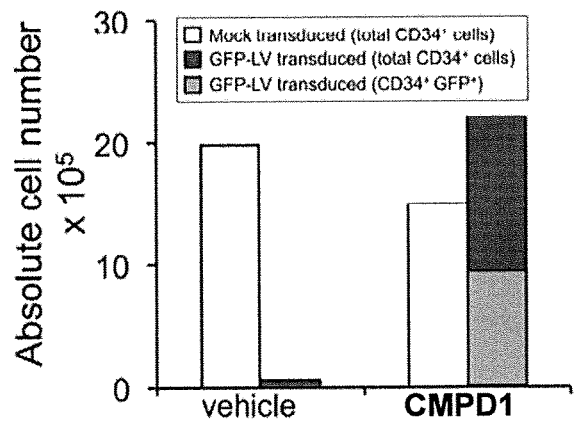
FIG. 18C
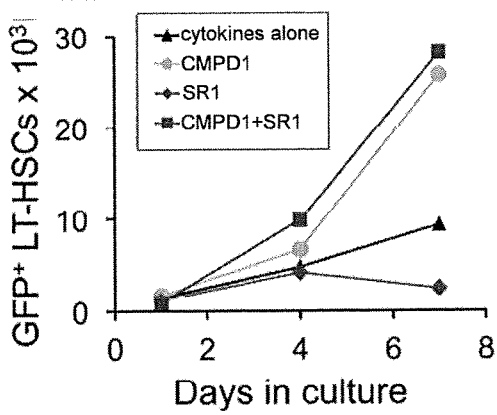
FIG. 18D
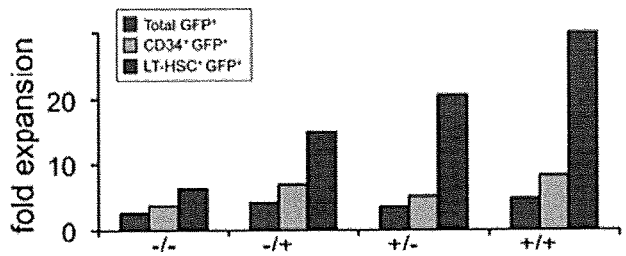
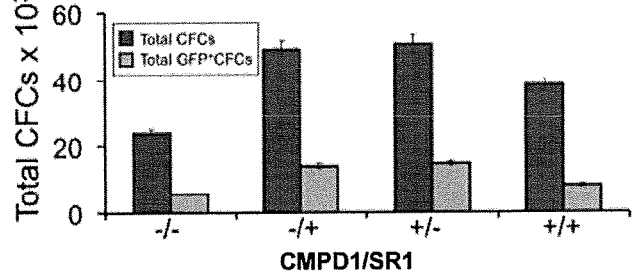
FIG. 18E
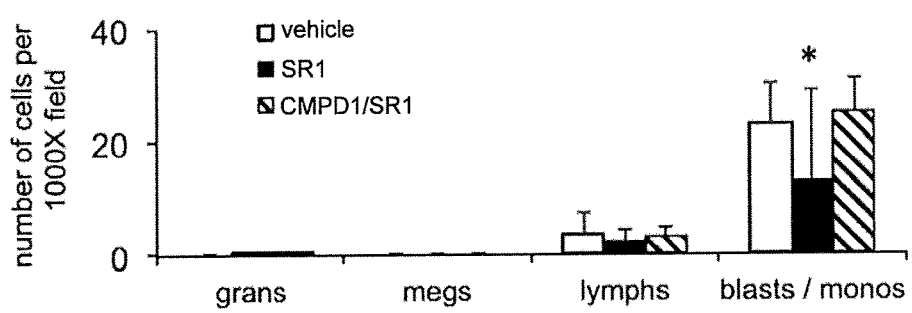
FIG. 18F

COMPOUNDS AND METHODS FOR ENHANCING VIRAL GENE TRANSFER TO HUMAN HEMATOPOIETIC CELLS

GOVERNMENT LICENSE RIGHTS

This invention was made with government support under HL084345 and HL053749 awarded by the National Institutes of Health. The government has certain rights in the invention.

CROSS REFERENCE TO RELATED APPLICATIONS

This application claims the benefit of U.S. Provisional Application Ser. No. 62/052,452, filed on Sep. 18, 2014, which is incorporated herein by reference in its entirety.

TECHNICAL FIELD

The present invention generally relates to viral gene transfer, and more specifically to viral gene transfer to cells such as hematopoietic stem cells (HSCs) and applications thereof.

BACKGROUND ART

Gene transfer to hematopoietic stem cells (HSCs) remains an attractive approach for the treatment of numerous genetic disorders. Recent progress in the field of gene therapy has further raised the hope that patients afflicted with hemoglobinopathies such as β thalassemia and sickle cell anemia will benefit from novel therapeutic approaches. Transplantation of hematopoietic cells (HCs) modified with lentiviral vectors carrying the β-globin gene has resulted in long-term correction of several mouse models of hemoglobin disorders (Imren et al, *Proc Natl Acad Sci USA*. 2002; 99: 14380-14385; Malik et al., Ann NY Acad Sci. 2005; 1054:238-249; May et al, Nature. 2000; 406:82-86; Pawliuk et al, Science. 2001; 294: 2368-2371), but has led to transfusion independency in only one β thalassemic patient (Cavazzana-Calvo et al, Nature. 2010; 467:318-322).

The safety and utility of such treatments, however, are limited by difficulties in achieving sufficient numbers of transduced HSCs, either because of poor yields or functionality of the transduced cells. The use of different agents to enhance retroviral gene transfer has been reported, for example fibronectin (U.S. Pat. No. 5,686,278, Chono H et al. *J Biochem.* 2011 March; 149(3):285-92; Lee H J, Lee Y S, et al. *Biologicals*. 2009 August; 37(4):203-9), HIV Tat (Nappi F, et al. J Gene Med. 2009 November; 11(11):955-65), Vectofusin-1 (Fenard D, et al., Mol Ther Nucleic Acids. 2013 May 7; 2:e90), deoxynucleosides (Ravot E, et al., J Gene Med. 2002 March-April; 4(2):161-9), and cytokines (Geronimi F et al. Stem Cells. 2003; 21(4):472-80; Kiem H P, et al., *Blood*. 1998 Sep. 15; 92(6):1878-86).

There is thus a need for novel compounds and methods for enhancing gene transfer to HSCs, particularly in methods of gene therapy for the treatment or prevention of hematopoietic disorders.

The present description refers to a number of documents, the content of which is herein incorporated by reference in their entirety.

SUMMARY OF THE INVENTION

The present invention relates to the following items [1] to [37]:

[1]. A method for transducing a viral vector into cells, said method comprising contacting said cells with a compound of general formula I; and transducing said cells with a viral vector,

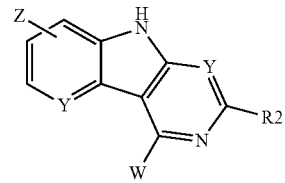

or a salt or a prodrug thereof,
wherein:
each Y is independently selected from N and CH;
Z is
  1) —CN
  2) —C(O)OR1,
  3) —C(O)N(R1)R3,
  4) —C(O)R1, or
  5) -heteroaryl optionally substituted with one or more RA or R4 substituents,
wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is
  1) —CN,
  2) —N(R1)R3,
  3) —C(O)OR1,
  4) —C(O)N(R1)R3,
  5) —NR1C(O)R1,
  6) —NR1C(O)OR1,
  7) —OC(O)N(R1)R3,
  8) —OC(O)R1,
  9) —C(O)R1,
  10) —NR1C(O)N(R1)R3,
  11) —NR1S(O)$_2$R1,
  12) -benzyl optionally substituted with 1, 2 or 3 RA or R1 substituents,
  13) —X-L-(X-L)n-N(R1)R3,
  14) —X-L-(X-L)n-heteroaryl optionally substituted with one or more RA or R4 substituents attached on either or both the L and heteroaryl groups,
  15) —X-L-(X-L)n-heterocyclyl optionally substituted with one or more RA or R4 substituents attached on either or both the L and heterocyclyl groups,
  16) —X-L-(X-L)n-aryl optionally substituted with one or more RA or R4 substituents,
  17) —X-L-(X-L)$_n$-NR1RA or
  18) —(N(R1)-L)$_n$-N$^+$R1R3R5R6$^-$
wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from O, S, and NR1;
each L is independently
  1) —C$_{1-6}$ alkylene,
  2) —C$_{2-6}$ alkenylene,
  3) —C$_{2-6}$ alkynylene, 4) —C$_{3-7}$cycloalkylene, which optionally includes one or more other heteroatom selected from N, O and S or
5) —C3-7 cycloalkenylene, which optionally includes one or more other heteroatom selected from N, O and S wherein the alkylene, the alkenylene, the alkynylene the cycloalkylene and the cycloalkenylene groups are each independently optionally substituted with one or two R4 or RA substituent;

R1 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl, wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is
1) —H,
2) —C$_{1-6}$ alkyl, optionally substituted with one more RA substituents
3) —C(O)R4,
4) -L-heteroaryl optionally substituted with one or more RA or R4 substituents
5) -L-heterocyclyl optionally substituted with one or more RA or R4, or
6) -L-aryl optionally substituted with one or more RA or R4 substituents;

R3 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently
1) —C$_{1-6}$ alkyl,
2) —C$_{1-6}$ alkylene-C$_{2-6}$ alkenyl which optionally includes one or more other heteroatom selected from N, O and S
3) —C$_{1-6}$ alkylene-C$_{2-6}$ alkynyl which optionally includes one or more other heteroatom selected from N, O and S
4) -L-aryl which optionally includes one or more RA or R4 substituents
5) -L-heteroaryl which optionally includes one or more RA or R4 substituents
6) —C$_{1-6}$ alkylene-C(O)O—
7) —C$_{1-6}$ alkylene-C(O)OR1
8) —C$_{1-6}$ alkylene-CN
9) —C$_{1-6}$ alkylene-C(O)NR1R3, wherein R1 and R3 optionally they join together with the nitrogen atom to form a 3 to 7-membered ring which optionally includes one or more other heteroatom selected from N, O and S; or
10) —C$_{1-6}$ alkylene-OH;

R6 is
1) Halogen
2) OC(O)CF$_3$ or
3) OC(O)R1;

RA is each independently
1) -halogen,
2) —CF$_3$,
3) —OR1,
4) -L-OR1,
5) —OCF$_3$,
6) —SR1,
7) —CN,
8) —NO$_2$,
9) —NR1R3,
10) -L-NR1R1,
11) —C(O)OR1,
12) S(O)$_2$R4
13) —C(O)N(R1)R3,
14) —NR1C(O)R1,
15) —NR1C(O)OR1,
16) —OC(O)N(R1)R3,
17) —OC(O)R1,
18) —C(O)R4,
19) —NHC(O)N(R1)R3,
20) —NR1C(O)N(R1)R3, or
21) —N$_3$; and Rd is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated
8) -benzyl or
9) -heterocyclyl.

[2]. The method according to item 1, wherein the compound is of formula IA

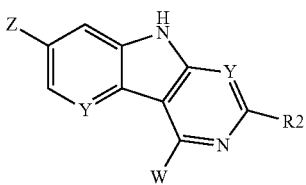

or a salt or a prodrug thereof,
wherein W, Y, Z and R2 are each as defined in item 1.

[3]. The method according to item 2, wherein
each Y is independently selected from N and CH;
Z is —CN, —C(O)OR1, —C(O)N(R1)R3, or -heteroaryl optionally substituted with one or more RA or R4 substituents,
W is —CN, —N(R1)R3, -benzyl optionally substituted with 1, 2 or 3 RA or R1 substituents, —X-L-(X-L)n-N(R1)R3, —X-L-(X-L)$_n$-NR1RA or —(N(R1)-L)$_n$-N$^+$R1R3R5R6$^-$
wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently O, S, or NR1,
L is each independently —C$_{1-6}$ alkylene, —C$_{2-6}$ alkenylene, —C$_{2-6}$ alkynylene, —C3-7 cycloalkylene, which optionally includes one or more other heteroatom selected from N, O and S or —C3-7 cycloalkenylene, which optionally includes one or more other heteroatom selected from N, O and S,
wherein the alkylene, the alkenylene, the alkynylene the cycloalkylene and the cycloalkenylene are each independently optionally substituted with one or two R4 or RA substituent;
R1 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is —H, —C$_{1-6}$ alkyl, optionally substituted with one more RA substituents, —C(O)R4, -L-heteroaryl optionally substituted with one or more RA or R4 substituents, -L-heterocyclyl optionally substituted with one or more RA or R4, or -L-aryl optionally substituted with one or more RA or R4 substituents;
R3 is each independently —H, —C$_{1-6}$ alkyl, —C$_{2-6}$ alkenyl, —C$_{2-6}$ alkynyl, or —C$_{1-5}$ perfluorinated,
wherein the alkyl, the alkenyl, the alkynyl, the perfluorinated alkyl groups are each independently optionally substituted with 1, 2 or 3 RA or Rd substituents;
R4 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -aryl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R5 is each independently —C$_{1-6}$ alkyl, -L-aryl which optionally includes one or more RA or R4 substituents, -L-heteroaryl which optionally includes one or more RA or R4 substituents, —C$_{1-6}$ alkylene-C(O)O—, —C$_{1-6}$ alkylene-C(O)OR1, —C$_{1-6}$ alkylene-CN, —C$_{1-6}$ alkylene-C(O)NR1R3, or —C$_{1-6}$ alkylene-OH;
R6 is Halogen, —OC(O)CF$_3$ or OC(O)R1;
RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$;
Rd is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -benzyl or -heterocyclyl.

[4]. The method according to item 1, wherein the compound is of formula IIA:

IIA or a salt or a prodrug thereof,
wherein Z, W and R2 are each as defined in item 1.

[5]. The method according to item 4, wherein
Z is —CN, —C(O)O—C$_{1-6}$ alkyl, —C(O)NH—C$_{1-6}$ alkyl, or -heteroaryl optionally substituted with one or more RA or R4 substituents,
W is —N(R1)R3, —NR1-C$_{1-6}$ alkylene-N(R1)R3, —O—C$_{1-6}$ alkylene-N(R1)R3, —S—C$_{1-6}$ alkylene-N(R1)R3, —NR1-C$_{1-6}$ alkylene-NR1RA, —NR1-C$_{1-6}$ alkylene-(NR1-C$_{1-6}$ alkylene)$_n$-NR1R3 or —NR1-C$_{1-6}$ alkylene-(NR1-C$_{1-6}$ alkylene)$_n$-NR1RA;
wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
R1 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is —H, —C$_{1-6}$ alkyl, —C(O)R4, —C$_{1-6}$ alkylene-heteroaryl optionally substituted with one or more RA or R4 substituents either on the alkylene or the heteroaryl, —C$_{1-6}$ alkylene-heterocyclyl optionally substituted with one or more RA or R4, or —C$_{1-6}$ alkylene-aryl optionally substituted with one or more RA or R4 substituents either on the alkylene or the heteroaryl;
R3 is each independently —H, —C$_{1-6}$ alkyl, —C$_{2-6}$ alkenyl, —C$_{2-6}$ alkynyl, or —C$_{1-5}$ perfluorinated,
wherein the alkyl, the alkenyl, the alkynyl, the perfluorinated alkyl groups are each independently optionally substituted with 1, 2 or 3 RA or Rd substituents;
R4 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -aryl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

RA is each independently -halogen, —CF₃, —OR1, -L-OR1, —OCF₃, —SR1, —CN, —NO₂, —NR1R3, -L-NR1R1, —C(O)OR1, S(O)₂R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N₃;

Rd is each independently —H, —C₁₋₆ alkyl, —C₂₋₆ alkenyl, —C₂₋₆ alkynyl, —C₃₋₇ cycloalkyl, —C₃₋₇ cycloalkenyl, —C₁₋₅ perfluorinated, -benzyl or -heterocyclyl.

[6]. The method according to claim 5, wherein:
Z is CO₂Me or 2-methyl-2H-tetrazol-5-yl;
R2 is benzyl, or H; and
W is NH-L-N(R1)R3 wherein L is C2-4 alkylene or C3-7 cycloalkylene and R1 and R3 is C1-4 alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

[7]. The method according to item 6, wherein W is

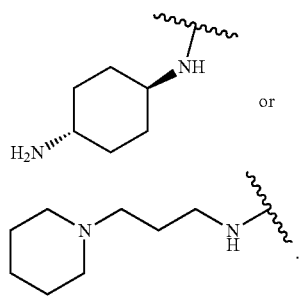

or

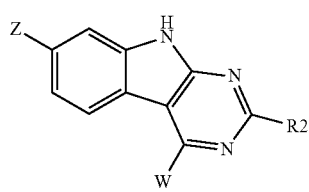

[8]. The method of item 1, wherein the compound is of formula IIA

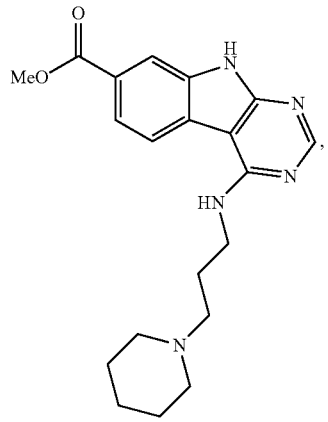

IIA or a salt thereof, wherein
Z is —C(O)O—C₁₋₄ alkyl, or -heteroaryl, preferably a 5-membered ring heteroaryl comprising 2-4 heteroatoms selected from N and O, optionally substituted with one or more RA or R4 substituents, W is —N(R1)R3, —NR1-C₁₋₆ alkylene-N(R1)R3, —O—C₁₋₆ alkylene-N(R1)R3, —S—C₁₋₆ alkylene-N(R1)R3, or —NR1-C₁₋₆ alkylene-(NR1-C₁₋₆ alkylene)ₙ-NR1R3, wherein n is an integer equal to either 0, 1, 2, or 3 and wherein, when R1 and R3 are attached to the same nitrogen atom, optionally they join together with the nitrogen atom to form a 5 to 6-membered ring which optionally includes one or more other heteroatom selected from N and O, optionally the ring is substituted with one or more RA or R4;

R1 is each independently —H, —C₁₋₆ alkyl, —C₃₋₇ cycloalkyl, or -heterocyclyl,
wherein the alkyl, the cycloalkyl, the heterocyclyl are each independently optionally substituted with 1, 2 or 3 RA or Rd substituents;

R2 is —H, —C₁₋₆ alkyl, —C₁₋₆ alkylene-heteroaryl optionally substituted with one or more RA or R4 substituents either on the alkylene or the heteroaryl; or —C₁₋₆ alkylene-aryl optionally substituted with one or more RA or R4 substituents either on the alkylene or the aryl;

R3 is each independently —H, —C₁₋₆ alkyl, wherein the alkyl group is optionally substituted with 1, 2 or 3 RA or Rd substituents;

R4 is each independently H, —C₁₋₆ alkyl, wherein the alkyl is optionally substituted with 1, 2 or 3 RA or Rd substituents;

RA is each independently -halogen, —CF₃, —OR1, —OCF₃, —SR1, —CN, —NO₂, —NR1R3, —C(O)OR1, S(O)₂R4, —C(O)N(R1)R3, —NR1C(O)R1, —NR1C(O)OR1, —OC(O)N(R1)R3, —OC(O)R1, —C(O)R4, —NHC(O)N(R1)R3, or —NR1C(O)N(R1)R3, and Rd is each independently —H, or —C₁₋₆ alkyl.

[9]. The method of item 1, wherein said compound is:

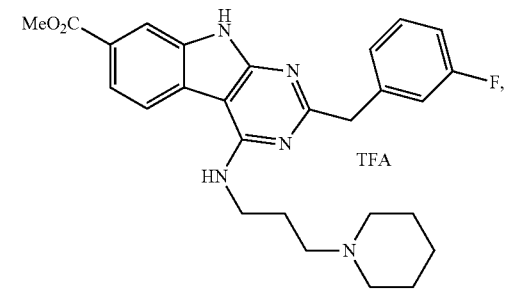

-continued

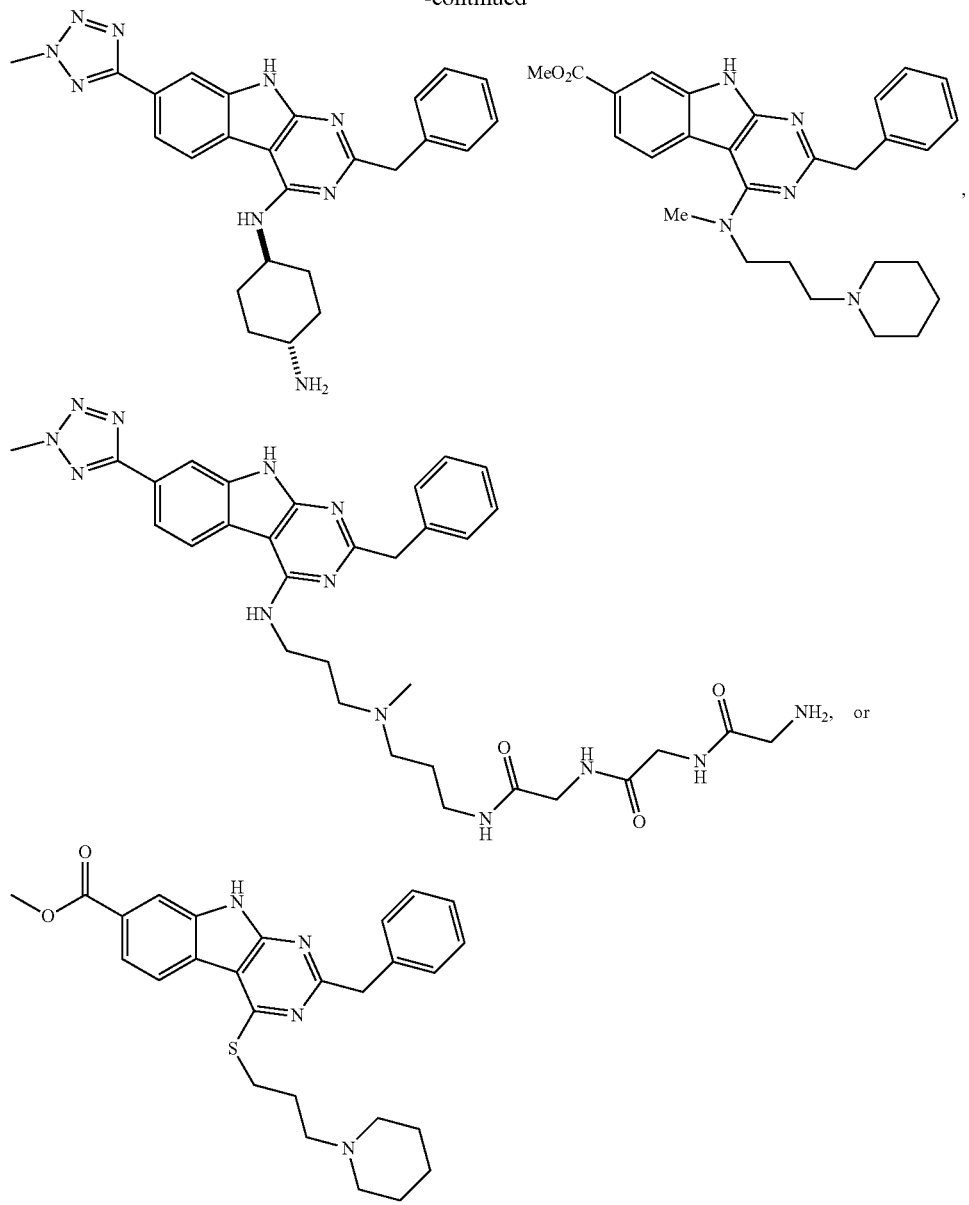

or a salt thereof.

[10]. The method of any one of items 1 to 9, wherein said cells comprise stem cells and/or progenitor cells.

[11]. The method of item 10, wherein said stem cells comprise primitive hematopoietic cells.

[12]. The method of item 11, wherein said primitive hematopoietic cells are derived from cord blood, bone marrow or peripheral blood.

[13]. The method of any one of items 1 to 12, wherein said viral vector is an integration defective viral vector.

[14]. The method of any one of items 1 to 13, wherein said viral vector is a lentiviral vector.

[15]. The method of item 14, wherein said lentiviral vector is a pseudo-typed lentiviral vector.

[16]. The method of item 15, wherein the lentiviral vector is pseudotyped with a vesicular stomatitis virus G-protein (VSV-G) or a RAD114 envelope protein.

[17]. The method of any one of items 1 to 16, wherein said cells are contacted with said compound prior to said transducing.

[18]. The method of any one of items 1 to 16, wherein said are contacted with said compound prior to and during said transducing.

[19]. The method of any one of items 1 to 18, wherein said cells are contacted with said compound for a period of about 2 to about 22 hours.

[20]. A composition comprising: (i) cells as defined in any one of items 1 and 10-12, (ii) at least one of the compounds defined in any one of items 1 to 9; and (iii) a viral vector as defined in any one of items 1 and 13-16.

[21]. The composition of item 20, further comprising (iv) a culture medium suitable for cell expansion.

[22]. The composition of item 20 or 21, wherein said cells comprise stem cells.

[23]. The composition of item 22, wherein said stem cells comprise primitive hematopoietic cells.

[24]. The composition of item 23, wherein said primitive hematopoietic cells are derived from cord blood, bone marrow or peripheral blood.

[25]. A population of transduced cells obtained by the method of any one of items 1 to 19.

[26]. A pharmaceutical composition comprising the population of transduced cells of item 25.

[27]. A method of treating a subject in need of a treatment with cell gene therapy, said method comprising administering to said subject an effective amount of the population of transduced cells of item 25 or the pharmaceutical composition of item 26.

[28]. The method of item 27, wherein said method comprises: (i) transducing a viral vector into cells from said subject in the presence of the compound of general formula I defined in any one of items 1 to 9, thereby obtaining a population comprising transduced cells; and (ii) administering to said subject an effective amount of the population comprising transduced cells obtained in (i), or a pharmaceutical composition comprising said population comprising transduced cells.

[29]. The method of item 28, wherein said cells are as defined in any one of items 22 to 24.

[30]. The method of any one of items 27 to 29, wherein said subject suffers from a hematologic or lysosomal storage disease.

[31]. The method of item 30, wherein said hematologic or lysosomal storage disease is Wiskott-Aldrich syndrome (WAS), metachromatic leukodystrophy (MLD), Leukocyte adherence deficiency, X-linked CGD, Fanconi anemia, adrenoleukodystrophy, Mucopolysaccharidosis IIIA, severe combined immunodeficiency (SCID) or adenosine deaminase (ADA) deficiency.

[32]. Use of the population of transduced cells of item 25 or the pharmaceutical composition of item 26 for treating a subject in need of a treatment with cell gene therapy.

[33]. Use of the population of transduced cells of item 25 or the pharmaceutical composition of item 26 for the manufacture of a medicament for treating a subject in need of a treatment with cell gene therapy.

[34]. The use of item 32 or 33, said subject suffers from a hematologic or lysosomal storage disease.

[35]. The use of item 34, wherein said hematologic or lysosomal storage disease is Wiskott-Aldrich syndrome (WAS), metachromatic leukodystrophy (MLD), Leukocyte adherence deficiency, X-linked CGD, Fanconi anemia, adrenoleukodystrophy, Mucopolysaccharidosis IIIA, severe combined immunodeficiency (SCID) or adenosine deaminase (ADA) deficiency.

[36]. A method for expressing a gene of interest in a cell, said method comprising contacting said cells with a compound of general formula I as defined in any one of items 1 to 9; and transducing said cells with a viral vector comprising a nucleic acid encoding said gene of interest.

[37]. The method of item 36, wherein the viral vector is as defined in any one of items 1 and 13-16.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 3A: Percentages of human CD45+ cells within total NSG BM cells. FIG. 3B: GFP+ cells within human CD45 cells are shown.

FIG. 4 shows a summary of in vivo data 30 weeks post-transplantation with RD114 and VSV-G pseudo-typed lentiviral vectors.

MNDUSNA10hdpgkGFP respectively. The vector constructs were sequence-verified. High-titer recombinant virus pseudotyped with vesicular stomatitis virus glycoprotein-G was produced by transient transfection of 293T cells using a standard 4-plasmid packaging system. Virus-containing supernatants were concentrated by ultracentrifugation to achieve titers of $0.5 \times 10^9$ to $5 \times 10^9$ infectious units/ml. Viral titers were determined by transducing HeLa cells with three dilutions of the lentiviral vector.

Figure 5A:
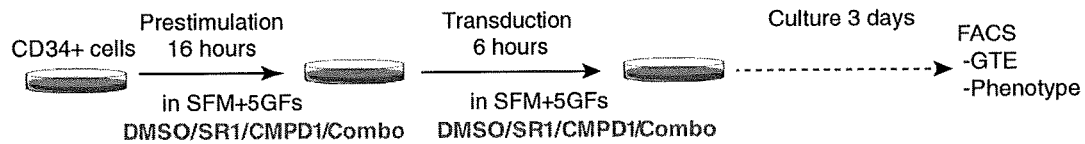
FIG. 5A shows the schematic of experimental design. 20,000 CD34+ cord blood cells isolated by FACS were pre-stimulated for 16 hours in 100 microliters of a serum-free medium [Iscove's medium supplemented with bovine serum albumin, insulin and transferrin (BIT, STEMCELL Technologies), 10 µg/ml of low density lipoprotein (LDL, STEMCELL Technologies), $10^{-4}$ M 2-mercaptoethanol (Sigma-Aldrich), $10^{-4}$ M glutamax 500 (STEMCELLTechnologies) penicillin streptomycin)] plus human growth factors (100 ng/ml SCF, 100 ng/ml FLT3L, 20 ng/ml IL-3, 20 ng/ml IL-6 and 20 ng/ml G-CSF) in the presence or absence of Cmpd1 (35 nM) and/or SR1 (0.75 µM). The cells were then exposed for 6 hours to a GFP lentiviral vector ($10^6$ iu/mL) in the same medium. (Details of the lentiviral vector and the generation and titration of viral stocks used are provided in FIG. 5C.) At the end of the transduction period, cells were washed and cultured for 72 hours in the same medium supplemented with DMSO, SR1 (0.75 µM), Cmpd1 (35 nM), or SR1+Cmpd1. At the end of the culture media, cells were harvested, stained for CD34 and analysed by flow cytometry.
Figure 5B:
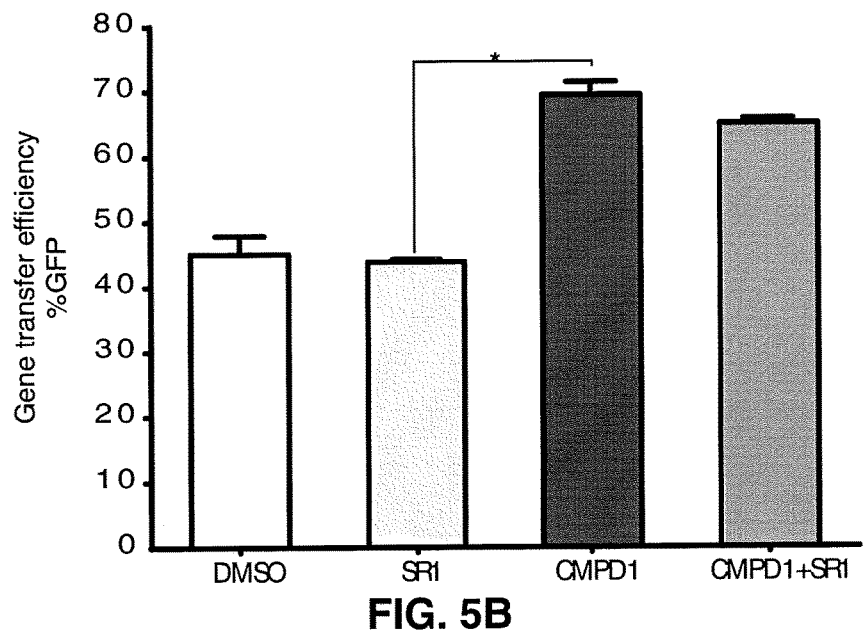
FIG. 5B shows the proportion in percent of CD34+ cells that were GFP+(*p<0.05).
Figure 5C:
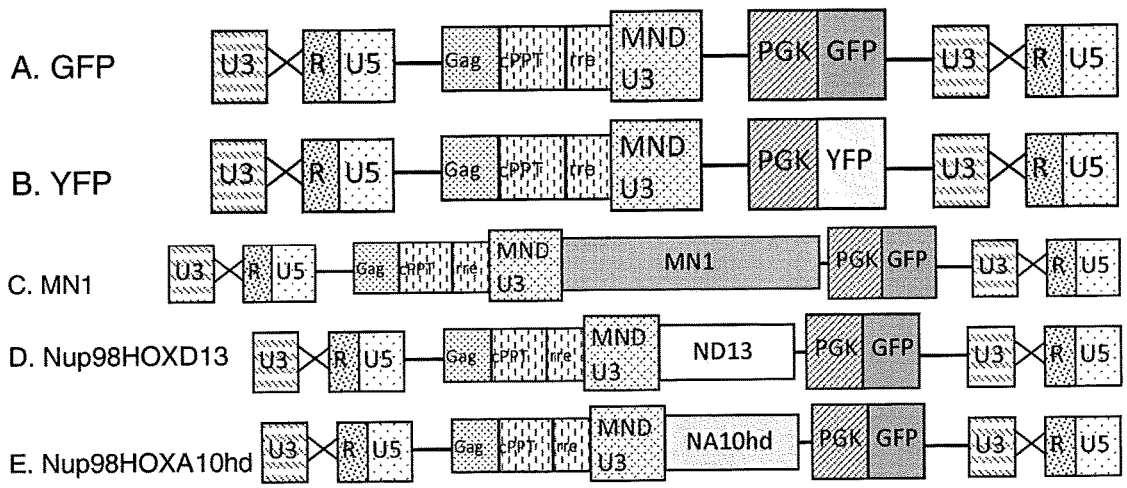
FIG. 5C shows the details of the lentiviral vector and the generation and titration of viral stocks used in the experiments described herein. The pCCI-c-MNDUSpgkGFP or pCCI-c-MNDUSpgkYFP lentiviral vector backbone was used in these studies (Logan A C et al., Human Gene Therapy 2004). The 4000 bp cDNA of MN1 or 1743 bp NUP98-HOXD13 or 1640 bp NUP98-HOXA10hd fusion genes were cloned to generate pCCI-c-MNDUSMNIpgk-GFP or pCCI-c-MNDUSFND3pgkGFP or pCCI-c-
Figure 6A:
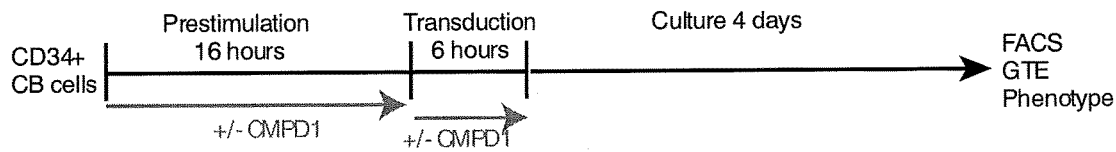

FIG. 6A shows a schematic of experimental design. 20,000 CD34+ cord blood cells isolated by FACS were prestimulated and transduced with a GFP lentiviral vector under culture conditions described in FIG. 5A. Cmpd1 (35 nM) or DMSO was added during the prestimulation or during the transduction period. Cells transductions were carried out using a GFP lentivirus diluted to cover a range of final viral concentrations ranging from $10^5$ to $10^9$ virions/mL (details of virus provided in FIG. 5C).

Figure 6B:
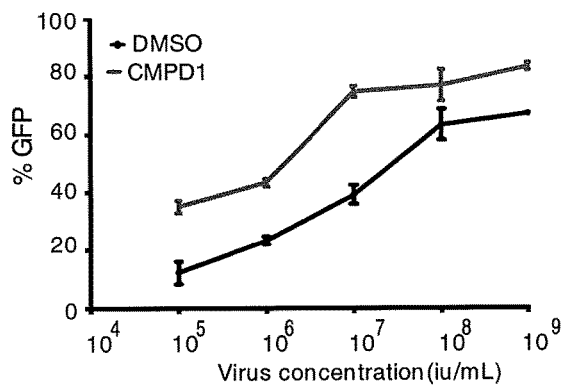
Figure 6C:
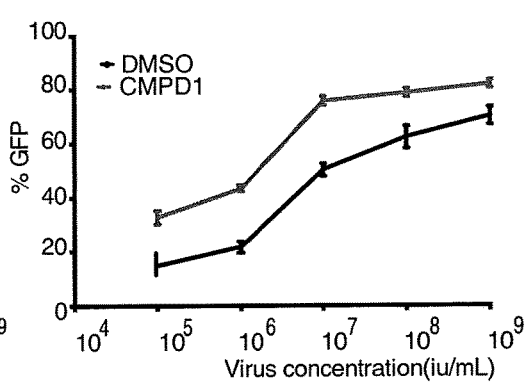

FIGS. 6B and 6C show gene transfer assessed on CD34+ cells after culture with cells exposed to Cmpd1 (upper bars) or DMSO (lower bars) during the prestimulation period (FIG. 6B) or the transduction period (FIG. 6C) period as a function of viral concentration used.

Figure 6D:
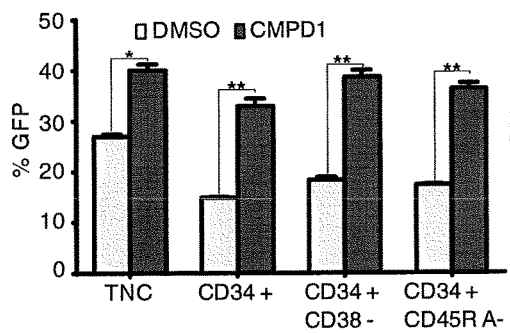
Figure 6E:
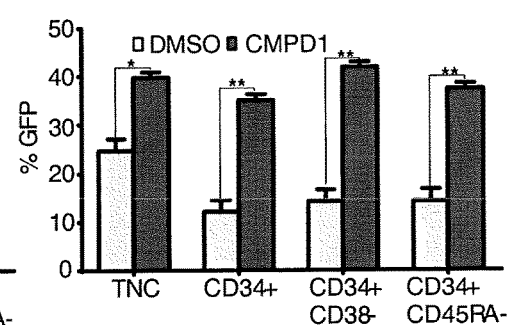

FIGS. 6D and 6E show gene transfer efficiency across different subsets of human hematopoietic cells with Cmpd1 or DMSO present during the prestimulation period (FIG. 6D) or the transduction period (FIG. 6E).

Figure 6F:
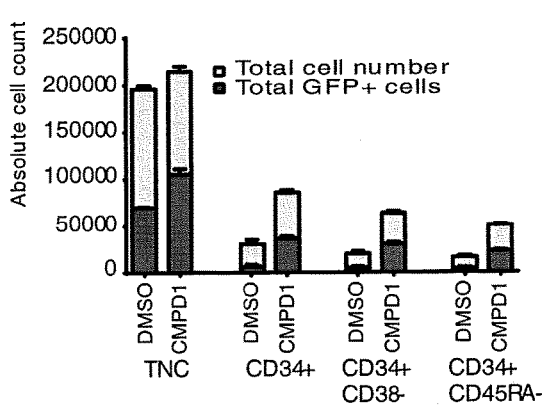
Figure 6G:
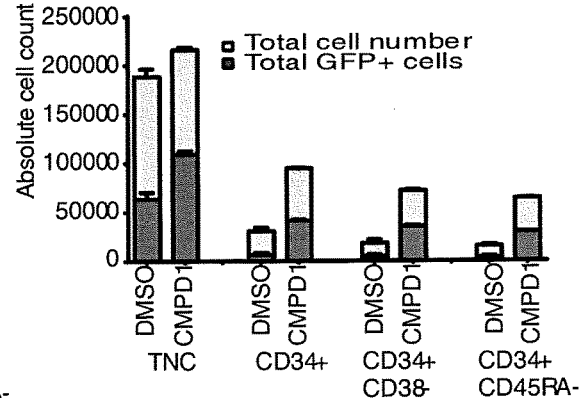
Figure 7A:
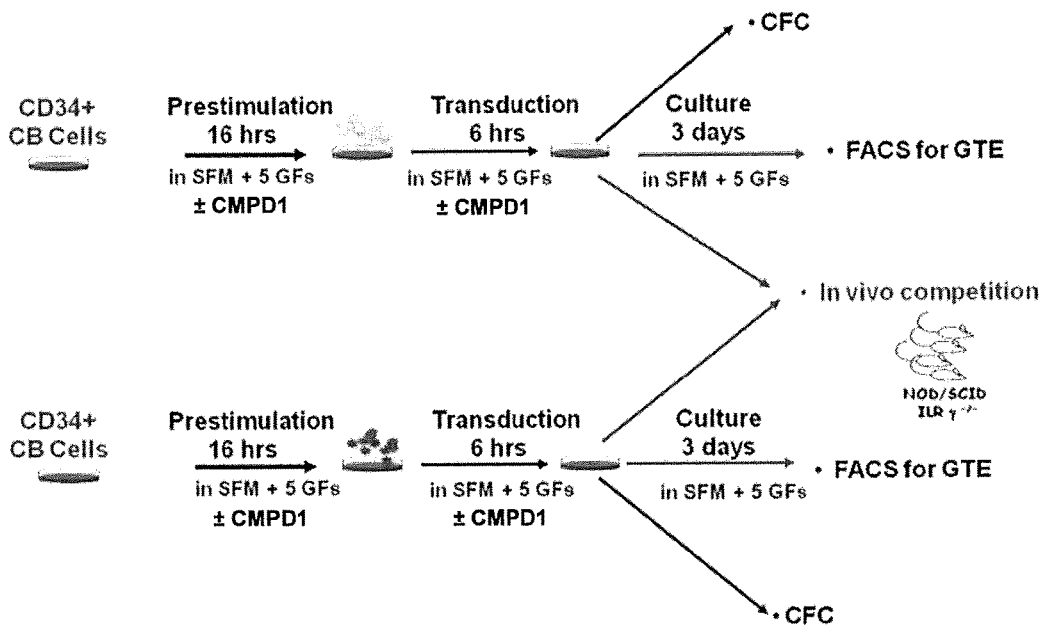

FIGS. 6F and 6G show yield of human hematopoietic subsets with Cmpd1 or DMSO present during the prestimulation period (FIG. 6F) or the transduction period (FIG. 6G). Data for FIGS. 6D-6G obtained with viral concentrations of $10^6$ iu/mL FIG. 7A shows the experimental design to assess the effect of Cmpd1 on gene transfer and yield of primitives cells assessed in vitro and in vivo; cell were transduced with GFP or YFP to allow in vivo tracking of cells transduced under different conditions when co-injected into recipient immunodeficient mice (competitive repopulation). The culture conditions, cell numbers and viruses used are as described in FIGS. 5A and 5C, respectively. For these experiments Cmpd1 was added at a final concentration of 35 nM and viral concentrations for GFP or YFP vectors were $10^6$ iu/mL. All cultures were set up in triplicates.

Figure 7B:
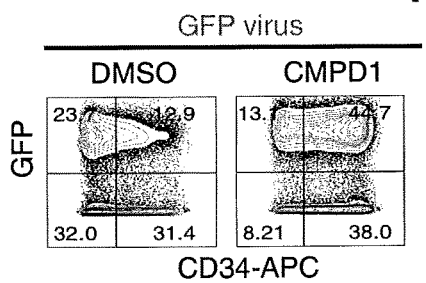
Figure 7C:
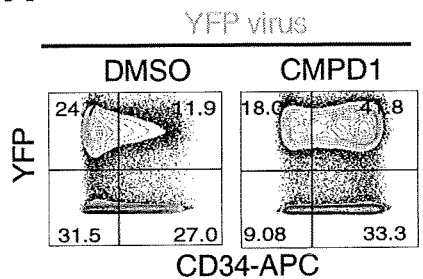

FIGS. 7B and 7C show representative flow cytometry analysis of CD34 and GFP or YFP expression in cells recovered 3 days after transduction with GFP (FIG. 7B) or YFP (FIG. 7C) viruses in presence or absence of Cmpd1.

Figure 7D:
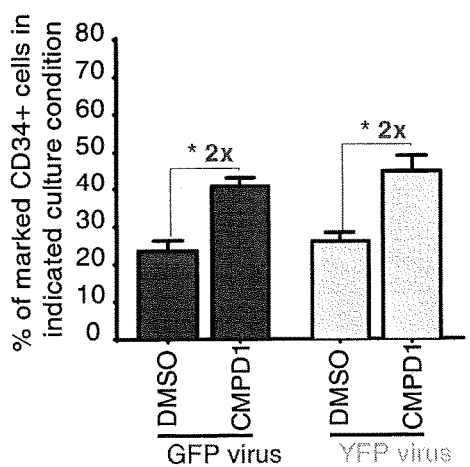

FIG. 7D shows the gene transfer efficiency to human CD34+ CB cells transduced with GFP vector (left, dark gray bars) or YFP vector (right, light gray bars) (n=3; error bars indicate SD; * P<0.05).

Figure 7E:
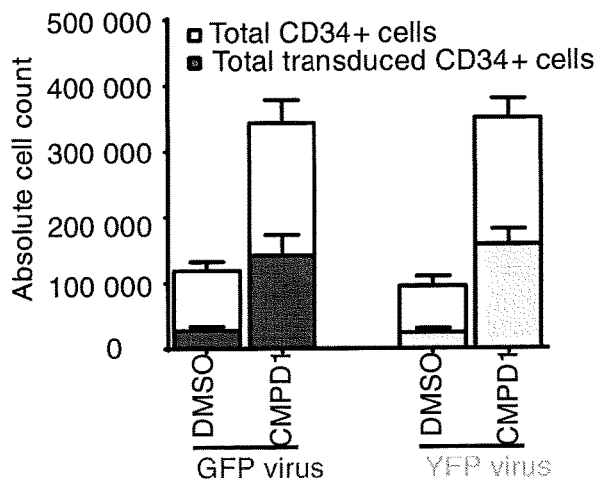

FIG. 7E shows the absolute number of CD34+ cells and GFP marked CD34+ cells (left, dark gray bars) or YFP marked CD34+ cells (right, light gray bars) recovered at the end of 3 days culture (n=3; error bars indicate SD; * P<0.05).

Figure 7F:
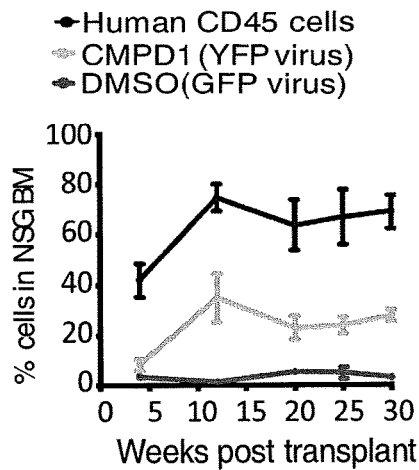
Figure 7G:
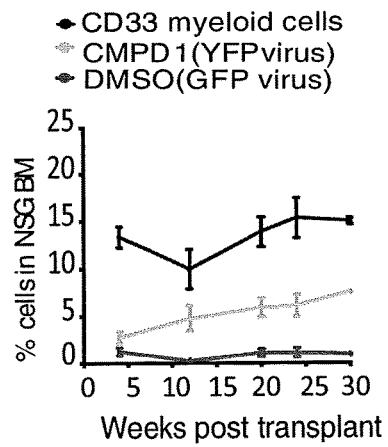
Figure 7H:
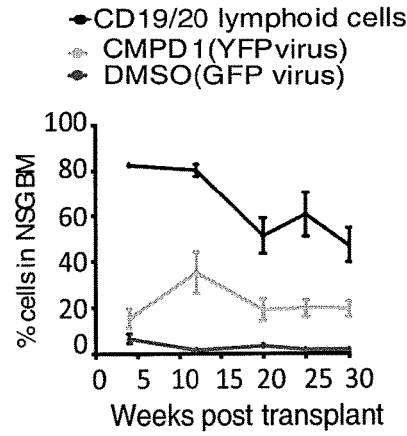

FIGS. 7F, 7G and 7H show the results of in vivo competition experiments for cells transduced in presence or absence of Cmpd1. Immediately after the prestimulation and transduction period (22 hrs) an equal aliquot (20 000) of YFP marked cells (transduced in presence of Cmpd1) and GFP marked cells (transduced in presence of DMSO) were washed and injected into lethally irradiated NSG (n=8). The lymphomyeloid engraftment in bone marrow aspirates was monitored over 30 weeks. FIG. 7F: Detection of total human $CD45^+$ cells (upper black line), YFP+ (middle light gray line) or GFP+(lower dark gray line) cells in the bone marrow of transplanted NSG mice. FIG. 7G: Detection of human $CD33^+$ (myeloid) cells (upper black bar), YFP+ (middle light gray bar) or GFP+ cells (lower dark gray bar) in the bone marrow of transplanted NSG mice. FIG. 7H: Detection of human CD19/20 (B lymphoid) cells (upper black bar), YFP+ (middle light gray bar) or GFP+ cells (lower dark gray bar) in the bone marrow of transplanted NSG mice.

FIGS. 8A to 8E show independent experiment (Expt 2) showing Cmpd1 stimulated enhancement of gene transfer to human CD34+ CB cells (in vitro) and human HSC in NSG mice (in vivo, n=2). The experimental design was as described in FIG. 7 under culture conditions as described in FIG. 5. Viral concentrations and Cmpd1 concentrations were as described in FIG. 7 (106 iu/ml and 35 nM respectively).

Figure 8A:
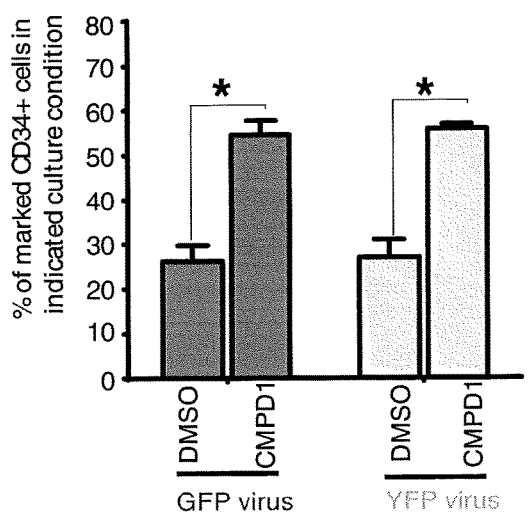

FIG. 8A shows gene transfer efficiency to human CD34+ CB cells transduced with a GFP vector (left, dark gray bars) or an YFP vector (right, light gray bars).

Figure 8B:
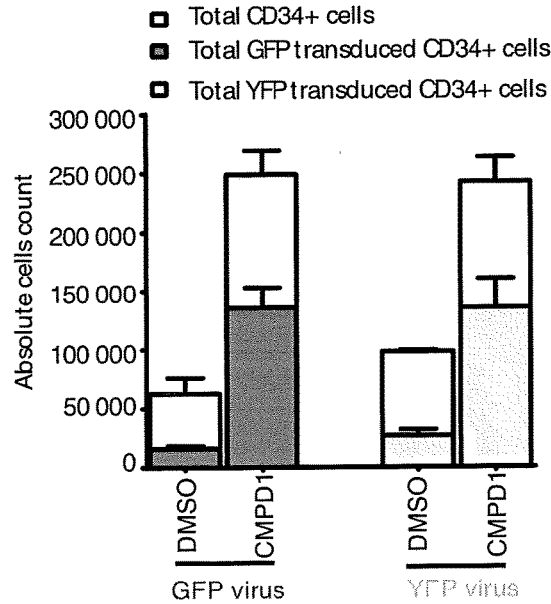

FIG. 8B shows the absolute number of CD34+ cells and GFP marked CD34+ cells (left, dark gray bars) or YFP marked CD34+ cells (right, light gray bars) recovered at the end of a 3-day culture.

Figure 8C:
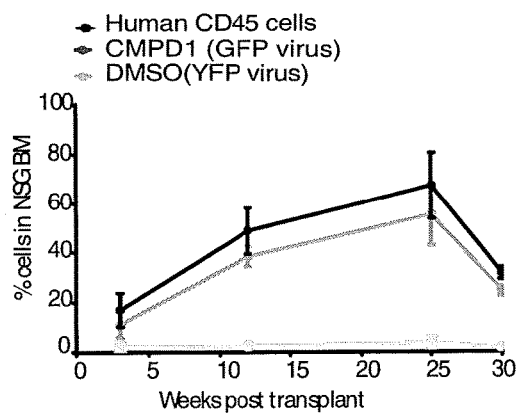

FIG. 8C shows the detection of human $CD45^+$ cells (upper black line), GFP+(middle dark gray line) or YFP+ (lower light gray line) cells in the bone marrow of transplanted NSG mice as a function of time post-transplant.

Figure 8D:
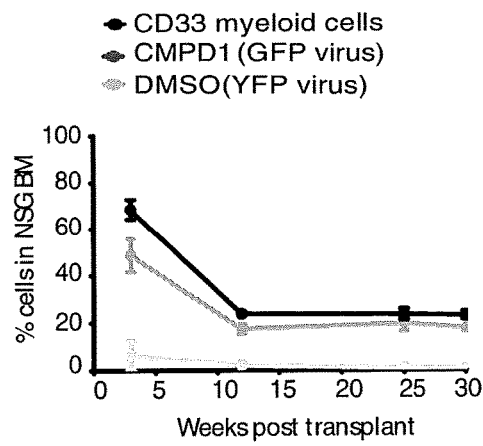

FIG. 8D shows the detection of human CD33 (myeloid) cells (upper black line), GFP+ (middle dark gray line) or YFP+(lower light gray line) in the bone marrow of transplanted NSG mice.

Figure 8E:
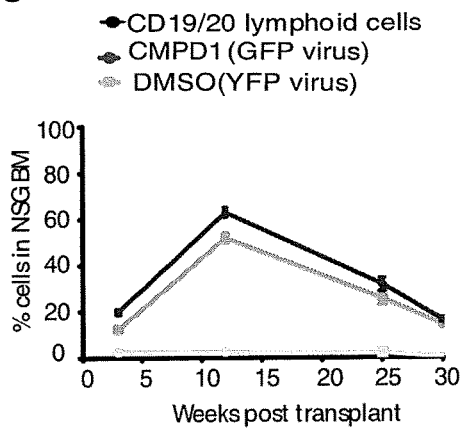

FIG. 8E shows the detection of human CD19/20 (B lymphoid) cells (upper black line), GFP+ (middle dark gray line) or YFP+(lower light gray line) cells in the bone marrow of transplanted NSG mice.

FIGS. 9A to 9D show independent experiment (Expt 3) showing Cmpd1 stimulated enhancement of gene transfer to human CD34+ CB cells (in vitro) and human HSC in NSG mice.

Figure 9A:
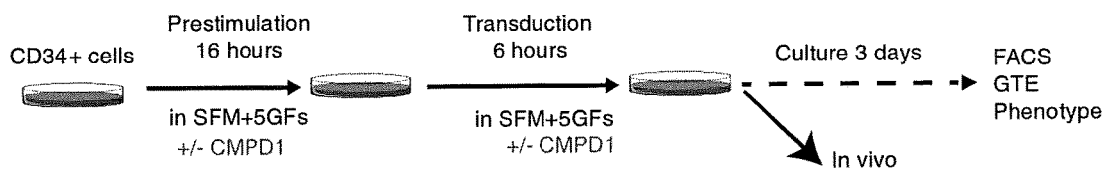

FIG. 9A shows the schematic of experimental design. Unique features of this experiment include use of a different cord blood pool as a source of CD34+ cells; use of a different GFP lentiviral preparation; and assessment of cells in vivo under limit dilution rather than competition assay. Other conditions of culture including concentrations of virus and Cmpd1 are as described previously.

Figure 9B:
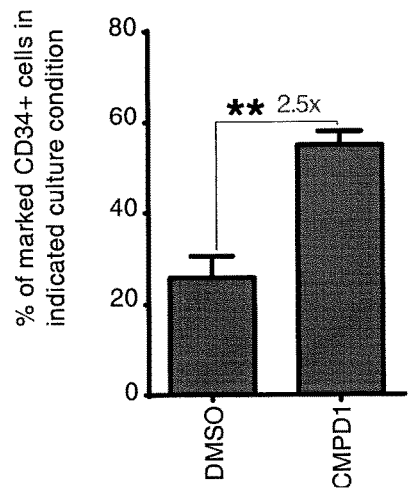

FIG. 9B shows the gene transfer efficiency to human CD34+ CB cells.

Figure 9C:
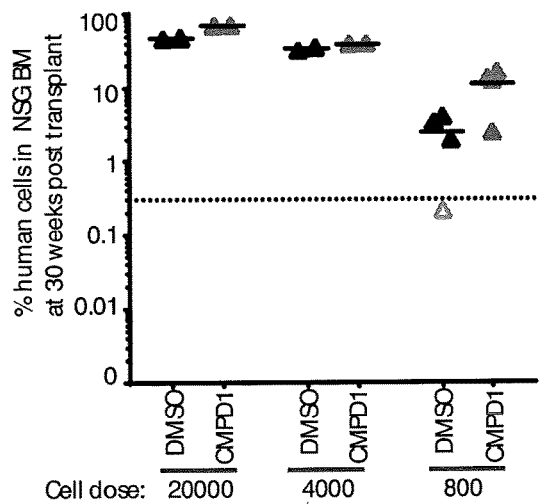

FIG. 9C shows human CD45+ cells in the mouse bone barrow at 30 weeks post-transplant with varying doses of cells (all presented as starting cell equivalents).

Figure 9D:
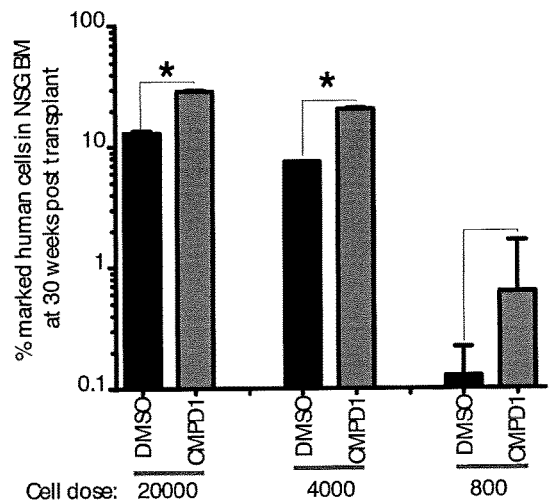

FIG. 9D shows the proportion of human cells expressing GFP in the bone marrow at 30 weeks post-transplant with varying doses of cells.

Figure 10A:
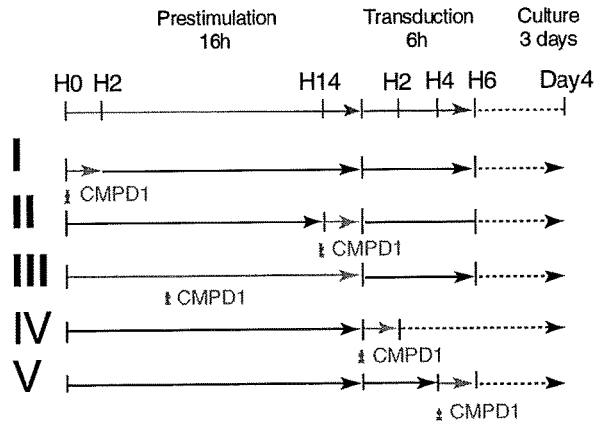

FIG. 10A shows the experimental design in which CD34+ CB cells were exposed to Cmpd1 for different durations during the prestimulation or transduction period. Minimum exposure time was 2 hrs at the beginning of the prestimulation period, or at the beginning or end of the transduction period.

Figure 10B:
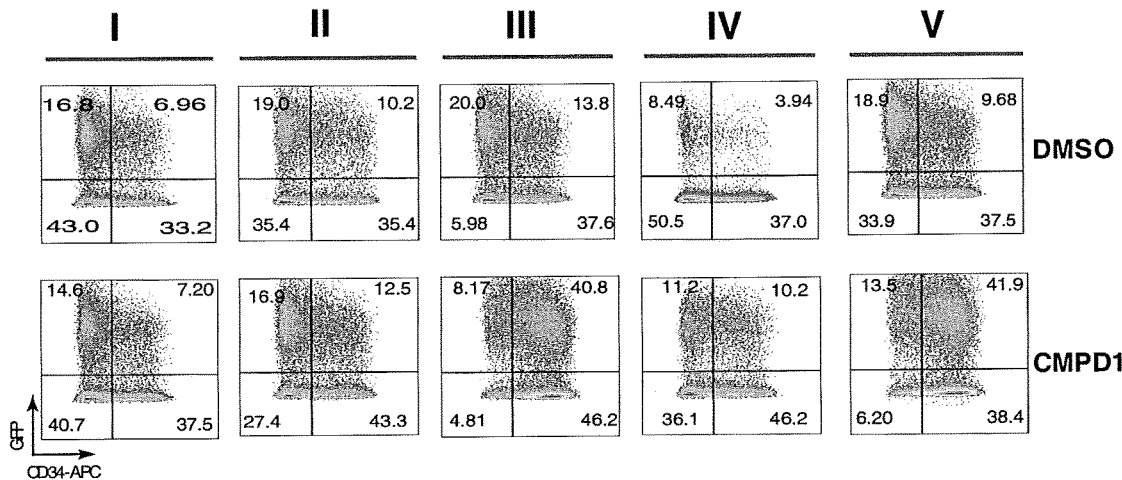

FIG. 10B shows a representative flow cytometry analysis of the cells recovered at the end of the 3-day expansion culture (in the absence of Cmpd1) to assess gene transfer to and yield of CD34+ cells under various conditions.

Figure 10C:
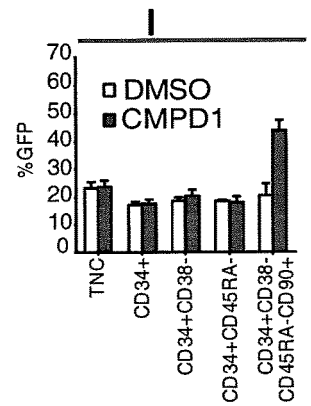
Figure 10D:
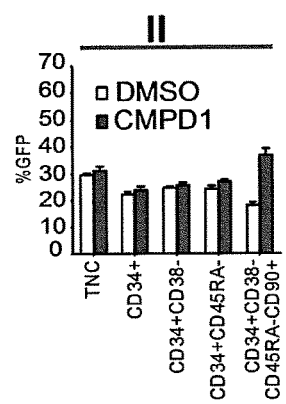
Figure 10E:
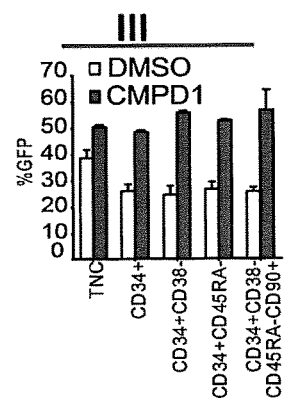
Figure 10F:
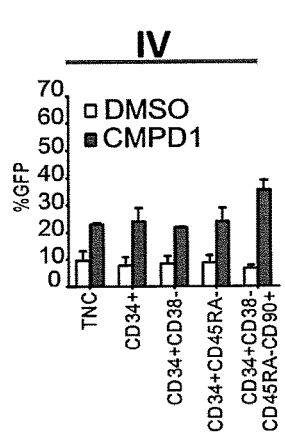
Figure 10G:
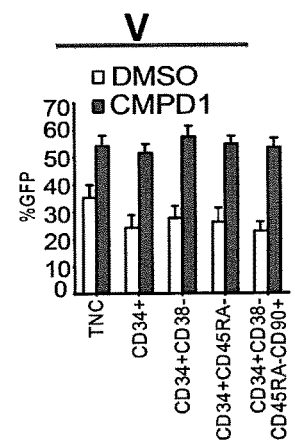
Figure 10H:
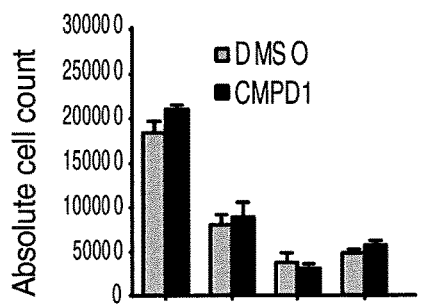
Figure 10I:
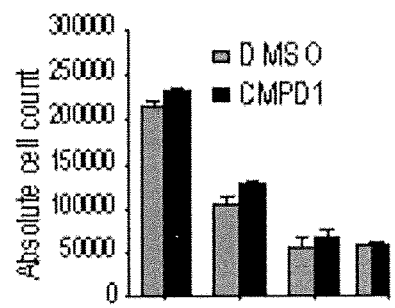
Figure 10M:
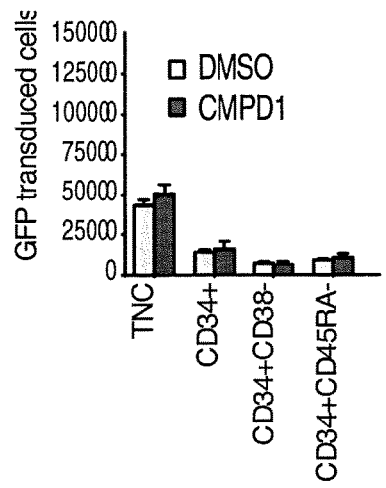
Figure 10N:
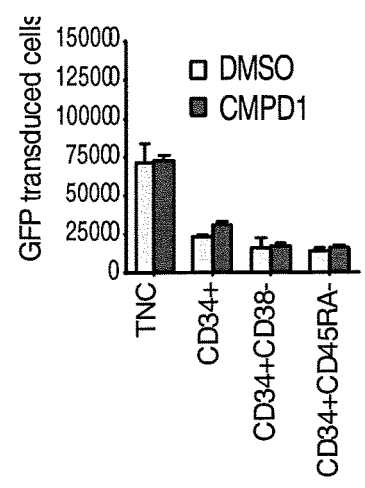
Figure 10J:
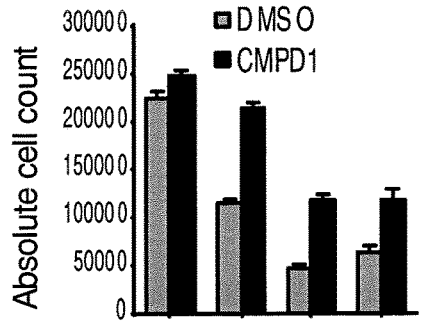
Figure 10K:
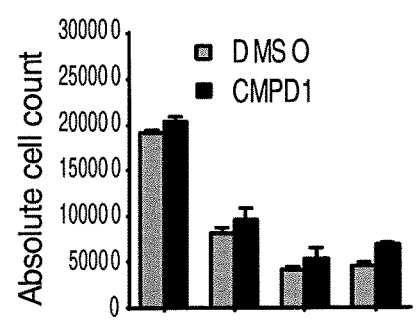
Figure 10O:
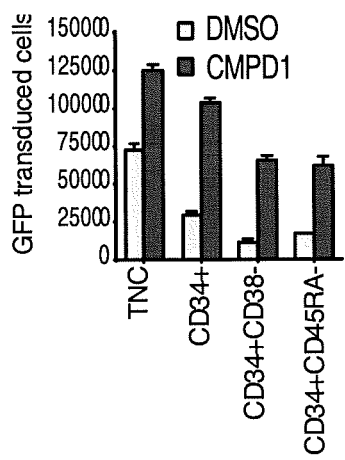
Figure 10P:
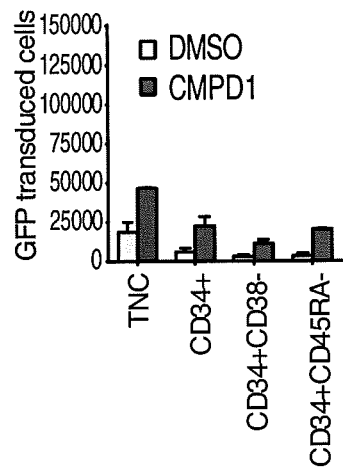
Figure 10L:
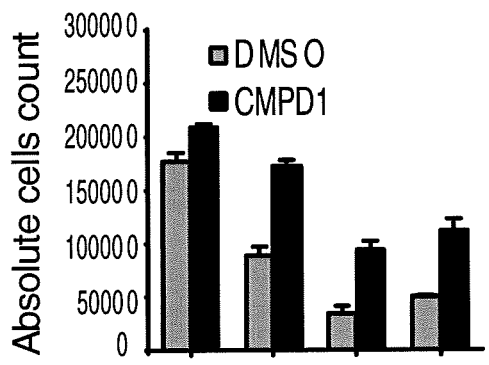
Figure 10Q:
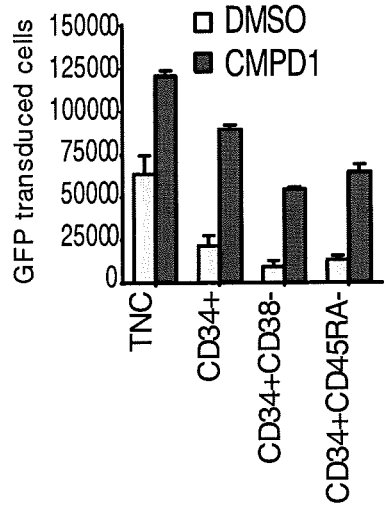

FIGS. 10C to 10P summarize gene transfer efficiencies and yields to various CD34+ subcompartments when Cmpd1 was present during the first 2 hours of prestimulation (FIGS. 10C, 10H and 10M), during the last 2 hours of prestimulation (FIGS. 10D, 10I and 10N), during the 16 hours of prestimulation (FIGS. 10E, 10J and 10O), during the first 2 hours of transduction (FIGS. 10F, 10K and 10P) or during the last 2 hours of transduction (FIGS. 10G, 10L and 10Q).

Figure 11A:
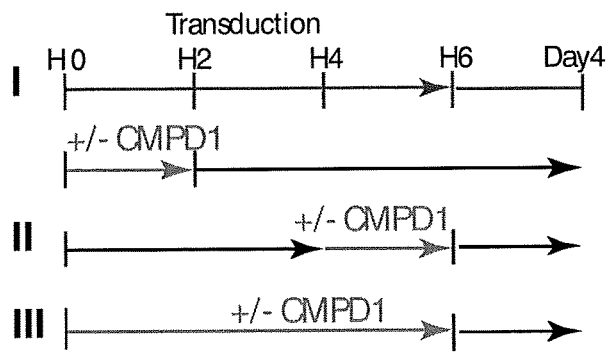

FIG. 11A shows the experimental design in which cells were directly exposed to virus without prior prestimulation in presence of absence of Cmpd1 for the durations indicated.

Figure 11B:
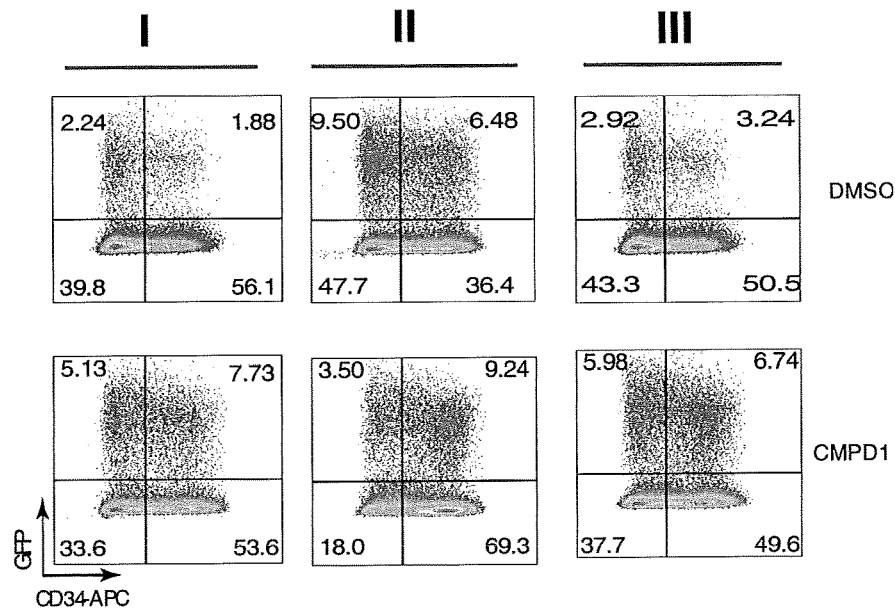
Figure 11C:
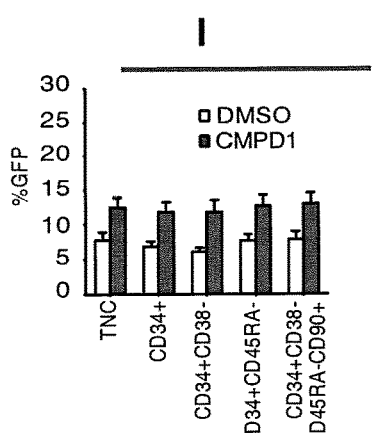
Figure 11D:
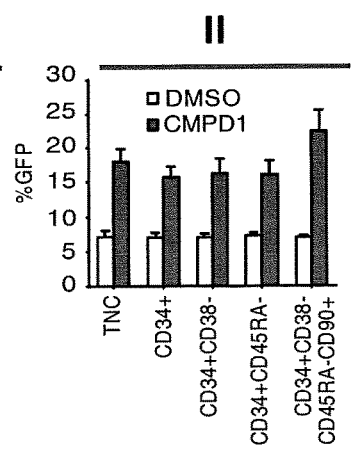
Figure 11E:
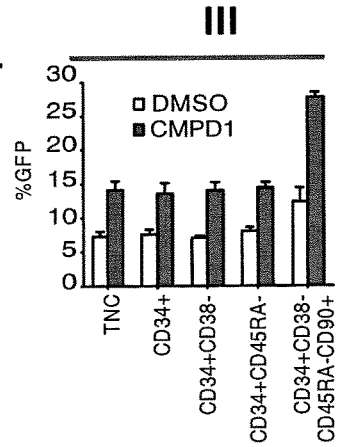
Figure 11F:
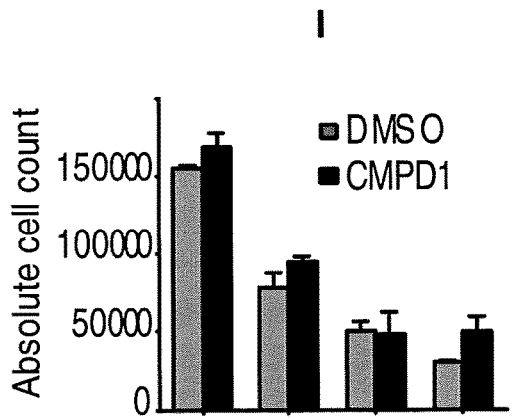
Figure 11G:
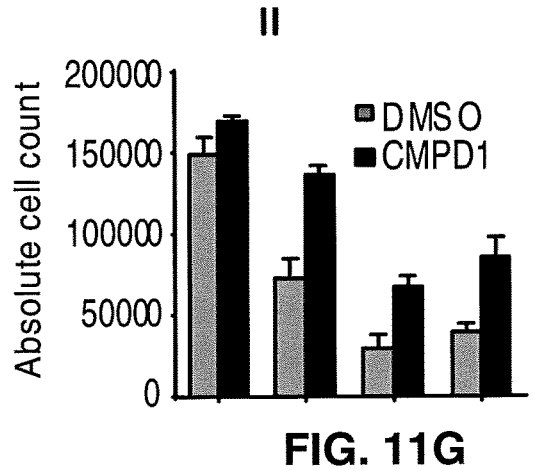
Figure 11I:
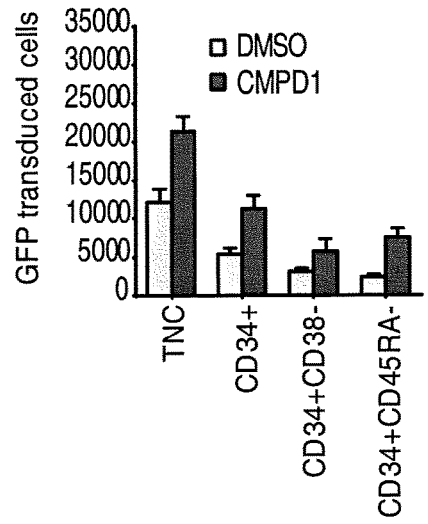
Figure 11J:
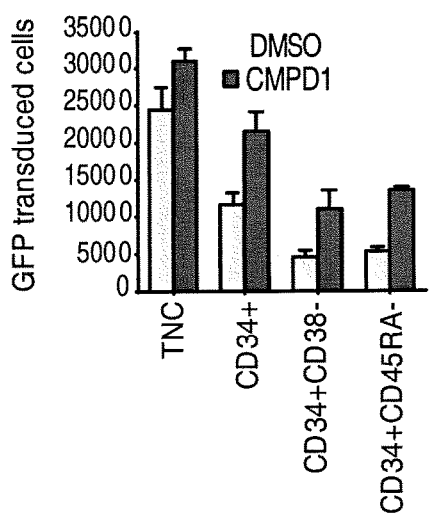
Figure 11H:
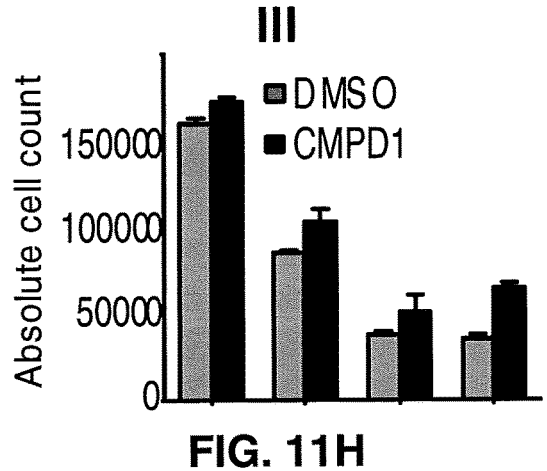
Figure 11K:
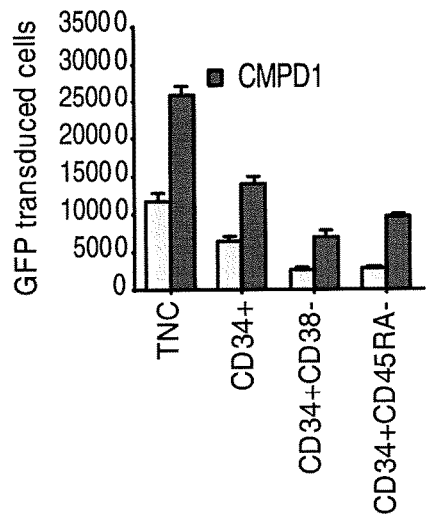

FIG. 11B shows representative flow cytometry analysis of the cells recovered at the end of the culture period. Subsequent panels summarize gene transfer and yields to CD34+ cells and CD34+ subpopulations under the various transduction conditions labelled I, II and III.

Figure 12A:
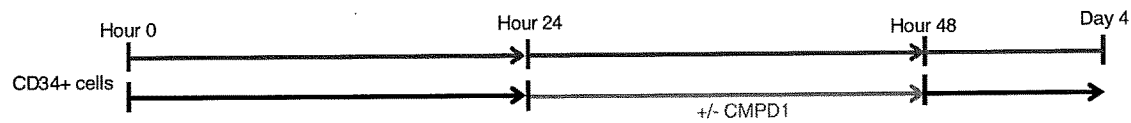

FIG. 12A shows the experimental design in which human Bone marrow CD34+ cells and Human CD34+ mobilized peripheral blood were prestimulated for 24 hours and transduced for 24 hours in a serum free medium supplemented with 100 ng/mL hSCF 100 ng/mL hFLT3-L, 100 ng/mL hTPO and 20 ng/mL hIL3 in presence of Cmpd1 (35 nM) or DMSO (0.01%). The cells were then washed and cultured for 3 additional days to assess the gene transfer efficiency and the yield of CD34+ cells and CD34+ subsets in the cultures.

Figure 12B:
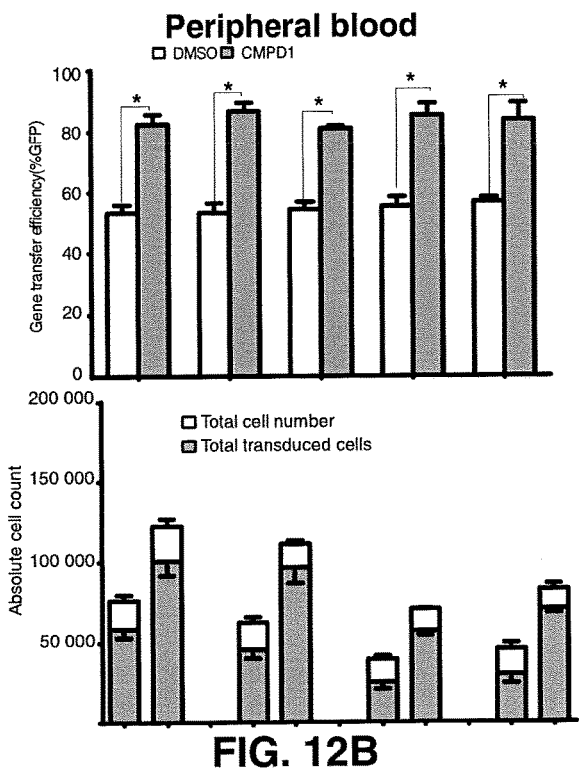
Figure 12C:
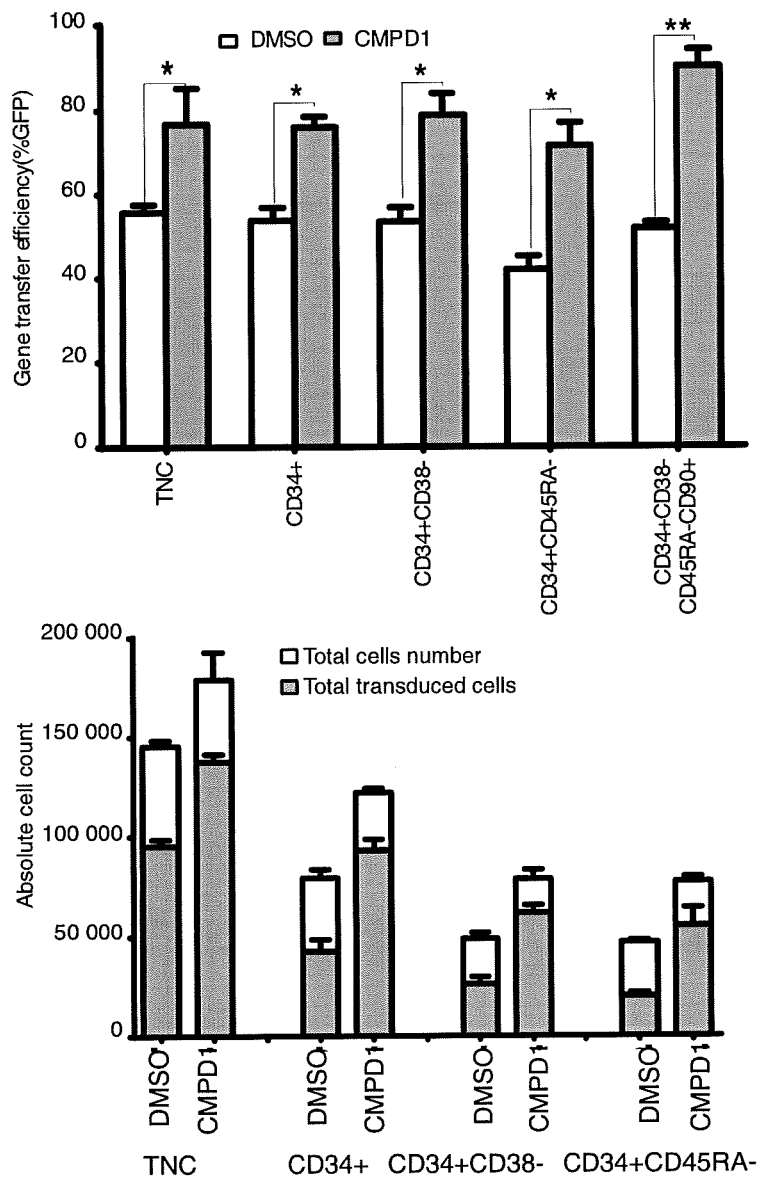

FIGS. 12B and 12C show the gene transfer efficiency and yields of transduced cells for different subsets of primitive human hematopoietic cells from bone marrow (FIG. 12B) and mobilized peripheral blood (FIG. 12C).

Figure 13A:
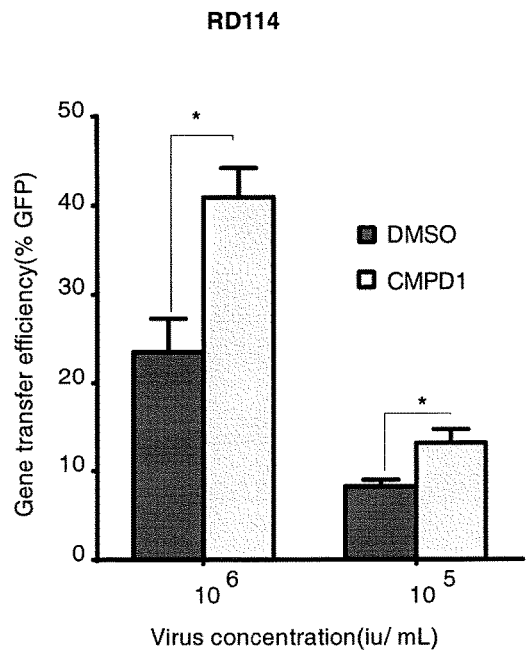

FIG. 13A shows the gene transfer efficiency to human CD34+ CB cells transduced using a RD114 pseudo-typed lentiviral vector.

Figure 13B:
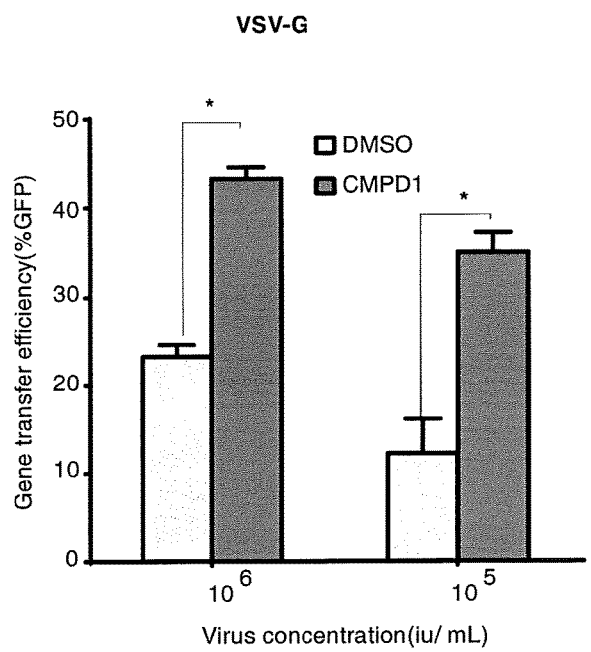

FIG. 13B shows the gene transfer efficiency to human CD34+ CB cells transduced using a VSV-G pseudo-typed lentiviral vector.

Figure 13C:
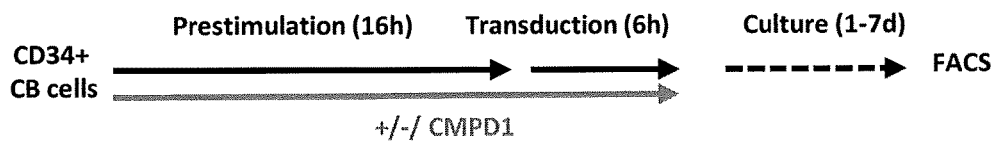

FIG. 13C shows the experimental design for testing the gene transfer efficiency to human CD34+ CB cells by a non-integrating (integrase defective) lentivirus.

Figure 13D:
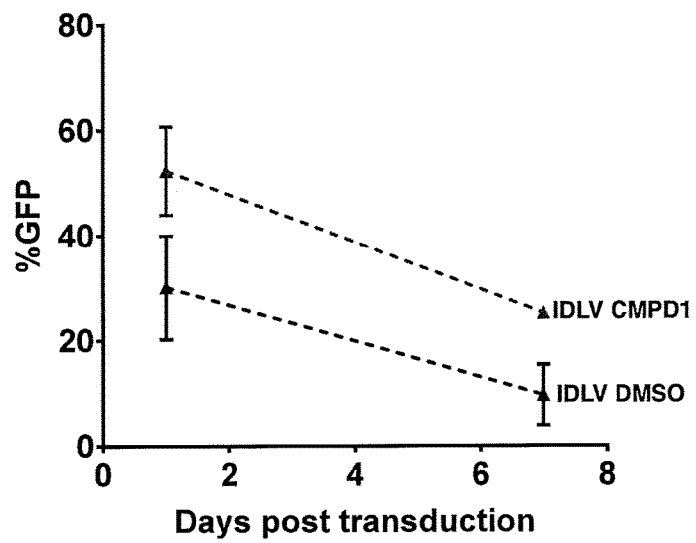

FIG. 13D shows the results of gene transfer to CD34+ cord blood cells in the presence or absence of CMPD1 using a non-integrating (integrase defective) lentivirus (panel B).

Figure 14A:
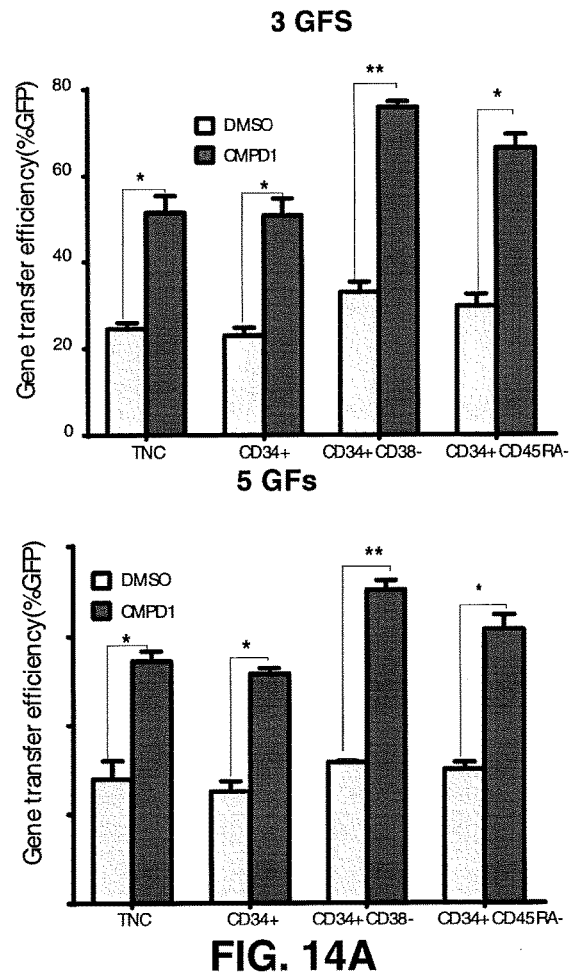
Figure 14B:
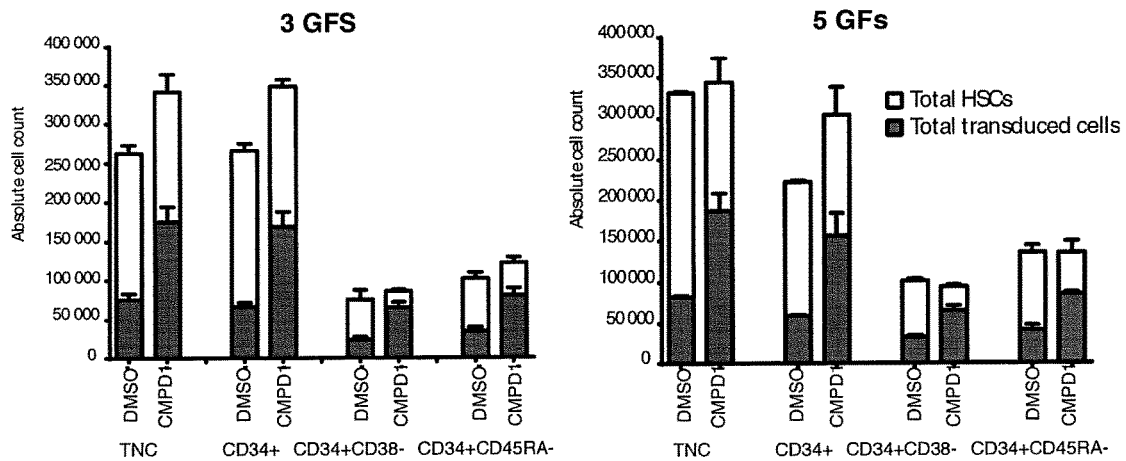
Figure 15A:
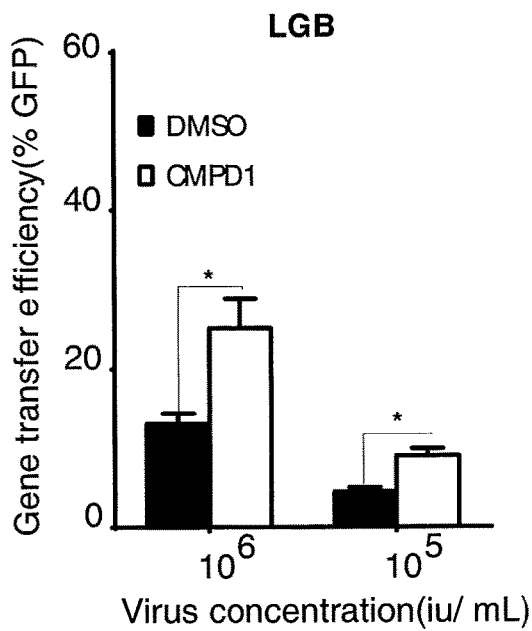
Figure 15B:
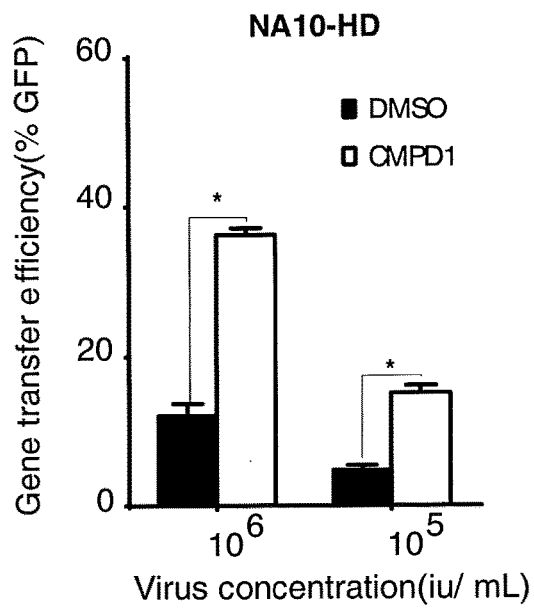
Figure 15C:
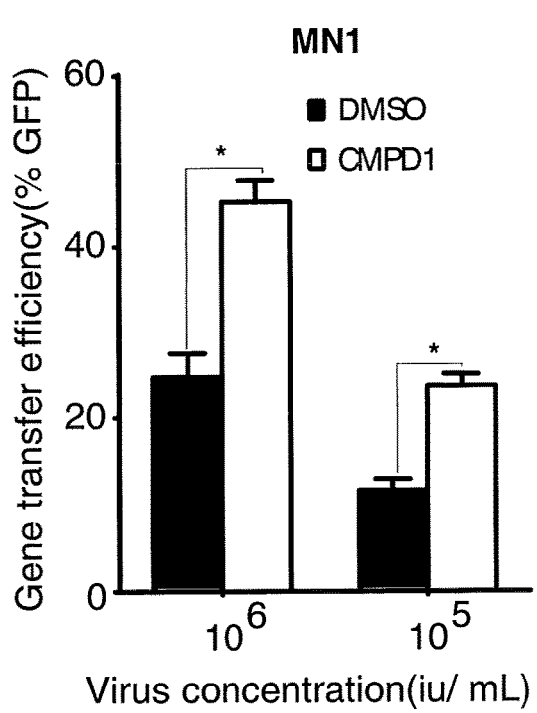
Figure 15D:
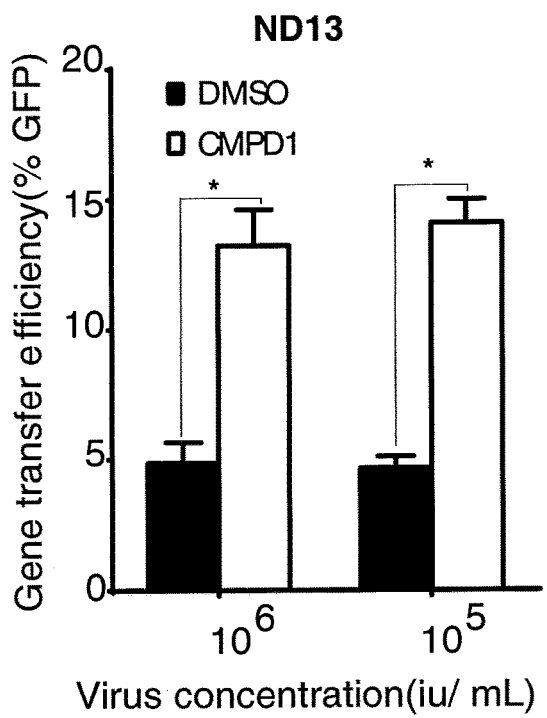

FIGS. 14A and 14B show the results of gene transfer experiments performed under different growth factor combinations. 20000 CD34+ CB cells were prestimulated and transduced in SFM under standard conditions employed in all previous experiments with 5 growth factors (100 ng/ml SCF, 100 ng/ml FLT3L, 20 ng/ml IL-3, 20 ng/ml IL-6 and 20 ng/ml G-CSF) or with a different cocktail of 3 growth factors (100 ng/ml SCF, 100 ng/ml FLT3L, 50 ng/mL TPO) supplemented with Cmpd1 (35 nM) or DMSO (0.01%). The cells were washed and cultured in the same media for 3 additional days to assess the gene transfer efficiency and yields for CD34+ cells and CD34+ subsets under 3 growth factor (3 GFS, left panels) versus 5 growth factor (5 GFS, right panels) conditions. FIG. 14A: Gene transfer efficiency (% GFP cells); FIG. 14B: Absolute cell count.

FIGS. 15A to 15D shows the results of gene transfer experiments performed using a spectrum of lentiviral vectors. Human CD34+ cells were prestimulated for 16 hours and transduced with different lentiviral vectors for 6 hours with or without Cmpd1 under standard conditions and gene transfer assessed to CD34+ cells after a further 72 hours. Lentiviral vectors carrying a range of different inserts (LGB, NA10-HD, MN1, ND13, FIGS. 15A to 15D, respectively) were generated and tested at the viral concentrations indicated.

Figure 16A:
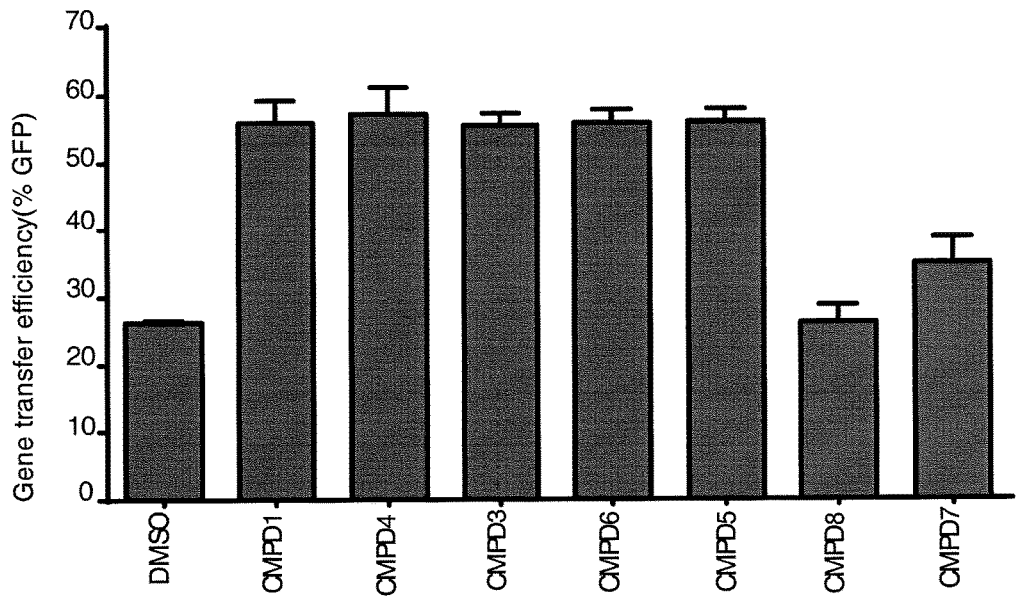
Figure 16B:
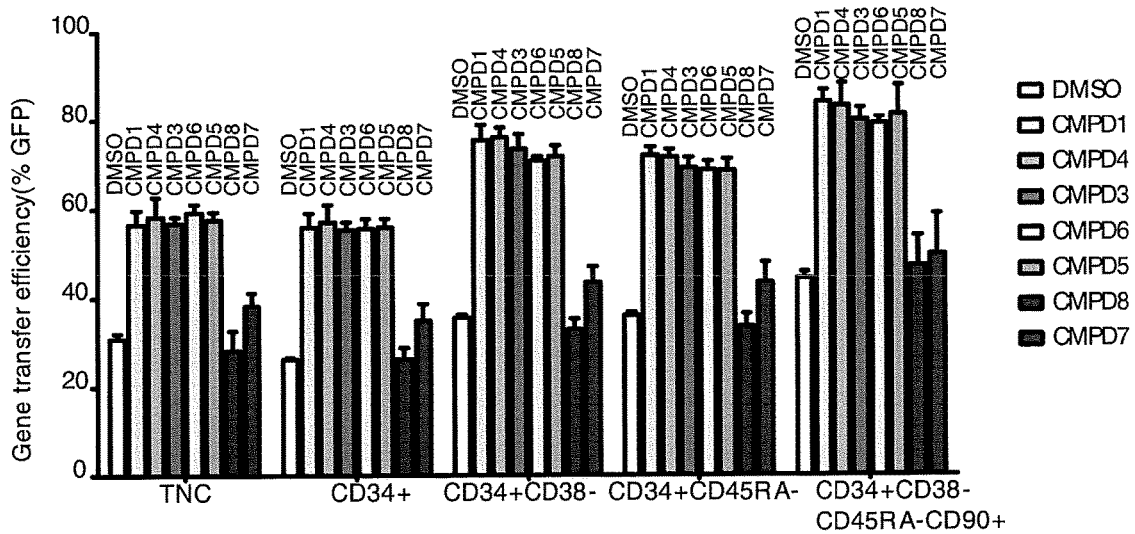

FIGS. 16A and 16B show the results of gene transfer experiments performed with variants of Cmpd1. Human CD34+ CB cells were prestimulated (16 hours) and transduced (6 hours) in presence of DMSO, Cmpd1 or different variants of Cmpd1. The cells were then washed and cultured for 3 additional days and analysed by FACS. Cmpd1 and other variants of Cmpd1 (Cmpd3, Cmpd4, Cmpd5, Cmpd6) known to be active for expansion of human CD34+ cells but not inactive variants of Cmpd1 (Cmpd7, Cmpd8) increase gene transfer efficiency to human CD34+ CB cells (FIG. 16A) and different CD34+ subsets (FIG. 16B).

Figure 17A:
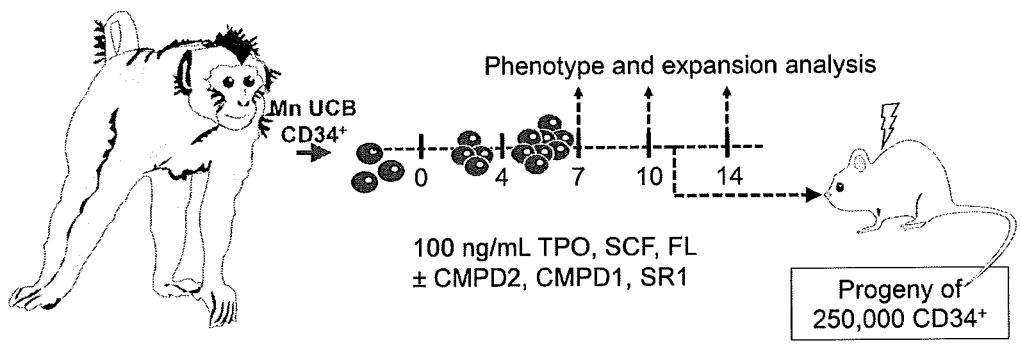
Figure 17B:
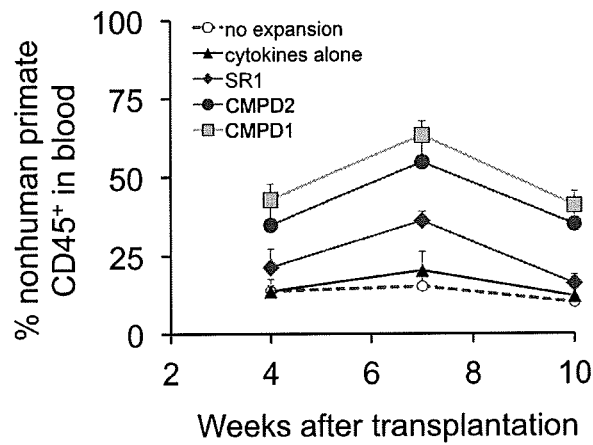
Figure 17C:
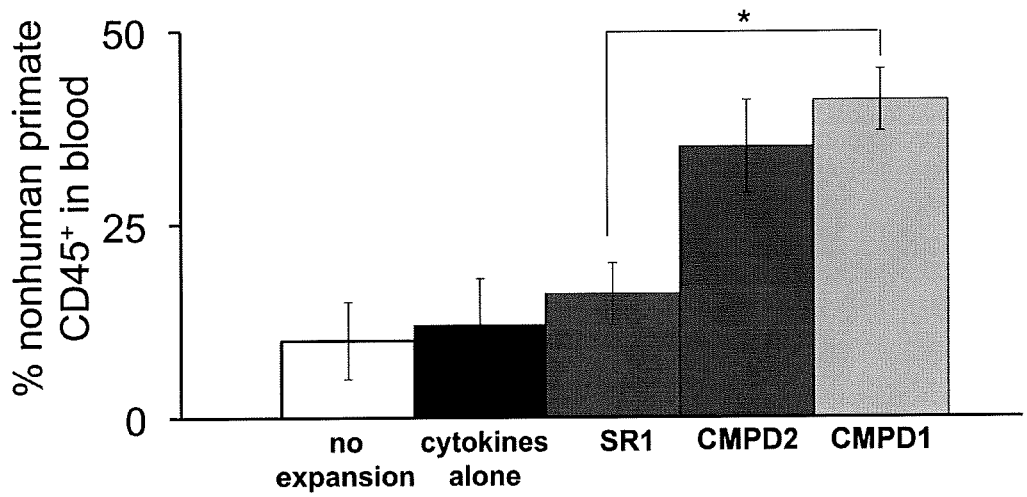
Figure 17D:
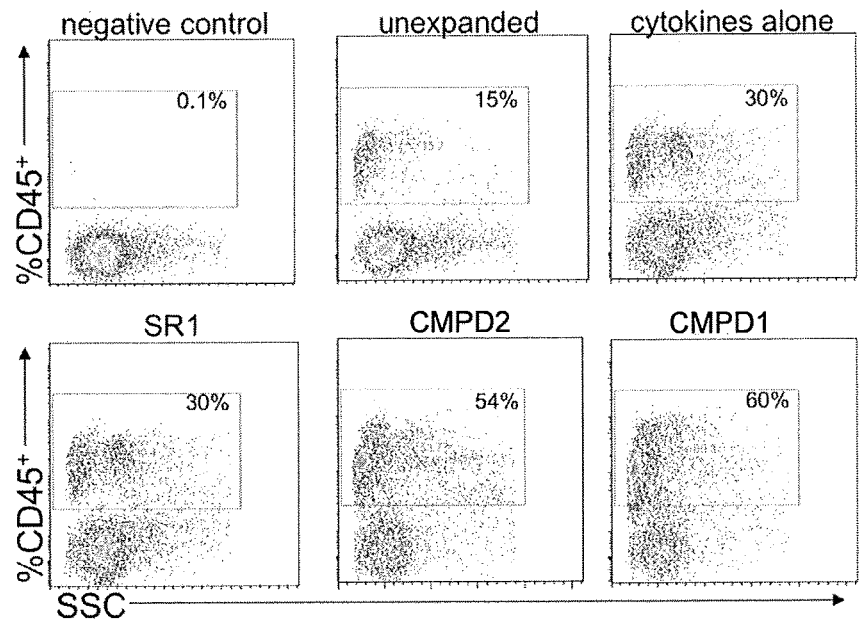

FIGS. 17A to 17C shows the expansion and engraftment of macaque umbilical cord blood CD34+ cells after co-culture±Cmpd1, Compound 2 (Cmpd2), and SR1. FIG. 17A: experimental schematic. FIG. 17B shows the detection of primate CD45+ cells in the blood of transplanted mice after transplantation. FIG. 17C shows the summary engraftment data at 10 weeks after transplantation (top panel) and a representative flow cytometry analysis (week 10) (bottom panel). Level of significance: *p<0.05.

Figure 18A:
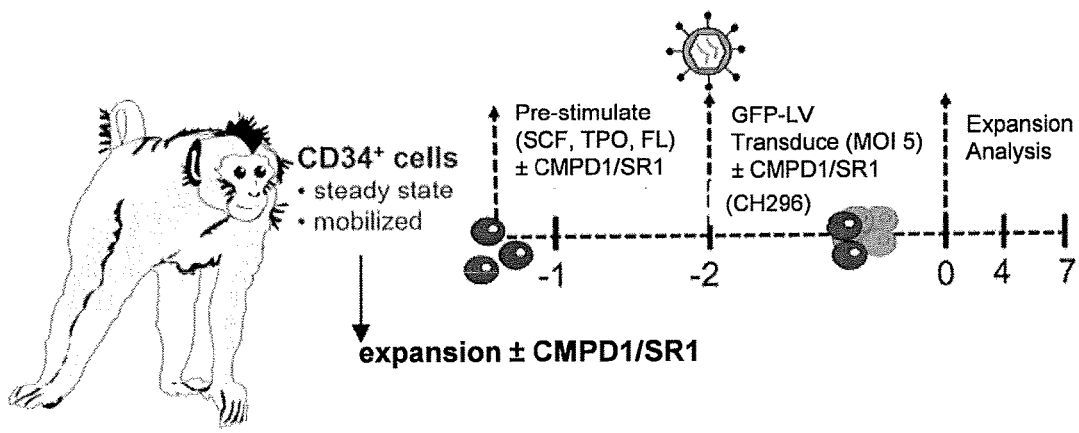
Figure 18B:
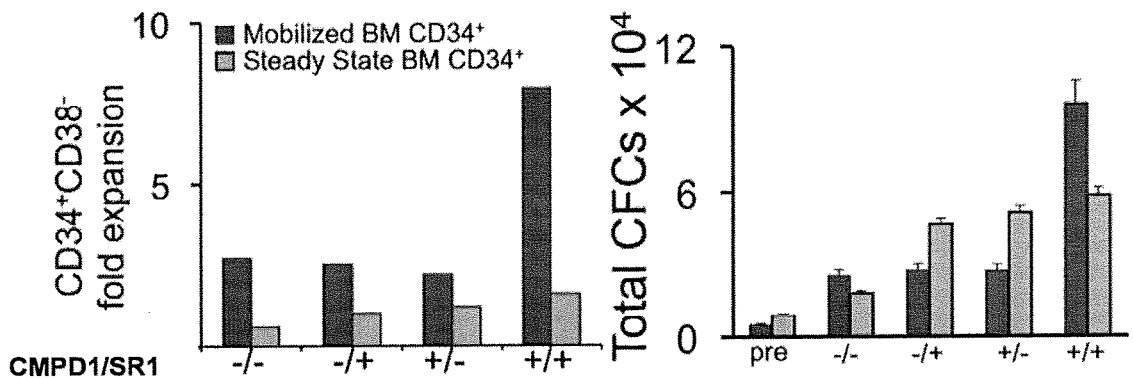
Figure 18G:
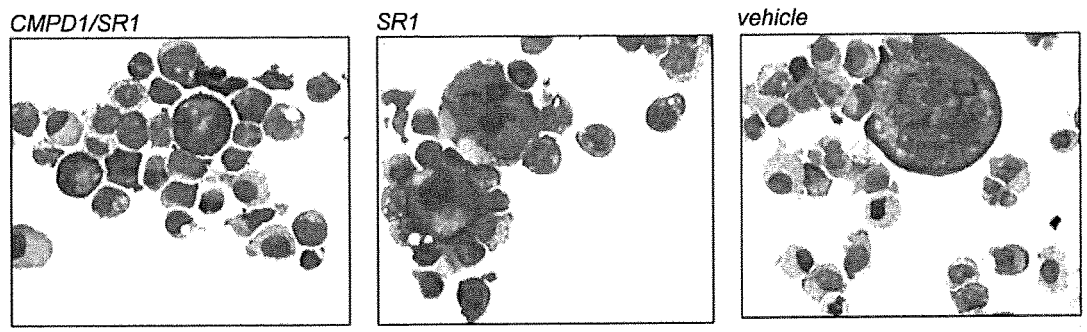

FIGS. 18A to 18G show the effect of Cmpd1 on the transduction and expansion of gene-modified CD34+ and LT-HSC like cells from macaque bone marrow. FIG. 18A: experimental schematic. FIG. 18B shows the expansion of CD34+ cells and CFC formation before and after expansion with Cmpd1/SR1. FIG. 18C shows the cell yield after transduction of CD34+ cells+/−Cmpd1. FIG. 18D shows the kinetics of gene-modified LT-HSC like cell expansion after transduction of mobilized marrow CD34+ cells 1 week after transduction. FIG. 18E shows the fold expansion of transduced cells+/−Cmpd1/SR1 (upper panel; left bars=total GFP+; middle bars=CD34$^+$ GFP$^+$; right bars=LT-HSC$^+$ GFP$^+$) and CFC potential of transduced mobilized bone marrow CD34+ cells after expansion+/−Cmpd1/SR1 (lower panel). FIG. 18F shows that the combination Cmpd1/SR1 maintains blasts during transduction of mobilized CD34+ cells compared to SR1. FIG. 18G shows a representative cytospin images for data shown in FIG. 18F.

Figure 19A:
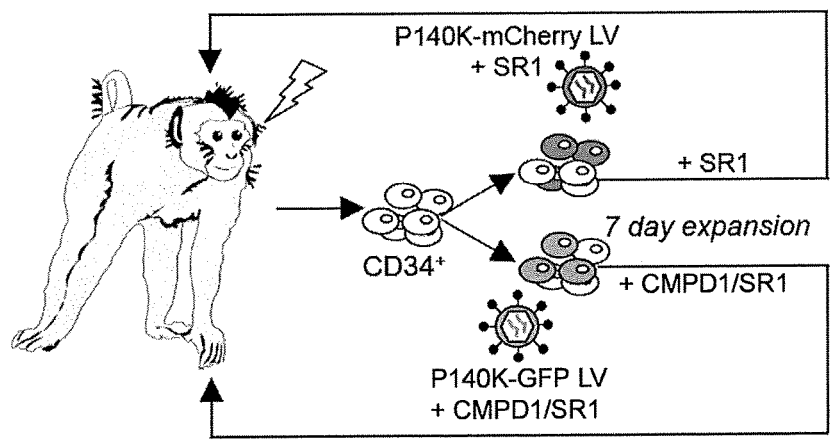
Figure 19B:
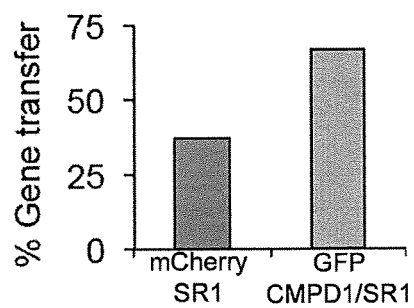
Figure 19C:
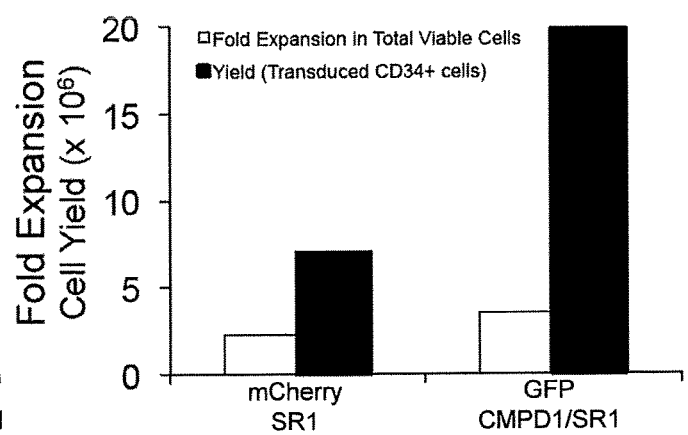
Figure 19D:
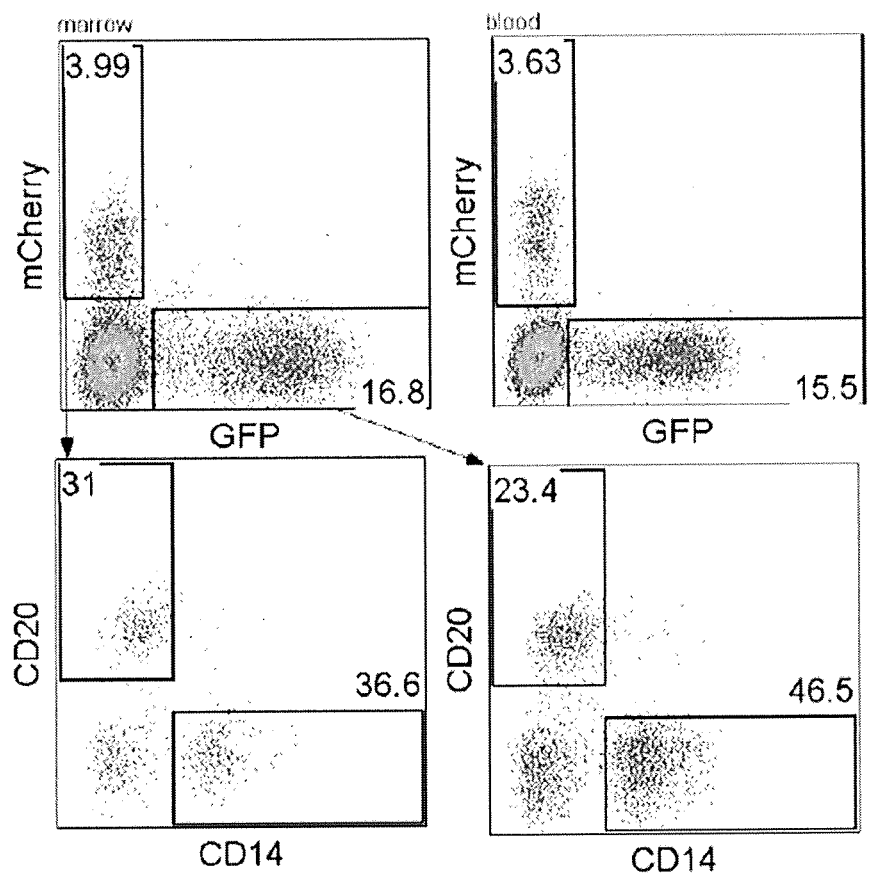
Figure 19E:
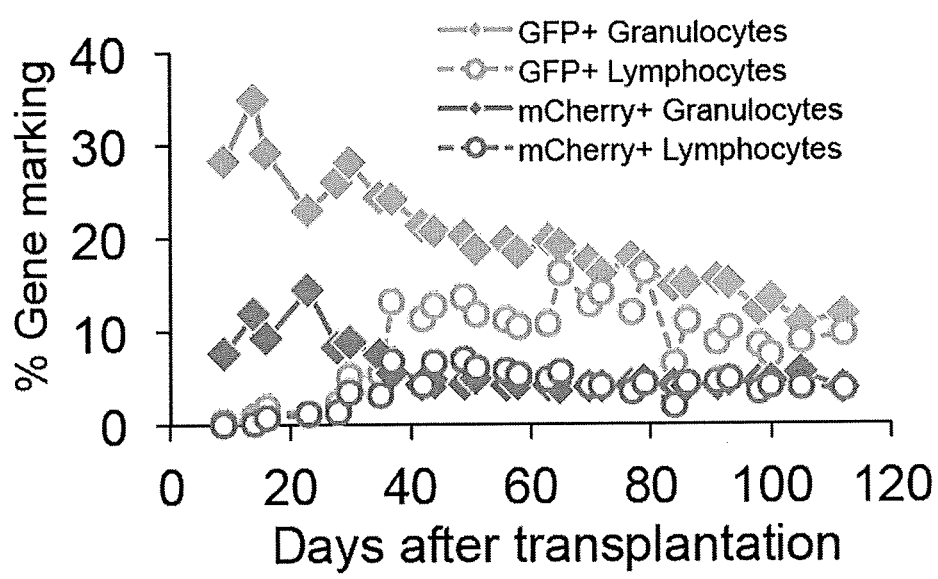

FIGS. 19A to 19E show the engraftment of SR1/Cmpd1 expanded transduced CD34+ cells in the macaque. FIG. 19A: experimental schematic. FIG. 19B shows the gene transfer in CD34+ cells transduced with SR1 (left bar) and SR1+Cmpd1 (right bar). FIG. 19C shows the fold expansion of gene-modified CD34+ cells after co-culture with SR1 (left bars) and SR1+Cmpd1 (right bars). FIG. 19D shows the detection of myeloid and lymphoid cells in marrow and blood 1 month after cell transplantation. FIG. 19E shows the detection of gene-modified granulocytes and lymphocytes after transplantation (GFP+ granulocytes=lighter gray lozenges; GFP+ lymphocytes=lighter gray circles; mCherry+ granulocytes=darker gray lozenges; mCherry+ lymphocytes=darker gray circles).

FIGS. 20A to E show the cooperation between Cmpd1 and Rapamycin to enhance lentiviral gene transfer efficiency to human hematopoietic cells.

Figure 20A:
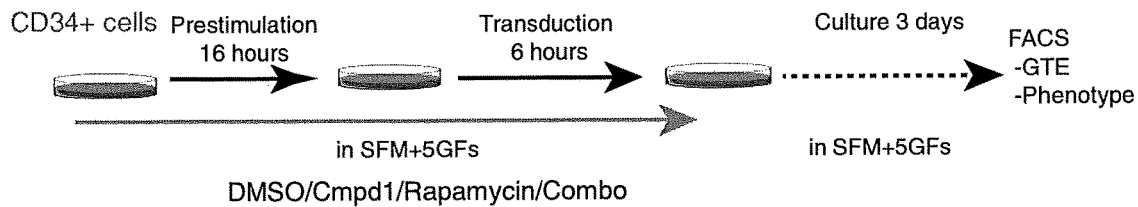

FIG. 20A shows a schematic of experimental design. 20,000 CD34+ cord blood cells isolated by FACS were pre-stimulated for 16 hours in 100 microliters of serum-free medium plus human growth factors (100 ng/ml SCF, 100 ng/ml FLT3L, 20 ng/ml IL-3, 20 ng/ml IL-6 and 20 ng/ml G-CSF) in the presence or absence of Cmpd1 (35 nM) and/or Rapamycin (10 µg/mL). The cells were then exposed for 6 hours to a GFP lentiviral vector ($10^6$ iu/mL) in the same medium. At the end of the transduction period, cells were washed and cultured for 72 hours in serum free medium with growth factors. At the end of the culture, cells were harvested, stained for HSCs surface markers and analysed by flow cytometry.

Figure 20B:
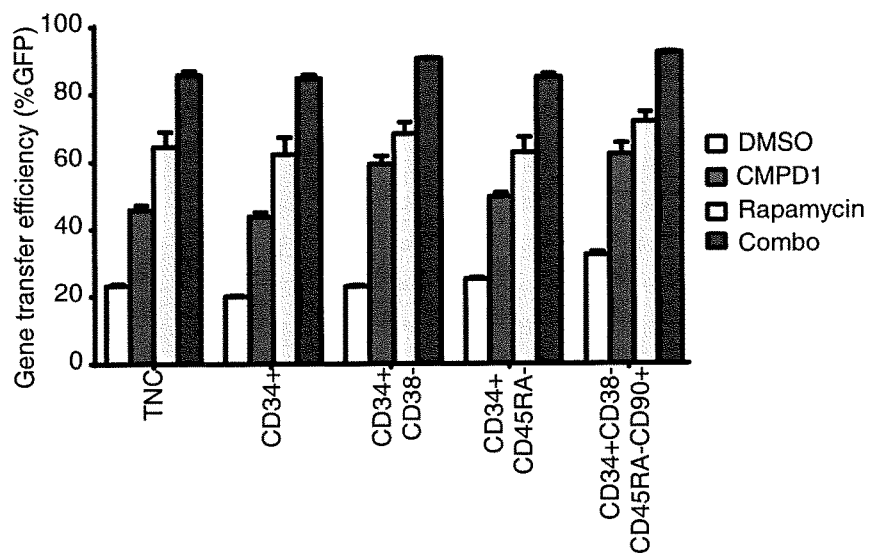

FIG. 20B shows the gene transfer efficiency into human HSCs. Left bars=DMSO; second bars=Cmpd1; third bars=rapamycin; fourth (right) bars=Cmpd1+rapamycin (Combo).

Figure 20C:
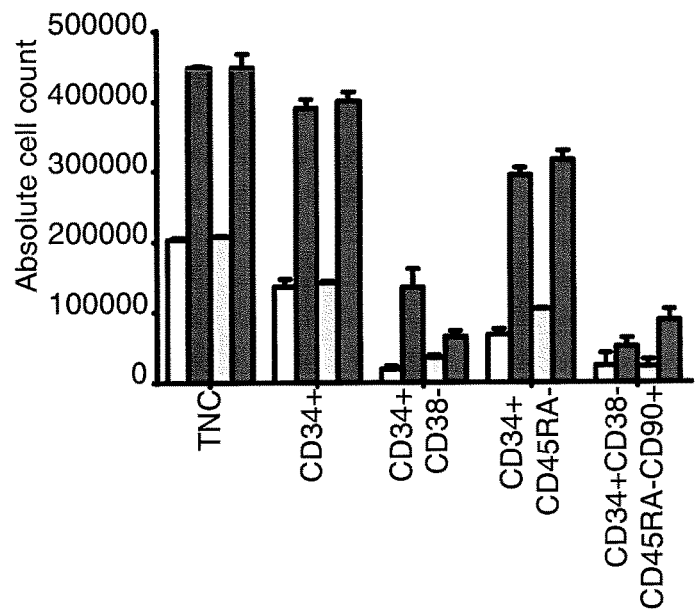

FIG. 20C shows the total cell number recovered at the end of the culture. Left bars=DMSO; second bars=Cmpd1; third bars=rapamycin; fourth (right) bars=Cmpd1+rapamycin (Combo).

Figure 20D:
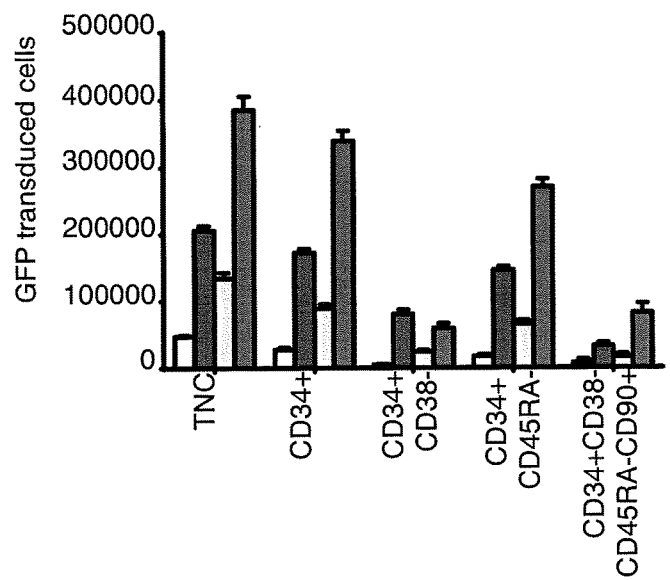

FIG. 20D shows the absolute number of HSCs yielded in the culture. Left bars=DMSO; second bars=Cmpd1; third bars=rapamycin; fourth (right) bars=Cmpd1+rapamycin (Combo).

Figure 20E:
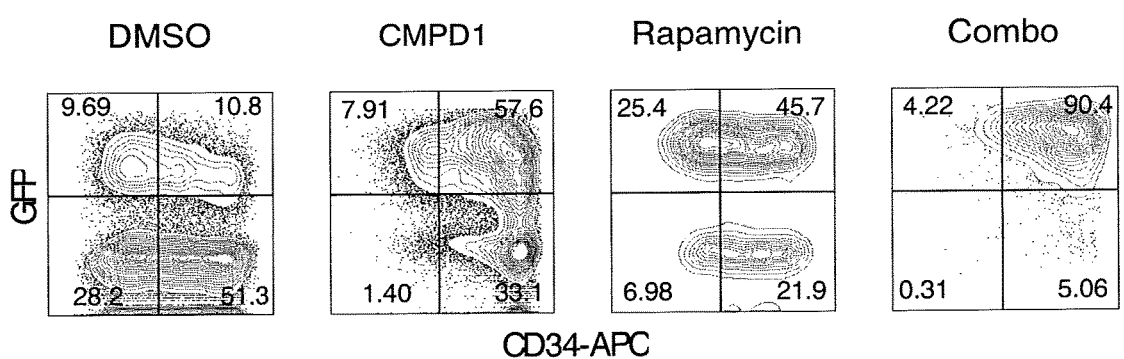

FIG. 20E shows the representative flow cytometric analysis of the cells recovered at the end of the culture.

DISCLOSURE OF INVENTION

In the studies described herein, the present inventors have shown that short-term exposure (e.g., about 2 to 22 hours) of human hematopoietic cells to certain pyrimido[4,5-b]indole derivatives, which have been shown to stimulate the expansion of human hematopoietic cells after extended culture (12 days), significantly enhances viral-mediated gene transfer. This capacity to enhance lentiviral-mediated gene transfer was not observed with StemRegenin 1 (SR1), another small molecule that is known to stimulate expansion of primitive human hematopoietic cells. This enhancement was measured in primitive hematopoietic cells of different sources (including cord blood, adult bone marrow and adult mobilized peripheral blood), and of different phenotypes (bulk CD34+ as well as highly purified CD34+ subsets that include those highly enriched for stem cells), and with different types of viral viruses (different lentiviruses, including an integration-defective lentivirus and different pseudotyped lentiviruses), indicating that these compounds may be broadly applicable to enhancement of viral gene transfer in cells, such as hematopoietic cells.

Accordingly, in a first aspect, the present invention provides a method for transducing a viral vector (e.g., a lentiviral vector) into cells (e.g., primary cells such as stem and/or progenitor cells), said method comprising contacting said cells with a compound of general formula I as defined herein; and transducing said cells with a viral vector,

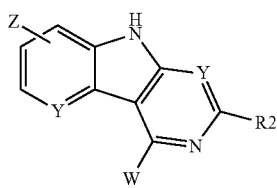

I or a salt or a prodrug thereof,
wherein:
each Y is independently selected from N and CH;
Z is —CN; —C(O)OR1; —C(O)N(R1)R3; —C(O)R1; or -heteroaryl optionally substituted with one or more RA or R4 substituents, wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is —CN; —N(R1)R3; —C(O)OR1; —C(O)N(R1)R3; —NR1C(O)R1; —NR1C(O)OR1; —OC(O)N(R1)R3; —OC(O)R1; —C(O)R1; —NR1C(O)N(R1)R3; —NR1S(O)$_2$R1; -benzyl optionally substituted with 1, 2 or 3 RA or R1 substituents; —X-L-(X-L)n; —N(R1)R3; —X-L-(X-L)n-heteroaryl optionally substituted with one or more RA or R4 substituents attached on either or both the L and heteroaryl groups; —X-L-(X-L)n-heterocyclyl optionally substituted with one or more RA or R4 substituents attached on either or both the L and heterocyclyl groups; —X-L-(X-L)n-aryl optionally substituted with one or more RA or R4 substituents; —X-L-(X-L)$_n$-NR1RA or —(N(R1)-L)$_n$-N$^+$R1R3R5R6$^-$, wherein n is an integer equal to either 0, 1, 2, 3, 4, or 5,
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from O, S, and NR1;
L is each independently —C$_{1-6}$ alkylene; —C$_{2-6}$ alkenylene; —C$_{2-6}$ alkynylene; —C3-7 cycloalkylene, which optionally includes one or more other heteroatom selected from N, O and S; or —C3-7 cycloalkenylene, which optionally includes one or more other heteroatom selected from N, O and S, wherein the alkylene, the alkenylene, the alkynylene, the cycloalkylene and the cycloalkenylene groups are each independently optionally substituted with one or two R4 or RA substituent;
R1 is each independently —H; —C$_{1-6}$ alkyl; —C$_{2-6}$ alkenyl; —C$_{2-6}$ alkynyl; —C$_{3-7}$ cycloalkyl; —C$_{3-7}$ cycloalkenyl; —C$_{1-5}$ perfluorinated; -heterocyclyl; -aryl; -heteroaryl; or -benzyl, wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is —H; —C$_{1-6}$ alkyl, optionally substituted with one more RA substituents; —C(O)R4; -L-heteroaryl optionally substituted with one or more RA or R4 substituents; -L-heterocyclyl optionally substituted with one or more RA or R4; or -L-aryl optionally substituted with one or more RA or R4 substituents;
R3 is each independently —H; —C$_{1-6}$ alkyl; —C$_{2-6}$ alkenyl; —C$_{2-6}$ alkynyl; —C$_{3-7}$ cycloalkyl; —C$_{3-7}$ cycloalkenyl; —C$_{1-5}$ perfluorinated; -heterocyclyl; -aryl; -heteroaryl; or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R4 is each independently —H; —C$_{1-6}$ alkyl; —C$_{2-6}$ alkenyl; —C$_{2-6}$ alkynyl; —C$_{3-7}$ cycloalkyl; —C$_{3-7}$ cycloalkenyl; —C$_{1-5}$ perfluorinated; -heterocyclyl; -aryl; -heteroaryl, or -benzyl; wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R5 is each independently —C$_{1-6}$ alkyl; —C$_{1-6}$ alkylene-C$_{2-6}$ alkenyl which optionally includes one or more other heteroatom selected from N, O and S; —C$_{1-6}$ alkylene-C$_{2-6}$ alkynyl which optionally includes one or more other heteroatom selected from N, O and S; -L-aryl which optionally includes one or more RA or R4 substituents; -L-heteroaryl which optionally includes one or more RA or R4 substituents; —C$_{1-6}$ alkylene-C(O)O—; —C$_{1-6}$ alkylene-C(O)OR1; —C$_{1-6}$ alkylene-CN; —C$_{1-6}$ alkylene-C(O)NR1R3, wherein R1 and R3 optionally they join together with the nitrogen atom to form a 3 to 7-membered ring which optionally includes one or more other heteroatom selected from N, O and S; or —C$_{1-6}$ alkylene-OH;

R6 is halogen; —OC(O)CF$_3$; or —OC(O)R1;

RA is each independently -halogen; —CF$_3$; —OR1; -L-OR1; —OCF$_3$; —SR1; —CN; —NO$_2$; —NR1R3; -L-NR1R1; —C(O)OR1; —S(O)$_2$R4; —C(O)N(R1)R3; —NR1C(O)R1; —NR1C(O)OR1; —OC(O)N(R1)R3; —OC(O)R1; —C(O)R4; —NHC(O)N(R1)R3; —NR1C(O)N(R1)R3; or —N$_3$; and Rd is each independently —H; —C$_{1-6}$ alkyl; —C$_{2-6}$ alkenyl; —C$_{2-6}$ alkynyl; —C$_{3-7}$ cycloalkyl; —C$_{3-7}$ cycloalkenyl; —C$_{1-5}$ perfluorinated; -benzyl; or -heterocyclyl.

In accordance with an embodiment, the compound is of formula IA

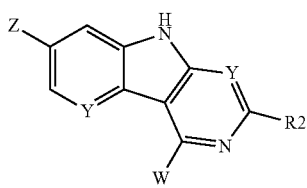

IA or a salt or a prodrug thereof,
wherein W, Y, Z and R2 are each as defined herein.

In accordance with an embodiment, the compound is of formula I or IA wherein
each Y is independently selected from N and CH;
Z is —CN, —C(O)OR1, —C(O)N(R1)R3, or -heteroaryl optionally substituted with one or more RA or R4 substituents,
W is —CN, —N(R1)R3, -benzyl optionally substituted with 1, 2 or 3 RA or R1 substituents, —X-L-(X-L)n-N(R1)R3, —X-L-(X-L)$_n$-NR1RA or —(N(R1)-L)$_n$-N$^+$R1R3R5R6$^-$
wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
X is each independently O, S, or NR1,
L is each independently —C$_{1-6}$ alkylene, —C$_{2-6}$ alkenylene, —C$_{2-6}$ alkynylene, —C3-7 cycloalkylene, which optionally includes one or more other heteroatom selected from N, O and S or —C3-7 cycloalkenylene, which optionally includes one or more other heteroatom selected from N, O and S wherein the alkylene, the alkenylene, the alkynylene the cycloalkylene and the cycloalkenylene are each independently optionally substituted with one or two R4 or RA substituent;
R1 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is —H, —C$_{1-6}$ alkyl, optionally substituted with one more RA substituents, —C(O)R4, -L-heterocyclyl optionally substituted with one or more RA or R4 substituents, -L-heterocyclyl optionally substituted with one or more RA or R4, or -L-aryl optionally substituted with one or more RA or R4 substituents;

R3 is each independently —H, —C$_{1-6}$ alkyl, —C$_{2-6}$ alkenyl, —C$_{2-6}$ alkynyl, or —C$_{1-5}$ perfluorinated,
wherein the alkyl, the alkenyl, the alkynyl, the perfluorinated alkyl groups are each independently optionally substituted with 1, 2 or 3 RA or Rd substituents;
R4 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -aryl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R5 is each independently —C$_{1-6}$ alkyl, -L-aryl which optionally includes one or more RA or R4 substituents, -L-heteroaryl which optionally includes one or more RA or R4 substituents, —C$_{1-6}$ alkylene-C(O)O—, —C$_{1-6}$ alkylene-C(O)OR1, —C$_{1-6}$ alkylene-CN, —C$_{1-6}$ alkylene-C(O)NR1R3, or —C$_{1-6}$ alkylene-OH;
R6 is Halogen, OC(O)CF$_3$ or OC(O)R1;
RA is each independently -halogen, —CF$_3$, —OR1, -L-OR1, —OCF$_3$, —SR1, —CN, —NO$_2$, NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$;
Rd is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -benzyl or -heterocyclyl.

In accordance with another embodiment, the compound is of formula IIA

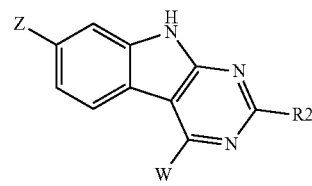

IIA or a salt or a prodrug thereof,
wherein Z, W and R2 are each as defined herein.

In accordance with one embodiment, the compound is of formula I, IA or IIA
Z is —CN; —C(O)O—C$_{1-6}$ alkyl; —C(O)NH—C$_{1-6}$ alkyl; or -heteroaryl optionally substituted with one or more RA or R4 substituents,
W is —N(R1)R3; —NR1-C$_{1-6}$ alkylene-N(R1)R3; —O—C$_{1-6}$ alkylene-N(R1)R3; —S—C$_{1-6}$ alkylene-N(R1)R3; —NR1-C$_{1-6}$ alkylene-NR1RA; —NR1-C$_{1-6}$ alkylene-(NR1-C$_{1-6}$ alkylene)$_n$-NR1R3; or —NR1-C$_{1-6}$ alkylene-(NR1-C$_{1-6}$ alkylene)$_n$-NR1RA
wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
R1 is each independently —H; —C$_{1-6}$ alkyl; —C$_{2-6}$ alkenyl; —C$_{2-6}$ alkynyl; —C$_{3-7}$ cycloalkyl; —C$_{3-7}$ cycloalkenyl; —C$_{1-5}$ perfluorinated; -heterocyclyl; -heteroaryl; or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is —H; —$C_{1-6}$ alkyl; —C(O)R4; —$C_{1-6}$ alkylene-heteroaryl optionally substituted with one or more RA or R4 substituents either on the alkylene or the heteroaryl; —$C_{1-6}$ alkylene-heterocyclyl optionally substituted with one or more RA or R4; or —$C_{1-6}$ alkylene-aryl optionally substituted with one or more RA or R4 substituents either on the alkylene or the heteroaryl R3 is each independently —H; —$C_{1-6}$ alkyl; —$C_{2-6}$ alkenyl; —$C_{2-6}$ alkynyl; or —$C_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -heterocyclyl; -aryl; -heteroaryl; or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

RA is each independently -halogen, —$CF_3$; —OR1; -L-OR1; —$OCF_3$; —SR1; —CN; —$NO_2$; —NR1R3; -L-NR1R1; —C(O)OR1; $S(O)_2R4$; —C(O)N(R1)R3, —NR1C(O)R1, —NR1C(O)OR1, —OC(O)N(R1)R3, —OC(O)R1; —C(O)R4; —NHC(O)N(R1)R3; —NR1C(O)N(R1)R3; or —$N_3$ Rd is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -benzyl; or -heterocyclyl.

In accordance with another embodiment, the present disclosure provides a method for enhancing lentiviral gene transfer efficacy to primitive hematopoietic cells, said method comprising contacting a population of cells comprising primitive hematopoietic cells with a compound of general formulas I-VI; and transducing said cells with a lentiviral vector, the compound is of formula I, IA or IIA Z is CN, —C(O)O—$C_{1-6}$ alkyl, —C(O)NH—$C_{1-6}$ alkyl, or -heteroaryl optionally substituted with one or more RA or R4 substituents, W is —N(R1)R3, —NR1-$C_{1-6}$ alkylene-N(R1)R3, —O—$C_{1-6}$ alkylene-N(R1)R3, —S—$C_{1-6}$ alkylene-N(R1)R3, —NR1-$C_{1-6}$ alkylene-NR1RA, —NR1-$C_{1-6}$ alkylene-(NR1-$C_{1-6}$ alkylene)$_n$-NR1R3 or —NR1-$C_{1-6}$ alkylene-(NR1-$C_{1-6}$ alkylene)$_n$-NR1RA wherein n is an integer equal to either 0, 1, 2, or 3 and wherein, when R1 and R3 are attached to a nitrogen atom, optionally they join together with the nitrogen atom to form a 3 to 7-membered ring which optionally includes one or more other heteroatom (N, O or S), optionally the ring is substituted with one or more RA or R4;

R1 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is —H, —$C_{1-6}$ alkyl, —C(O)R4, —$C_{1-6}$ alkylene-heteroaryl optionally substituted with one or more RA or R4 substituents either on the alkylene or the heteroaryl, —$C_{1-6}$ alkylene-heterocyclyl optionally substituted with one or more RA or R4, or —$C_{1-6}$ alkylene-aryl optionally substituted with one or more RA or R4 substituents either on the alkylene or the heteroaryl;

R3 is each independently —H, —C16 alkyl, —$C_{2-6}$ alkenyl, —$C_{2-6}$ alkynyl, or —$C_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

RA is each independently -halogen, —$CF_3$, —OR1, -L-OR1, —$OCF_3$, —SR1, —CN, —$NO_2$, —NR1R3, -L-NR1R1, —C(O)OR1, $S(O)_2R4$, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —$N_3$ Rd is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -benzyl or -heterocyclyl.

In one embodiment, Z is —C(O)OR1, or -heteroaryl optionally substituted with one or more RA or R1 substituents, R2 is H, —$C_{1-6}$ alkyl optionally substituted with one or more RA substituents or -L-aryl optionally substituted with one or more RA or R4 substituents, W is —N(R1)R3 wherein R1 is C3-7 cycloalkyl substituted by RA and R3 is H.

In one embodiment, Z is —C(O)O—C1-4 alkyl or 5-membered ring heteroaryl, said heteroaryl comprising 2-4 heteroatoms (N or O), R2 is H, or -L-aryl optionally substituted by halogen, OR1, $C_{1-6}$ alkyl optionally substituted by RA, C(O)R4, -heterocyclyl, C(O)OR4 OR $C_{2-6}$alkynyl, W is —N(R1)R3 wherein R1 is cyclohexyl substituted by RA, and R3 is H.

In one embodiment, Z is COOMe, COOEt, tetrazole or oxadiazole.

In one embodiment, R2 is =H, or —CH2-aryl optionally substituted by substituted by halogen, OR1, $C_{1-6}$ alkyl optionally substituted by RA, C(O)R4, -heterocyclyl, C(O)OR4 OR $C_{2-6}$alkynyl, wherein said aryl is phenyl.

In one embodiment, R2 is H, —$C_{1-6}$ alkylene-heteroaryl or —$C_{1-6}$ alkylene-aryl, optionally substituted with one or more RA or R4 substituents.

In accordance with another embodiment, the compound is of Formula I, IA or IIA wherein Z is $CO_2Me$ or 2-methyl-2H-tetrazol-5-yl;

R2 is benzyl, or H; and

W is NH-L-N(R1)R3 wherein L is C2-4 alkylene or C3-7 cycloalkylene and R1 and R3 is C1-4 alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

In accordance with another embodiment, the compound is of Formula I, IA or IIA wherein W is

23
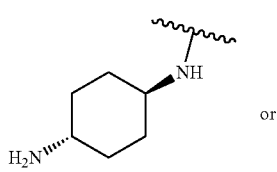 or
24
-continued
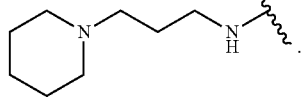
In a further embodiment, the compound is
(compound 2)
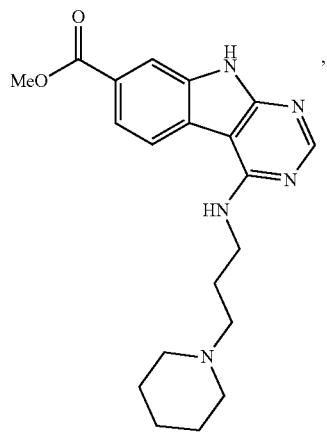,
(compound 4)
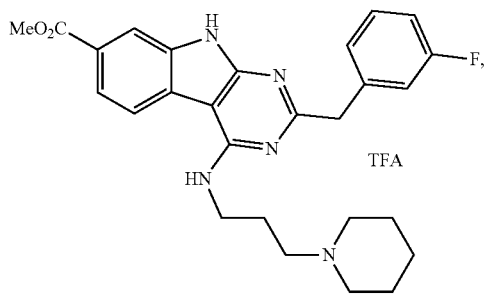
(compound 1)
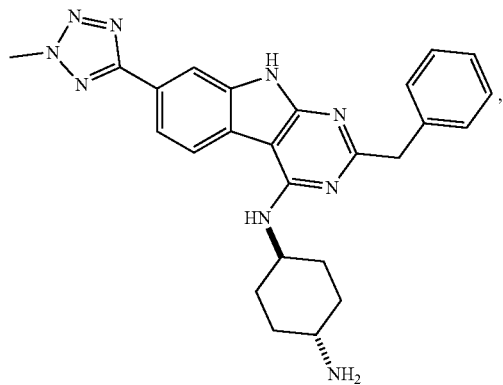,
(compound 3)
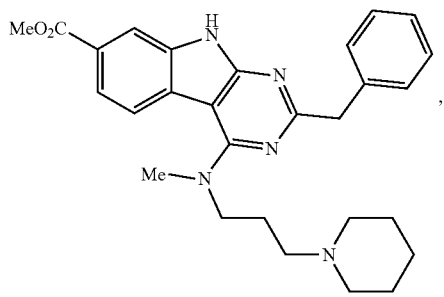,
(compound 5)
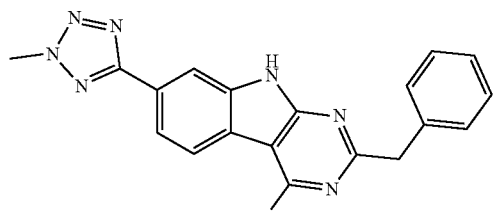
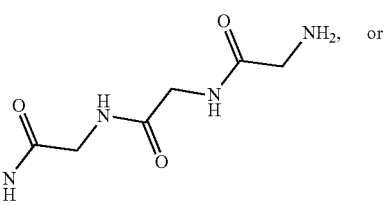 or -continued

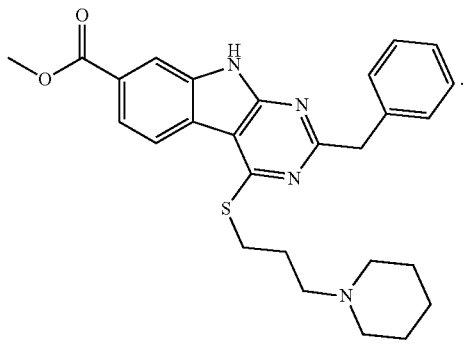

(compound 6)

In a further embodiment, the compound is

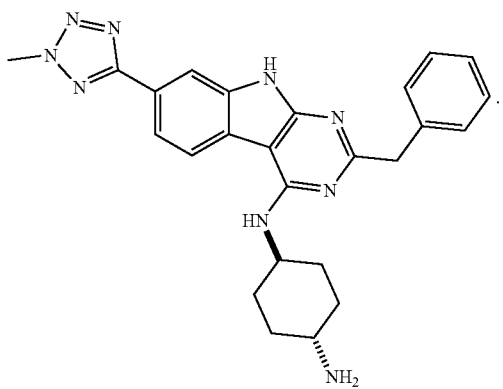

(compound 1)

In accordance with another embodiment, the compound is

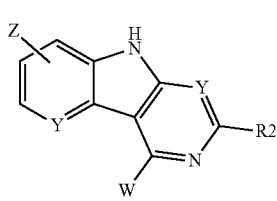

I or preferably

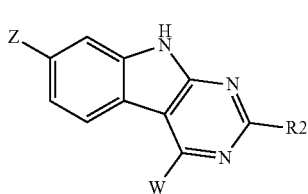

IIA or a salt thereof,
wherein
in formula I, each Y is the same or different and independently selected from N and CH Z is —C(O)O—$C_{1-4}$ alkyl, or -heteroaryl, preferably a 5-membered ring heteroaryl comprising 2-4 heteroatoms selected from N and O, optionally substituted with one or more RA or R4 substituents, W is —N(R1)R3, —NR1-$C_{1-6}$ alkylene-N(R1)R3, —O—$C_{1-6}$ alkylene-N(R1)R3, —S—$C_{1-6}$ alkylene-N(R1)R3, or —NR1-$C_{1-6}$ alkylene-(NR1-$C_{1-6}$ alkylene)$_n$-NR1R3 wherein n is an integer equal to either 0, 1, 2, or 3 and wherein, when R1 and R3 are attached to the same nitrogen atom, optionally they join together with the nitrogen atom to form a 5 to 6-membered ring which optionally includes one or more other heteroatom selected from N and O, optionally the ring is substituted with one or more RA or R4;

R1 is each independently —H, —$C_{1-6}$ alkyl, —$C_{3-7}$ cycloalkyl, or -heterocyclyl, wherein the alkyl, the cycloalkyl, the heterocyclyl are each independently optionally substituted with 1, 2 or 3 RA or Rd substituents;

R2 is —H, —$C_{1-6}$ alkyl, —$C_{1-6}$ alkylene-heteroaryl optionally substituted with one or more RA or R4 substituents either on the alkylene or the heteroaryl; or —$C_{1-6}$ alkylene-aryl optionally substituted with one or more RA or R4 substituents either on the alkylene or the aryl;

R3 is each independently —H, or —$C_{1-6}$ alkyl, wherein the alkyl group is optionally substituted with 1, 2 or 3 RA or Rd substituents;

R4 is each independently —H, or —$C_{1-6}$ alkyl, wherein the alkyl is optionally substituted with 1, 2 or 3 RA or Rd substituents;

RA is each independently -halogen, —$CF_3$, —OR1, —$OCF_3$, —SR1, —CN, —$NO_2$, —NR1R3, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, or —NR1C(O)N(R1)R3, and Rd is each independently —H, or —$C_{1-6}$ alkyl.

In accordance with another embodiment, the compound is

IIA

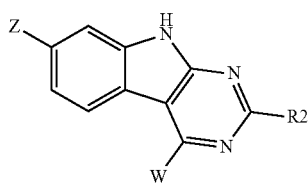

or a salt thereof, wherein

Z is —C(O)O—C$_{1-4}$ alkyl, or -heteroaryl, preferably a 5-membered ring heteroaryl comprising 2-4 heteroatoms selected from N and O, optionally substituted with one or more RA or R4 substituents, W is —N(R1)R3, —NR1-C$_{1-6}$ alkylene-N(R1)R3, —O—C$_{1-6}$ alkylene-N(R1)R3, —S—C$_{1-6}$ alkylene-N(R1)R3, or —NR1-C$_{1-6}$ alkylene-(NR1-C$_{1-6}$ alkylene)$_n$-NR1R3 wherein n is an integer equal to either 0, 1, 2, or 3 and wherein, when R1 and R3 are attached to the same nitrogen atom, optionally they join together with the nitrogen atom to form a 5 to 6-membered ring which optionally includes one or more other heteroatom selected from N and O, optionally the ring is substituted with one or more RA or R4;

R1 is each independently —H, —C$_{1-6}$ alkyl, —C$_{3-7}$ cycloalkyl, or -heterocyclyl, wherein the alkyl, the cycloalkyl, the heterocyclyl are each independently optionally substituted with 1, 2 or 3 RA or Rd substituents;

R2 is —H, —C$_{1-6}$ alkyl, —C$_{1-6}$ alkylene-heteroaryl optionally substituted with one or more RA or R4 substituents either on the alkylene or the heteroaryl; or —C$_{1-6}$ alkylene-aryl optionally substituted with one or more RA or R4 substituents either on the alkylene or the aryl;

R3 is each independently —H, or —C$_{1-6}$ alkyl, wherein the alkyl group is optionally substituted with 1, 2 or 3 RA or Rd substituents;

R4 is each independently —H, or —C$_{1-6}$ alkyl, wherein the alkyl is optionally substituted with 1, 2 or 3 RA or Rd substituents;

RA is each independently -halogen, —OR1, —NR1R3, —C(O)OR1, —C(O)N(R1)R3, —NR1C(O)R1, —NR1C(O)OR1, or —NR1C(O)N(R1)R3, and Rd is each independently —H, or —C$_{1-6}$ alkyl.

In accordance with another embodiment, the compound is of formula IIA

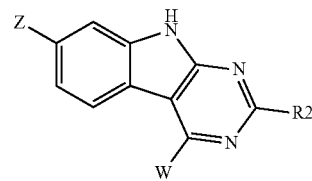

IIA or a salt thereof, wherein

Z is —C(O)O—C$_{1-4}$ alkyl or 5-membered ring heteroaryl, said heteroaryl comprising 2-4 heteroatoms selected from N and O;

R2 is H, —C$_{1-6}$ alkylene-heteroaryl or —C$_{1-6}$ alkylene-aryl, optionally substituted with one or more RA or R4 substituents;

W is —X-L-N(R1)R3 (wherein X is independently selected from O, S, and NR1) or preferably —NR1-L-N(R1)R3 wherein L is C2-4 alkylene or C3-7 cycloalkylene and R1 and R3 is C$_{1-4}$ alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

In accordance with another embodiment, the compound is of formula IIA

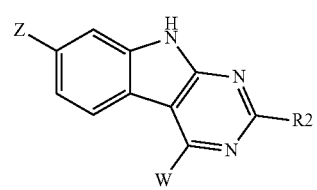

IIA or a salt thereof, wherein

Z is CO$_2$Me, COOEt, tetrazole or oxadiazole, preferably Z is CO$_2$Me or 2-methyl-2H-tetrazol-5-yl;

R2 is H, —C$_{1-6}$ alkylene-heteroaryl or —C$_{1-6}$ alkylene-aryl, optionally substituted with one or more RA or R4 substituents, preferably R2 is benzyl, or H;

W is —X-L-N(R1)R3 (wherein X is independently selected from O, S, and NR1) or preferably —NH-L-N(R1)R3 wherein L is C2-4 alkylene or C3-7 cycloalkylene and R1 and R3 is C$_{1-4}$ alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

In accordance with another embodiment, the compound is of formula IIA

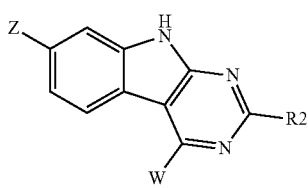

IIA or a salt thereof, wherein

Z is COOMe, COOEt, tetrazole or oxadiazole, preferably Z is CO$_2$Me or 2-methyl-2H-tetrazol-5-yl;

R2 is H, —C$_{1-6}$ alkylene-heteroaryl (wherein the heretoaryl is pyridinyl, pyrimidinyl or thienyl) or —C$_{1-6}$ alkylene-aryl, optionally substituted with one or more RA or R4 substituents, preferably R2 is optionally substituted benzyl, or H;

W is

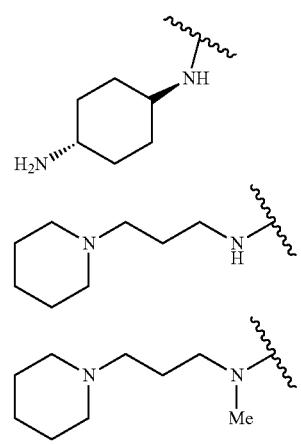

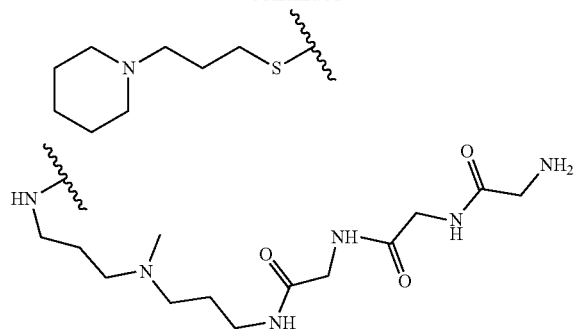

or preferably

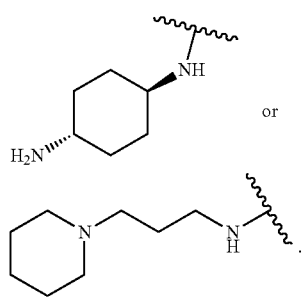

In accordance with another embodiment, the compound is of formula IIA

IIA

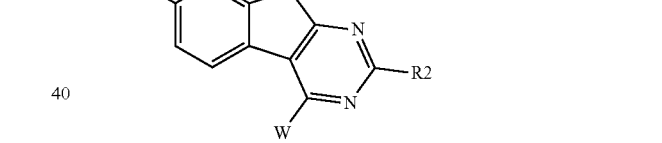

or a salt thereof,
wherein
Z is CO₂Me or 2-methyl-2H-tetrazol-5-yl;
R2 is H, —CH2-heteroaryl (wherein the heretoaryl is pyridinyl, pyrimidinyl or thienyl) or optionally substituted benzyl, or H;
W is

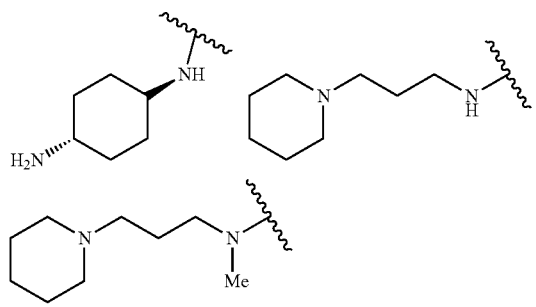

or preferably

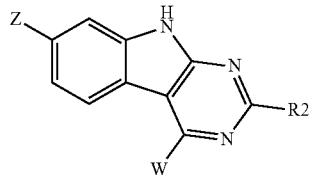

In accordance with another embodiment, the compound is of formula IIA

IIA

Z—[structure]—R2
W or a salt thereof,
wherein
Z is —C(O)OR1, or -heteroaryl optionally substituted with one or more RA or R1 substituents,
R2 is H, —C₁₋₆ alkyl optionally substituted with one or more RA substituents or -L-aryl optionally substituted with one or more RA or R4 substituents,
W is X-L-N(R1)R3 (wherein X is independently selected from O, S, and NR1) or preferably —N(R1)R3 wherein R1 is C3-7 cycloalkyl substituted by RA and R3 is H.

In accordance with another embodiment, the compound is of formula IIA

IIA

Z—[structure]—R2
W or a salt thereof, wherein Z is —C(O)O—C1-4 alkyl or 5-membered ring heteroaryl, said heteroaryl comprising 2-4 heteroatoms selected from N and O; R2 is H, or -L-aryl optionally substituted by halogen, OR1, $C_{1-6}$ alkyl optionally substituted by RA, C(O)R4, -heterocyclyl, C(O)OR4 or $C_{2-6}$ alkynyl; W is X-L-N(R1)R3 (wherein X is independently selected from O, S, and NR1) or preferably-N(R1)R3 wherein R1 is cyclohexyl substituted by RA, and R3 is H.

In accordance with another embodiment, the compound is of formula IIA

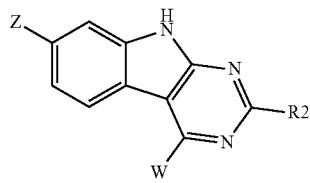

IIA or a salt thereof,
wherein Z is $CO_2Me$ or 2-methyl-2H-tetrazol-5-yl; R2 is benzyl, or H; and W is X-L-N(R1)R3 (wherein X is independently selected from O, S, and NR1) or preferably NH-L-N(R1)R3 wherein L is C2-4 alkylene or C3-7 cycloalkylene and R1 and R3 is C1-4 alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

In accordance with another embodiment, the compound is of formula IIA

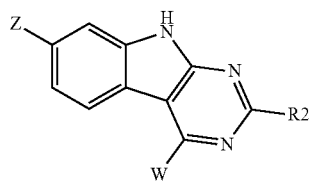

IIA or a salt thereof,
wherein Z is $CO_2Me$ or 2-methyl-2H-tetrazol-5-yl; R2 is benzyl, or H; and W is

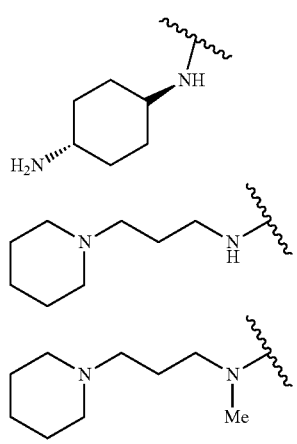

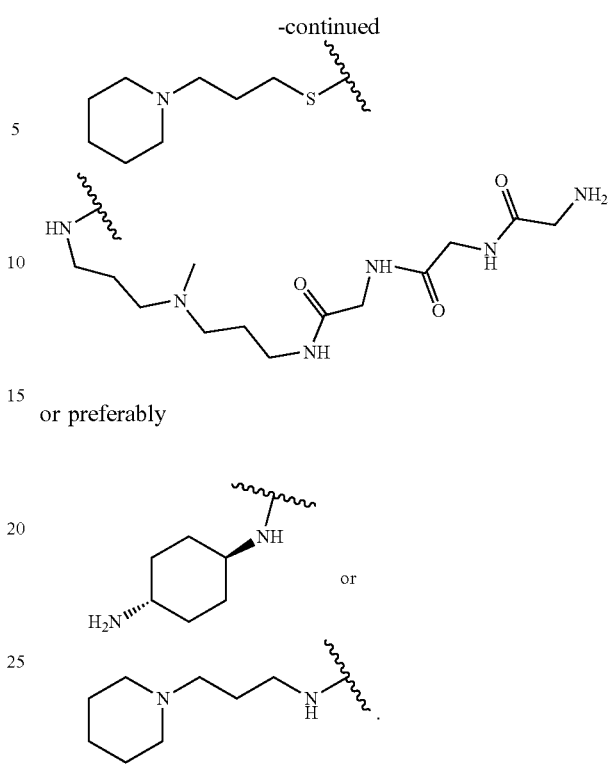

or preferably

In embodiments, the compound is one or more of compounds #1 to 90 set forth in Table 1 below.

The compounds of formulas I, II, and IIA, (including the representative compounds set forth above) disclosed herein, including the preparation and characterization thereof, are described in PCT publication No. WO 2013/110198, the content of which is incorporated by reference in its entirety as well as in the synthetic methodology section found below. These compounds are hereinafter referred to as "the compounds defined herein").

As used herein, the term "alkyl" is intended to include both branched and straight chain saturated aliphatic hydrocarbon groups having the specified number of carbon atoms, for example, $C_1$-$C_6$ in $C_1$-$C_6$ alkyl is defined as including groups having 1, 2, 3, 4, 5 or 6 carbons in a linear or branched saturated arrangement. Examples of $C_1$-$C_6$ alkyl as defined above include, but are not limited to, methyl, ethyl, n-propyl, i-propyl, n-butyl, t-butyl, i-butyl, pentyl, and hexyl. As used herein, the term "cycloalkyl" is intended to mean a monocyclic saturated aliphatic hydrocarbon group having the specified number of carbon atoms therein, for example, $C_3$-$C_7$ in $C_3$-$C_7$ cycloalkyl is defined as including groups having 3, 4, 5, 6 or 7 carbons in a monocyclic saturated arrangement. Examples of $C_3$-$C_7$ cycloalkyl as defined above include, but are not limited to, cyclopropyl, cyclobutyl, cyclopentyl, cyclohexyl and cycloheptyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ in $C_2$-$C_6$ alkenyl is defined as including groups having 2, 3, 4, 5 or 6 carbons in a linear or branched arrangement, at least two of the carbon atoms being bonded together by a double bond. Examples of $C_2$-$C_6$ alkenyl include, but are not limited to, ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ alkynyl is defined as including groups having 2, 3 or 4 carbon atoms in a chain, at least two of the carbon atoms being bonded together by a triple bond. Examples of such alkynyl include, but are not limited to, ethynyl, 1-propynyl, 2-propynyl and the like.

As used herein, the term "cycloalkenyl" is intended to mean a monocyclic saturated aliphatic hydrocarbon group having the specified number of carbon atoms therein, for example, $C_3$-$C_7$ in $C_3$-$C_7$ cycloalkenyl is defined as including groups having 3, 4, 5, 6 or 7 carbons in a monocyclic arrangement. Examples of $C_3$-$C_7$ cycloalkenyl as defined above include, but are not limited to, cyclopentenyl, cyclohexenyl and the like.

As used herein, the term "halo" or "halogen" is intended to mean fluorine, chlorine, bromine or iodine.

As used herein, the term "haloalkyl" is intended to mean an alkyl as defined above, in which each hydrogen atom may be successively replaced by a halogen atom. Examples of haloalkyl include, but are not limited to, $CH_2F$, $CHF_2$ and $CF_3$.

As used herein, the term "aryl," either alone or in combination with another radical, means a carbocyclic aromatic monocyclic group containing 6 carbon atoms which may be further fused to a second 5- or 6-membered carbocyclic group which may be aromatic, saturated or unsaturated. Examples of aryl include, but are not limited to, phenyl, indanyl, 1-naphthyl, 2-naphthyl, tetrahydronaphthyl and the like. The aryl may be connected to another group either at a suitable position on the cycloalkyl ring or the aromatic ring.

As used herein, the term "heteroaryl" is intended to mean a monocyclic or bicyclic ring system of up to 10 atoms, wherein at least one ring is aromatic, and contains from 1 to 4 hetero atoms selected from the group consisting of O, N, and S. The heteroaryl may be attached either via a ring carbon atom or one of the heteroatoms. Examples of heteroaryl include, but are not limited to, thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, tetrazolyl, oxadiazolyl, thiadiazolyl, thienyl, pyrimido-indolyl, pyrido-indolyl, pyrido-pyrrolo-pyrimidinyl, pyrrolo-dipyridinyl and fluoroscein derivatives.

As used herein, the term "heterocycle," "heterocyclic" or "heterocyclyl" is intended to mean a 3, 4, 5, 6, or 7 membered non-aromatic ring system containing from 1 to 4 heteroatoms selected from the group consisting of O, N and S. Examples of heterocycles include, but are not limited to, pyrrolidinyl, tetrahydrofuranyl, piperidyl, 3,5-dimethylpiperidyl, pyrrolinyl, piperazinyl, imidazolidinyl, morpholinyl, imidazolinyl, pyrazolidinyl, pyrazolinyl, tetrahydro-1H-thieno[3,4-d]imidazole-2(3H)-one, diazirinyl, and the like, where the attachment to the ring can be on either the nitrogen atom or a carbon atom of the ring such as described hereafter:

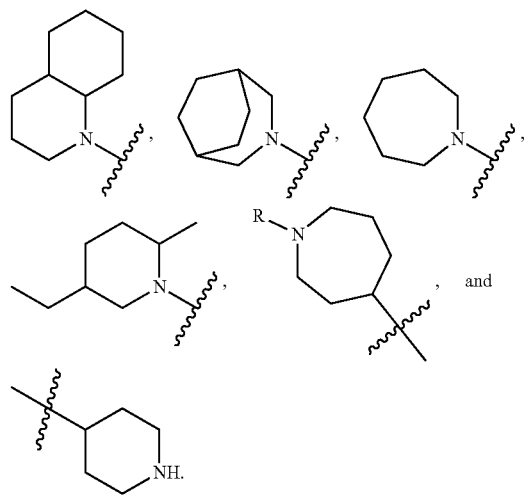

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

As used herein, the term "subject" or "patient" is intended to mean humans and non-human mammals such as primates, cats, dogs, swine, cattle, sheep, goats, horses, rabbits, rats, mice and the like.

If the substituents themselves are incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, "Protecting Groups in Chemical Synthesis" (4th ed.), John Wiley & Sons, NY (2007), which is incorporated herein by reference in its entirety. Examples of protecting groups used throughout include, but are not limited to, Fmoc, Bn, Boc, CBz and $COCF_3$. In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds according to the invention or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds according to the invention may exist as a mix of epimers. Epimers means diastereoisomers that have the opposite configuration at only one of two or more stereogenic centers present in the respective compound.

Compounds according to the invention may exist in Zwitterionic form and the present includes Zwitterionic forms of these compounds and mixtures thereof.

In addition, the compounds according to the invention also may exist in hydrated and anhydrous forms. Hydrates of the compound of any of the formulas described herein are included. In a further embodiment, the compound according to any of the formulas described herein is a monohydrate. In embodiments of the invention, the compounds described herein comprise about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In others embodiments, the compounds described herein comprise, about 0.1% or more, about 0.5% or more, about 1% or more, about 2% or more, about 3% or more, about 4% or more, about 5% or more, or about 6% or more by weight of water.

It may be convenient or desirable to prepare, purify, and/or handle the compound in the form of a prodrug. Thus, the term "prodrug", as used herein, pertains to a compound which, when metabolized (e.g., in vivo), yields the desired active compound. Typically, the prodrug is inactive, or less active than the desired active compound, but may provide advantageous handling, administration, or metabolic properties. Unless otherwise specified, a reference to a particular compound also includes prodrugs thereof.

As used herein, the term "$EC_{50}$" is intended to mean the concentration that results in a 50% increase in CD34+ CD45RA− cell count compared to vehicle cultures (DMSO).

In another aspect, the present invention provides a method for enhancing viral gene transfer efficacy to cells, said method comprising contacting a population of cells with a compound of general formulas I, IA or IIA as defined herein; and transducing said cells with a viral vector.

In another aspect, the present invention also provides a method for increasing the transduction efficiency of a population of cells cultured with a viral vector, said method comprising: culturing the population of cells and the viral vector in a culture medium that comprises at least one of the compounds defined herein, for a time sufficient to increase said transduction efficiency. In certain aspects, at least about 30%, 40%, 50%, 60%, 70%, 75%, 80%, 85%, 90% or 95% of the cell population is transduced using the method described herein.

In another aspect, the present invention provides a method for expressing a gene of interest (or a polypeptide of interest) into cells, said method comprising contacting said cells with at least one of the compounds defined herein; and transducing said cells with a viral vector comprising a nucleic acid encoding said gene of interest (or polypeptide of interest). The term "gene of interest" refers to any gene that encoded a protein (native or mutated) or an active fragment thereof, i.e. a polypeptide of interest. The gene of interest may be for example a gene that is absent or defective in a given disease.

In an embodiment, a combination of the compounds defined herein is used in the methods and compositions described herein. In another embodiment, the compounds defined herein may be used in combination with other agents or methods known to increase hematopoietic cell transduction efficiency, for example fibronectin or fibronectin fragment (CH-296), retronectin, HIV Tat, vectofusin-1, deoxynucleosides, cytokines (e.g., IL-6, SCF, FLT-3 ligand), compounds that modulate prostaglandin signaling such as $PGE_2$ (see WO 2014/026110) and/or mTOR inhibitors (e.g., rapamycin).

In an embodiment, the cells are primary cells, for example brain/neuronal cells, peripheral blood cells (e.g, lymphocytes, monocytes), cord blood cells, bone marrow cells, cardiac cells, endothelial cells, epidermal cells, epithelial cells, fibroblasts, hepatic cells or lung/pulmonary cells. In an embodiment, the cells are bone marrow cells, peripheral blood cells or cord blood cells.

In an embodiment, the cells are stem cells. The term "stem cells" as used herein refers to cells that have pluripotency which allows them to differentiate into functional mature cells. It includes primitive hematopoietic cells, progenitor cells, as well as adult stem cells that are undifferentiated cells found in various tissue within the human body, which can renew themselves and give rise to specialized cell types and tissue from which the cells came (e.g., muscle stem cells, skin stem cells, brain or neural stem cells, mesenchymal stem cell, lung stem cells, liver stem cells).

In an embodiment, the cells are primitive hematopoietic cells. As used herein, the term "primitive hematopoietic cells is used to refers to cells having pluripotency which allows them to differentiate into functional mature blood cells such as granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages), and that may or may not the ability to regenerate while maintaining their pluripotency (self-renewal). It encompasses "hematopoietic stem cells" or "HSCs", which are cells having both pluripotency which allows them to differentiate into functional mature cells such as granulocytes, erythrocytes, thrombocytes, and monocytes, and the ability to regenerate while maintaining their pluripotency (self-renewal), as well as pluripotent hematopoietic cells that do not have self-renewal capacity. In an embodiment, the population of cells comprises HSCs. HSCs may obtained from the body or an organ of the body containing cells of hematopoietic origin. Such sources include un-fractionated bone marrow (from femurs, hip, ribs, sternum, and other bones), umbilical cord blood, peripheral blood, liver, thymus, lymph and spleen. All of the aforementioned crude or un-fractionated blood products can be enriched for cells having HSC characteristics in ways known to those of skill in the art. HSCs are phenotypically identified by their small size, lack of lineage (lin) markers, low staining (side population) with vital dyes such as rhodamine 123 (rhodamine$^{DULL}$, also called rho$^{10}$) or Hoechst 33342, and presence/absence of various antigenic markers on their surface many of which belongs to the cluster of differentiation series, such as: CD34, CD38, CD90, CD133, CD105, CD45 and c-kit.

In an embodiment, the population of cells comprises hematopoietic stem cells (HSCs).

In an embodiment, the cells are mammalian cells, for example human cells.

The term "viral vector" as used herein refers to a recombinant virus capable of transducing cells and introducing their genetic material into the cells. Examples of viral vectors that may be used in gene therapy include retroviruses (lentiviruses), adenoviruses, adeno-associated viruses, herpesviruses (herpes simplex viruses), alphaviruses, and vaccinia viruses (Poxviruses). In an embodiment, the viral vector is a lentiviral vector.

The term "lentiviral vector" refers to a vector containing structural and functional genetic elements outside the LTRs that are primarily derived from a lentivirus. Lentiviral vectors are capable of providing efficient delivery, integration and long term expression of transgenes into non-dividing cells both in vitro and in vivo. A variety of lentiviral vectors are known in the art, see Naldini et al, (1996a, 1996b, and 1998); Zufferey et al, (1997); Dull et al, 1998, U.S. Pat. Nos. 6,013,516; and 5,994,136, any of which may be adapted to produce a suitable transfer vector to be used in the method and composition of the present invention. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one aspect, HIV-based vector backbones are preferred. In an embodiment, the lentiviral vector is a replication-defective lentivirus.

As will be evident to one of skill in the art, the term "lentiviral vector" is used to refer to a lentiviral particle that mediates nucleic acid transfer. Lentiviral particles will typically include various viral components and sometimes also host cell components in addition to nucleic acid(s). In particular aspects, the terms "lentiviral vector," "lentiviral expression vector" are used to refer to lentiviral transfer plasmids and/or infectious lentiviral particles.

In an embodiment, the lentiviral vector is a pseudotyped lentiviral vector. Pseudotyped lentiviral vectors consist of vector particles bearing enveloped proteins (glycoproteins, GP) derived from other enveloped viruses. Such particles possess the tropism of the virus from which the enveloped proteins is derived. One of the widely used glycoproteins for pseudotyping lentiviral vectors is the vesicular stomatitis virus GP (VSV-G), due to the very broad tropism and stability of the resulting pseudotypes. Pseudotyped lentiviral vectors are well known in the art, and several examples are described, for example, in Cronin et al., *Curr. Gene Ther.* 5(4):387-398. It includes lentiviral vectors pseudotyped with lyssavirus GPs, lymphocytic choriomeningitis virus (LCMV) GPs, alphavirus GPs (e.g., Ross River virus (RRV), Semliki Forest virus (SFV) and Sindbis virus GPs), Filovirus GPs (e.g., Marburg virus and Ebola Zaire virus GPs), gammaretrovirus GPs (e.g., ecotropic MLV, amphotropic 4070A MLV, 10A1 MLV, xenotropic NZB MLV, mink cell focus-forming virus, gibbon ape leukemia (GALV) virus, RD114 GPs) and baculovirus GPs (GP64).

In an embodiment, the viral vector is an integration-defective viral vector, such as a non-integrating adenoviral vector or an integrase-deficient lentivirus (IDLV). IDLVs can be produced through the use of mutations in the integrase protein that minimize proviral integration. The resulting IDLV generates circular vector episomes in transduced target cells that are gradually lost by dilution in dividing cells (transient expression), but are stable in quiescent cells. Inherently, IDLVs have a greatly reduced risk of causing insertional mutagenesis compared to integrating lentiviruses. Therefore, IDLVs may be particularly useful for applications where transient expression is required or for sustained episomal expression such as in quiescent cells, for example for vaccinations, cancer therapy, site-directed gene insertions, gene disruption strategies, and cell reprogramming. The design and applications of IDLVs are described for example, in Shaw and Cornetta, *Biomedicines* 2014, 2, 14-35.

In another aspect, the present invention provides a method for transiently expressing a gene of interest into cells, said method comprising contacting said cells with at least one of the compounds defined herein; and transducing said cells with a non-integrating viral vector comprising a nucleic acid encoding said gene of interest.

In another aspect, the present invention provides lentiviral vectors that comprise an expression control sequence that directs expression of polynucleotide-of-interest in a particular cell type or cell lineage. The use of a cell type or cell lineage expression control sequence offers safety advantages in restricting polynucleotide expression to a desired stage of cell differentiation in a single lineage; and thus, vectors of the invention alleviate concerns dealing with ectopic expression of polypeptides in undesired cells types.

In an embodiment, the expression control sequence may a cell type or cell lineage specific expression control sequence that directs expression of the polynucleotide-of-interest in a hematopoietic stem cell, a hematopoietic progenitor cell, a myeloid cell, a lymphoid cell, a thrombopoietic lineage, a mast cell, an erythropoietic lineage cell, a granulopoietic lineage cell, and a monocytopoietic lineage cell. In one aspect, the vector comprises a hematopoietic cell promoter, enhancer, or promoter/enhancer operably linked to a gene of interest.

The production of infectious viral particles and viral stock solutions may be carried out using conventional techniques. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113.

In particular aspects, HIV-1-based viral particles may be generated by co-expressing the virion packaging elements and the transfer vector in a producer cell. These cells may be transiently transfected with a number of plasmids. Typically from three to four plasmids are employed, but the number may be greater depending upon the degree to which the lentiviral components are broken up into separate units. For example, one plasmid may encode the core and enzymatic components of the virion, derived from HIV-1. This plasmid is termed the packaging plasmid. Another plasmid typically encodes the envelope protein(s), most commonly the G protein of vesicular stomatitis virus (VSV-G) because of its high stability and broad tropism. This plasmid may be termed the envelope expression plasmid. Yet another plasmid encodes the genome to be transferred to the target cell, that is, the vector itself, and is called the transfer vector. The packaging plasmids can be introduced into human cell lines by known techniques, including calcium phosphate transfection, lipofection or electroporation. Recombinant viruses with titers of several millions of transducing units (or infectious units, IU) per milliliter (TU/ml) can be generated by this technique and variants thereof. After ultracentrifugation concentrated stocks of about $10^8$ TU/ml, $10^9$ TU/ml, $10^{10}$ TU/ml, $10^{11}$ TU/ml, $10^{12}$ TU/ml, or about $10^{13}$ TU/ml can be obtained.

Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

As used herein, the term "transduction" refers to the stable transfer of genetic material from a viral particle (e.g., lentiviral) to a cell genome (e.g., primitive hematopoietic cell genome). It also encompasses the introduction of non-integrating viral vectors into cells, which leads to the transient or episomal expression of a gene of interest present in the viral vector. As used herein, the term "time sufficient to increase transduction efficiency" refers to a time period in which a population of cells may be cultured together with the compounds defined herein such that, when the population of cells is brought into contact with a viral vector, the cells are transduced with the viral vector at a higher transduction efficiency, defined as the percentage of cells which are transduced with the viral vector, compared to a similar population of cells that is brought into contact with a similar viral vector, in the absence of the compounds defined herein. In particular embodiments, increase in transduction efficiency represents at least 2-fold, at least 3-fold, at least 5-fold, at least 10-fold, at least 25-fold, at least 50-fold, or at least 100-fold enrichment of transduced cells treated with the compounds defined herein compared to untreated cells treated with the viral vector alone.

Viruses may be used to infect cells in vivo, ex vivo, or in vitro using techniques well known in the art. For example, when cells, for instance $CD34^+$ cells or stem cells are transduced ex vivo, the vector particles may be incubated with the cells using a dose generally in the order of between 1 to 100 or 1 to 50 multiplicities of infection (MOI) which also corresponds to $1 \times 10^5$ to 100 or $50 \times 10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI.

In an embodiment, the cells, for example primitive hematopoietic cells, may be contacted with the compounds defined herein prior to and/or during the transduction with the viral vector. In an embodiment, the cells, for example primitive hematopoietic cells, are contacted with the compounds defined herein prior to the transduction with the viral vector (prestimulation). In a particular aspect, the cells are cultured with the compounds defined herein prior to transduction for at least about 1 hours or 2 hours. In other aspects, the cells are cultured with the compounds defined herein prior to transduction for at least about 2, 3 or 4 hours. In embodiment, the cells are cultured with the compounds defined herein prior to transduction for a period of about 1 to about 24 hours, about 2 to about 24 hours, or about 2 to about 22 hours. In further embodiments, the cells are cultured with the compounds defined herein prior to transduction for a period of about 2, 3, 4, 5, 6, 7, 8, 9, 10, 11, 12, 13, 14, 15, 16, 17, 18, 19, 20, 21 or 22 hours.

In other aspects, the cells are cultured in the presence of the compounds defined herein during transduction (costimulation). In one aspect, the cells are cultured in the presence of the compounds defined herein during transduction (costimulated) for at least 1, 2, 3, 4, 6, 8, 10, 12, 14, 16, 18, 20 or 24 hours. In certain other aspects, the cells are cultured in the presence of the compounds defined herein during the first 24 hours of transduction, or during the first 36 or 48 hours of transduction. The cells may be cultured in the presence of the compounds defined herein at any time during the transduction period, for example during the first hours (i.e. the first 2, 3 or 4 hours), at the end of the transduction (during the last 2, 3 or 4 hours), and/or in the middle of the transduction period.

In another aspect, the cells may be cultured in the presence of the compounds defined herein both prior to transduction (prestimulated) and during transduction (costimulated). In a particular aspect, following transduction, the cell population may be washed or otherwise treated to remove some or all of the compounds defined herein.

The starting cell population (i.e. the cell population contacted with the compounds defined herein and transduced) can be enriched based on the expression of certain cell surface markers, such as CD34, CD38 and/or CD45RA using methods well known in the art. Thus, the starting cell population may be enriched, for example, in $CD34^+$ cells, $CD34^+CD45RA^-$ cells or $CD34^+CD38^-$ cells. Moreover, the starting cell population may be used directly or frozen and stored for use at a later point in time.

Thus, the cell population may first be subjected to enrichment or purification steps, including negative and/or positive selection of cells based on specific cellular markers (CD34, CD38 and/or CD45RA) in order to provide the starting cell population, for example to provide a starting cell population enriched in HSCs. Methods for isolating said starting cell population based on specific cellular markers may use fluorescent-activated cell sorting (FACS) technology or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator (magnetic cell sorting, MACS®). In one embodiment, the starting cell population is enriched in $CD34^+$ cells. Methods for enriching blood cell population in $CD34^+$ cells include kits commercialized by Miltenyi Biotec® ($CD34^+$ direct Isolation® kit, Miltenyi Biotec®, Bergisch, Gladbach, Germany) or by Baxter® (Isolex® 3000). Kits for enrichment of human hematopoietic progenitor cell from bone marrow or blood are also commercially available (e.g., StemSep™ Human Hematopoietic Progenitor Cell Enrichment Kit).

In an embodiment, the starting cell population is derived from neonatal umbilical cord blood cells which have been enriched in $CD34^+$ cells. In one related embodiment, said starting cell population is derived from one or two umbilical cord blood units.

In another embodiment, the starting cell population is derived from human mobilized peripheral blood cells which have been enriched in $CD34^+$ cells. In an embodiment, the starting cell population may preferably contain at least 50% $CD34^+$ cells, in some embodiments, more than 60, 70, 80, 90 or 95% of $CD34^+$ cells.

Prior to, during, and/or following transduction, the cells may be cultured in media suitable for the maintenance, growth, or proliferation of the cells. The culture conditions of the population of cells will vary depending on different factors, notably, the starting cell population. Suitable culture media and conditions are well known in the art. The method of the present invention may be carried out in natural medium, a semi-synthetic medium or a synthetic medium in terms of composition, and may be a solid medium, a semisolid medium or a liquid medium in terms of shape, and any nutrient medium used for HSC and/or hematopoietic progenitor cell culture, which may be supplemented with one or more of the factors described above. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. Examples of such basal medium appropriate for a method of expanding HSCs include, without limitation, StemSpan™ Serum-Free Expansion Medium (SFEM) (StemCell Technologies®, Vancouver, Canada), StemSpan™ H3000-Defined Medium (StemCell Technologies®, Vancouver, Canada), CellGro™, SCGM (CellGenix™, Freiburg Germany), StemPro™-34 SFM (Invitrogen®), Dulbecco's Modified Eagles's Medium (DMEM), Ham's Nutrient Mixture H12 Mixture F12, McCoy's 5A medium, Eagles's Minimum Essential Medium (EMEM), αMEM medium (alpha Modified Eagles's Minimum Essential Medium), RPMI1640 medium, Isocove's Modified Dulbecco's Medium (IMDM), StemPro34™ (Invitrogen®), X-VIVO™ 10 (Cambrex®), X-VIVO™ 15 (Cambrex®) and Stemline™ II (Sigma-Aldrich®).

Following transduction, the transduced cells may be cultured under conditions suitable for their maintenance, growth and/or proliferation. In particular aspects, the transduced cells are cultured for about 1, 2, 3, 4, 5, 6, 7, 8, 9, 10, 11, 12, 13 or 14 days before transplantation.

Culture conditions for maintaining and/or expanding primitive hematopoietic cells such as HSCs are well known in the art. Typically, the culturing conditions comprise the use of factors like cytokines and growth factors, generally known in the art for HSC expansion. Such cytokines and growth factors can be biologics or small molecules and they include without limitation IL-1, IL-3, IL-6, IL-11, G-CSF, GM-CSF, SCF, FIT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to maintain/expand HSC and progenitor cells while limiting the production of terminally differentiated cells. In one specific embodiment, one or more cytokines and growth factors are selected from the group consisting of SCF, Flt3-L and TPO. The medium may be supplemented with factors that promote HSC expansion, including SR1. Furthermore, in view of the fact that the compounds defined herein have been shown to promote HSC expansion (see WO 2013/110198), such compound may further be added to the culture medium during the expansion period.

Human IL-6 or interleukin-6, also known as B-cell stimulatory factor 2 has been described by (Kishimoto, Ann. review of 1 mm. 23:1 2005) and is commercially available. Human SCF or stem cell factor, also known as c-kit ligand, mast cell growth factor or Steel factor has been described (Smith, M A et al., ACTA Haematologica, 105, 3:143, 2001) and is commercially available. Flt3-L or FLT-3 Ligand, also referred as FL is a factor that binds to flt3-receptor. It has been described (Hannum C, Nature 368 (6472): 643-8) and is commercially available. TPO or thrombopoietin, also known as megakarayocyte growth factor (MGDF) or c-Mpl ligand has been described (Kaushansky K (2006). N. Engl. J. Med. 354 (19): 2034-45) and is commercially available.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

Primitive hematopoietic cells such as HSCs can be cultured in a culture vessel generally used for animal cell culture such as a Petri dish, a flask, a plastic bag, a Teflon™ bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel®, poly-D-lysine, poly-L-lysine, chitin, chitosan, Sepharose®, alginic acid gel, hydrogel or a fragment thereof. Such a coating material may be a recombinant material having an artificially modified amino acid sequence. The primitive hematopoietic cells such as HSCs may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The cell population may then be washed to remove the compound or composition of invention and/or any other component of the cell culture and resuspended in an appropriate cell suspension medium for short term use or in a long-term storage medium, for example a medium suitable for cryopreservation, for example DMEM with 40% FCS and 10% DMSO. Other methods for preparing frozen stocks for cultured cells also are available to those skilled in the art.

The present invention also provides a population of transduced cells obtained by the method described herein. The present invention also provides a population of cells comprises transduced cells obtained by the method described herein. In an embodiment, the cell population comprises at least about 20, 25, 30, 35, 40, 45, 50, 55, 60, 65, 70, or 75% of transduced cells, i.e. comprising the viral vector and/or expressing a gene of interest present in the viral vector.

The present invention further contemplates cell-based compositions comprising a culture of cells in culture medium comprising a viral vector and at least one of the compounds as defined herein. As discussed herein throughout, in particular aspects, the present compositions and methods are useful for ex vivo and in vivo cell-based gene therapies. In some aspects, the cell culture medium is a pharmaceutically acceptable cell culture medium.

The formulations and compositions of the invention may comprise a combination of any number of transduced or non-transduced cells or a combination thereof, viral vectors, polypeptides, polynucleotides, and one or more compounds, e.g., the compounds as defined herein, formulated in pharmaceutically-acceptable or physiologically-acceptable solutions (e.g., culture medium) for administration to a cell, tissue, organ, or an animal, either alone, or in combination with one or more other modalities of therapy.

The present invention further includes pharmaceutical compositions comprising transduced cells produced according to methods described herein and a pharmaceutically acceptable carrier. In other aspects, the present invention provides pharmaceutical compositions comprising a viral vector and one or more compounds as defined herein.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. In one aspect, a composition comprising a carrier is suitable for parenteral administration, e.g., intravascular (intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The compositions of the invention may comprise one or more polypeptides, polynucleotides, vectors comprising same, compounds, and transduced cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules or various pharmaceutically-active agents.

In particular aspects, host cells or target cells transduced with a viral vector of the invention express a therapeutic polypeptide and are administered to a subject to treat and/or prevent a disease, disorder, or condition.

The transduced cells and corresponding viral vectors provide improved methods of gene therapy. As used herein, the term "gene therapy" refers to the introduction of a gene into a cell's genome. In various aspects, a viral vector of the invention comprises a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition that is amenable to hematopoietic stem cell therapy.

The present invention contemplates that the vector, viral particles, and transduced cells of the invention are be used to treat, prevent, and/or ameliorate a monogenic disease, disorder, or condition or a disease, disorder, or condition of the hematopoietic system in a subject, e.g., a hemoglobinopathy. Hemoglobinopathy refers to a disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. The treatment, prevention and/or amelioration of other diseases amenable to HSC-based gene therapy is also contemplated, including certain hematologic and lysosomal storage diseases such as Wiskott-Aldrich syndrome (WAS) (Aiuti et al., Science 341(6148)), metachromatic leukodystrophy (MLD) (Biffi et al., Science 341(6148)), Leukocyte adherence deficiency, X-linked CGD, Fanconi anemia, adrenoleukodystrophy, Mucopolysaccharidosis IIIA, immunodeficiencies such as severe combined immunodeficiency (SCID) and adenosine deaminase (ADA) deficiency, and infectious diseases such as HIV (Watts et al., Cytotherapy 13(10): 1164-71). For such treatments, the viral vector comprises a nucleic acid that encodes one or more proteins that is/are defective in the disease. The viral vector (e.g., integration-defective viral vector) may also comprise a nucleic acid encoding an antigen or immunogen (for vaccination) or one or more differentiation factor(s) (for cell reprogramming), for example.

The present invention also provides a method of treating a subject in need of a treatment with cell gene therapy, said method comprising administering to said subject an effective amount of the population of transduced cells or a pharmaceutical composition comprising the population of transduced cells as defined herein. In an embodiment, the method comprises: (i) transducing a viral vector into cells from said subject in the presence of a compound of general formula I defined herein, thereby obtaining a population comprising transduced cells; and (ii) administering to said subject an effective amount of the population comprising transduced cells obtained in (i), or a pharmaceutical composition comprising said population comprising transduced cells.

The present invention also provides the use of a population comprising transduced cells obtained by the methods defined herein (or a pharmaceutical composition comprising same) for treating a subject in need of a treatment with cell gene therapy. The present invention also provides the use of a population comprising transduced cells obtained by the method defined herein (or a pharmaceutical composition comprising same) for the preparation of a medicament for treating a subject in need of a treatment with cell gene therapy. In an embodiment, the use comprises: (i) performing the method for transducing a viral vector into cells defined herein to obtain a population comprising transduced cells, and (ii) use of the population comprising transduced cells obtained in (i) (or a pharmaceutical composition comprising same) for treating a subject in need of a treatment with cell gene therapy.

The pharmaceutical compositions comprising transduced cells are formulated in any conventional manner for use in the methods described herein. Administration is via any route known to be effective by one of ordinary skill. For example, the composition is administered orally, parenterally (e.g., intravenously), by intramuscular injection, by intraperitoneal injection, transdermally, extracorporeally, intranasally or topically.

The preferred method of administration is intravenous infusion. The number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least >0.3×10$^5$ CD34$^+$ cells/kg or >2×10$^6$ CD34$^+$ cells for cord blood and 2.5×10$^5$ CD34$^+$ cells/kg or more for bone marrow or mobilized peripheral blood cells.

Also provided herein is a kit comprising one or more containers filled with one or more of the ingredients described herein. Such kits optionally comprise solutions and buffers as needed or desired. The kit optionally includes a population of cells, e.g., stem cells, made by the methods described above or can contain containers or compositions for making a population of HSCs. In particular, the invention provides a kit for transducing cells, such as primitive hematopoietic cells (e.g., hematopoietic stem cells) ex vivo, comprising a compound as defined herein and instructions for using such compound in a method for cell transduction and, optionally, one or more cell factors, or media for cell growth, in particular media for HSC growth as described above. The kit may further comprise a viral vector, e.g., comprising a gene of interest, for transducing the cells. The kit may further comprise antibodies for monitoring production of the cells, such as anti-CD34, anti-CD38 and/or anti-CD45RA antibodies. In one specific embodiment, such kit further includes one or more cell expanding factor selected from the group consisting of IL6, FLT3-L, SCF and TPO.

The methods and compositions of the present invention may be useful for various applications where high gene transfer is an asset, including in vitro studies (e.g., functional studies of genes, screens for genes with specific function, gene expression analysis, gene editing), in vivo studies (e.g., functional studies, assessment of gene therapy approaches).

Without wishing to be bound to any particular theory, it is contemplated that the compositions and methods of the present invention may be used to transduce significantly more cells with significantly less virus, thereby minimizing the risk of genomic alteration and/or insertional activation of proto-oncogenes in the genome of the therapeutic cell. Minimizing the risk of insertional activation of proto-oncogenes and other genomic alterations in the therapeutic cell is an important consideration in devising a suitable gene therapy protocol because it minimizes the chance that transduced cells comprising cancer like characteristics will be clonally expanded in vivo and give rise to cancers, tumors or other diseases involving abnormal cell proliferation. Moreover, the art has noted that transduction with large amounts of virus may be generally cytotoxic to the transduced cell. Thus, the compositions and methods of the present invention further enhance the survivability of transduced cells. Accordingly, the present invention provides a safer and more efficient gene therapy.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

MODE(S) FOR CARRYING OUT THE INVENTION

The present invention is illustrated in further details by the following non-limiting examples.

Materials and Methods Related to Example 1
(FIGS. 1 to 4)

Human CD34$^+$ Cord Blood Cell Collection

Human CD34$^+$ cord blood (CB) cells were isolated using RosetteSep™ CD34 preenrichment cocktail followed by CD34 positive selection using EasySep™ (StemCell Technologies).

CD34+ Cell Culture

Human CD34+ cells were cultured in HSC expansion media consisting of StemSpan SFEM (StemCell Technologies) supplemented with human 100 ng/ml stem cell factor (SCF, R&D Systems), 100 ng/ml FMS-like trysine kinase 3 ligand (FLT3, R&D Systems), 50 ng/ml thrombopoietin (TPO, R&D Systems), and 10 µg/ml low-density lipoproteins (StemCell Technologies).

Compound

Cmpd1 [35 nM], SR1 (Alichem, 41864) [750 nM] or combination of Cmpd1 [35 nM]+SR1 [500 nM].

Lentiviral Vector Preparation

Co-transfection of HEK293 cells was performed with plasmids: pCCL-c-MNDU-eGFP, pCMV-Gag/Pol (PLP1; sigma), pRSV-Rev (PLP2; sigma) and pCMV-VSV/G (PLP; sigma) or pCMV-RDT. Lentiviral soup was collected after 48 hours post-transfection. Lentiviral particles were concentrated by PEG-It™ (System Biosciences) precipitation. Virus titer measurement was done onHEK293 cells. To enhance lentiviral-mediated gene transfer, lentivirus was preloaded into a RetroNectin (Takara) coated plate according to the manufacturer's guidelines.

Human CD34+ CB Cell Transduction

Fresh (24 or 48 hr-prestimulated) or cultured CD34+CB cells were transduced by GFP virus of VSV or RDT envelope with MOI 10, 50 or 100 for 12 or 16 hours. Cells then were washed and kept in culture for 3 or 10 days post-infection. FACS analysis was performed to monitor the percentage of GFP transduced cells in total, CD34+ or CD34+CD45RA− population.

Flow Cytometry

Flow cytometry analysis was performed on BD LSR II cytometer. Fresh or cultured GFP-transduced CD34+CB cells were stained in PBS supplemented with 2% fetal bovine serum (FBS) at 4° C. for 15 minutes with APC-labelled anti-human CD34 (BD Biosciences) and PE-labelled anti-human CD45RA (BD Biosciences). Data analysis was done using BD FACSDiva™ software.

Xenotransplantation

All experiments with animals were conducted under protocols approved by the Animal Care Committee of University of Montreal. The progeny of 1000 CD34+ CB cells GFP-transduced or not expanded for 10 days vehicle (DMSO) or Cmpd1 [35 nM] were transplanted by tail vein injection into sub-lethally irradiated (250 cGy, <24 hr before transplantation) 8 to 12 week-old female NSG (NODScidIL2Rγnull, Jackson Laboratory). Human cells in NSG bone marrow (BM) was monitored by flow cytometry 30 weeks post-transplantation. NSG BM cells were collected by flushing the two femurs, tibias and hips. Cells were then treated with 1× red blood cell lysis buffer (StemCell Technologies) and stained with pacific blue-labelled anti-human CD45 (BioLegend), APC-eFluo-labelled 780 anti-mouse CD45 (eBioscience) to monitor the human blood reconstitution in NSG BM cells.

Materials and Methods Related to Examples 1 to 9 (FIGS. 5 to 20)

Viral Vectors and Virus Production

Unless otherwise specific, the pCCI-c-MNDUSpgkGFP or pCCI-c-MNDUSpgkYFP lenti-viral vector backbone was used in these studies (Logan A C et al, Human Gene Therapy 2004). The vector constructs were sequence-verified. High-titer recombinant virus pseudotyped with vesicular stomatitis virus glycoprotein-G was produced by transient transfection of 293T cells using a standard 4-plasmid packaging system. Virus-containing supernatants were concentrated by ultracentrifugation to achieve titers of $0.5 \times 10^9$ to $5 \times 10^9$ infectious units/ml. Viral titers were determined by transducing HeLa cells with three dilutions of the lentiviral vector. For tests of a non-integrating formulation of lentivirus, viral supernatant (a gift of Dr. Donald Kohn, Department of Microbiology, Immunology and Molecular Genetics and Department of Pediatrics, University of California, Los Angeles) for lentiviral vector expressing GFP under the control of a modified myeloproliferative sarcoma virus LTR (MND-GFP-IDLV) was generated using a catalytically inactive integrase (Joglekar A V et al., Mol Ther. 2013 September; 21(9):1705-17, PMID 23857176).

Isolation and Culture of Human Umbilical Cord Blood, Mobilized Peripheral Blood and Adult Bone Marrow Cells Umbilical cord blood (CB) and mobilized peripheral blood (mPB) cells were collected with consent according to procedures approved by the Research Ethics Board of the University of British Columbia. CD34+ enriched adult bone marrow cells were purchased from STEMCELL Technologies. CD34+ CB and mPB cells were enriched to >90% purity using first RosetteSep™ CD34 preenrichment cocktail (STEMCELL Technologies) followed by positive selection using magnetic beads (EasySep kit, STEMCELL Technologies). In some cases additional enrichment was done by sorting CD34+ cells using an Influx II sorter (BD Bioscience). CD34+ CB cells were pre-stimulated for 16 hours in serum free medium (SFM; Iscove's medium supplemented with bovine serum albumin, insulin and transferrin (BIT, STEMCELL Technologies), 10 µg/ml of low density lipoprotein (LDL, STEMCELL Technologies), $10^{-4}$ M 2-mercaptoethanol (Sigma-Aldrich), $10^{-4}$ M glutamax 500 (STEMCELL Technologies), penicillin and streptomycin) supplemented with 100 ng/mL FLT3-ligand (FL), 100 ng/mL Steel Factor (SF), 20 ng/mL IL-3, IL-6 and granulocyte colony-stimulating factor (G-CSF) (all from STEMCELL Technologies). In one experiment CB cells were prestimulated in the presence of only 3 growth factors, 100 ng/mL FL, 100 ng/mL SF and 50 ng/mL TPO (STEMCELL Technologies). Adult BM and mPB CD34+ cells were prestimulated for 24 hours in SFM supplemented with 100 ng/mL FL, 100 ng/mL Steel Factor SF, 100 ng/mL TPO and 20 ng/mL IL-3. The cells were prestimulated in the presence or absence of Cmpd1 (35 nM), SR1 (0.75 µM) or DMSO (not exceeding 0.01%). In one experiment, rapamycin was also added during the prestimulation phase (10 µg/mL) with or without Cmpd1 (35 nM).

Transduction of Human CD34+ Cells

At the end of prestimulation the cells were resuspended in fresh growth factor-supplemented SFM with concentrated lentivirus (GFP or YFP and in one experiment globin, NA10HD, MN1, and ND13 virus were also used) and 5 µg/mL protamine sulfate and incubated at 37° C. for 6 hours for CB and 24 hours for BM and mPB cells at a virus concentration of $1 \times 10^6$ or $1 \times 10^7$ IU/mL, and placed in a 96-well plate coated with 5 µg/cm² fibronectin (Sigma-Aldrich). The cells were transduced in the presence or absence of Cmpd1 (35 nM), SR1 (0.75 µM) or DMSO (not exceeding 0.01%). In one experiment, cells were also transduced in the presence of Rapamycin (10 µg/mL) with or without Cmpd1 (35 nM). At the end of infection, cells were washed several times with PBS and used for in vivo experiments and cultured for an additional 72 hours in fresh growth factor-supplemented SFM. Gene transfer efficiency to various CD34+ cell subsets was determined after staining the cells with the following anti-human-specific antibodies (all from eBioscience unless noted): CD34-APC (clone 8G12, STEMCELL Technologies), CD38-PECy7 (clone HIT2), Thy1-PE (clone eBio5E10), CD45RA-APC780 (clone HI100) and CD49f-EF450 (clone eBioGoH3). All flow cytometric analysis was performed using a LSRII Fortessa® (BD Biosciences).

Mice

NOD.Cg-Prkdc$^{scid}$ Il2rγ$^{tm1Wjl}$/SzJ (NOD/SCID-IL-2rγc-null, NSG) (originally obtained from Jackson Labs) mice were bred in the animal resource center at the British Columbia Cancer Research Centre. All mouse experimental procedures were carried out in accordance with Canadian Council on Animal Care guidelines with approval from the University of British Columbia.

Xenotransplantation and In Vivo Tracking of Transduced Human Cells in Mice

In xenotransplant studies, 8-12 week old NSG mice were sublethally irradiated (315 cGy of $^{137}$Cs γ-rays) 24 hours prior to transplantation. In competitive repopulation assays each mouse was injected intravenously with the progeny of 20,000 CD34+ CB cells transduced in the presence of Cmpd1 and 20,000 in the presence of DMSO. For limit dilution experiment mice received either the progeny of 20,000, 4,000 or 800 CD34+ CB cells transduced in the presence of Cmpd1 or DMSO. Human lympho-myeloid reconstitution in NSG bone marrow (BM) was monitored over 30 weeks by BM aspiration at 3, 12, 20 25 and 30 weeks post-transplant, and FACS analysis of GFP- and YFP-expressing human cells. Following red cell lysis, BM cells were incubated with a blocking reagent (PBS with 2% FBS, 5% of human serum, an anti CD16/CD32 antibody (2.4G2)), and stained with the following anti-human-specific antibodies: CD45-Alexa Fluor® 700 (clone HI30, Biolegend), CD33-PECY7 (clone WM-53, eBioscience), CD19-PE (clone, HIB19, Biolegend), CD20-PE (clone L27, StemCell Technologies). A minimum of 200,000 BM cells were analyzed per mouse. All flow cytometric analysis was performed using a LSRII Fortessa® (BD Biosciences). All flow cytometry data were analyzed using FlowJo® software (Version 8.8, TreeStar).

Transplantation and In Vivo Tracking of Transduced Macaque Mobilized BM Cells

G-CSF/SCF mobilized BM CD34+ cells were divided into two fractions. One fraction was transduced with mCherry expressing lentivirus in the presence of SR1 (1 μM) and cytokines (Steel Facor, FLT3-L and TPO) and the second fraction was transduced with GFP expressing lentivirus in the presence of SR1 and Cmpd1 (40 nM) and with the same cytokines. After expansion for 10 days in the presence or absence of Cmpd1 (40 nM), the two gene modified cell fractions were co-infused into the original HSC macaque donor after the animal received myeloablative preconditioning (1020 cGy irradiation).

Statistical Analysis

Results are shown as mean±SEM or SD and geometric±SD. Differences between groups were assessed using the Student t-test (paired or unpaired as appropriate) directly calculated on prism graphpad. *P values <0.05 were considered significant.

Figure 1:
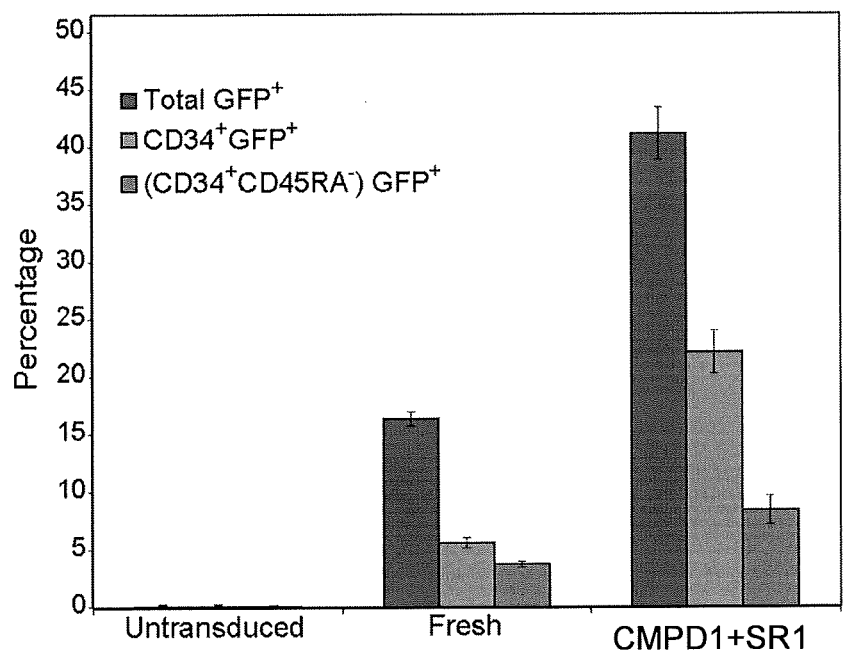
FIG. 1 shows that human $CD34^+$ cord blood (CB) cells expanded with Compound 1 (Cmpd1) and SR1 were more efficiently transduced than unmanipulated cells. Fresh or 8-day Cmpd1 (35 nM) and SR1 (500 nM) expanded $CD34^+$ CB cells were pre-stimulated for 24 hours and transduced with VSV-G lentivirus encoding GFP with MOI 10 for 16 hours, respectively. Cells were washed and stained with anti-human CD34 and CD45RA antibodies for FACS analysis after 72 hours post-transduction. Percentage of GFP-transduced cells in total (left bars), $CD34^+$ (middle bars) and $CD34^+CD45RA^-$ (right bars) populations in both conditions (Fresh vs. 8-day culture with Cmpd1+SR1) is presented.
Figure 2:
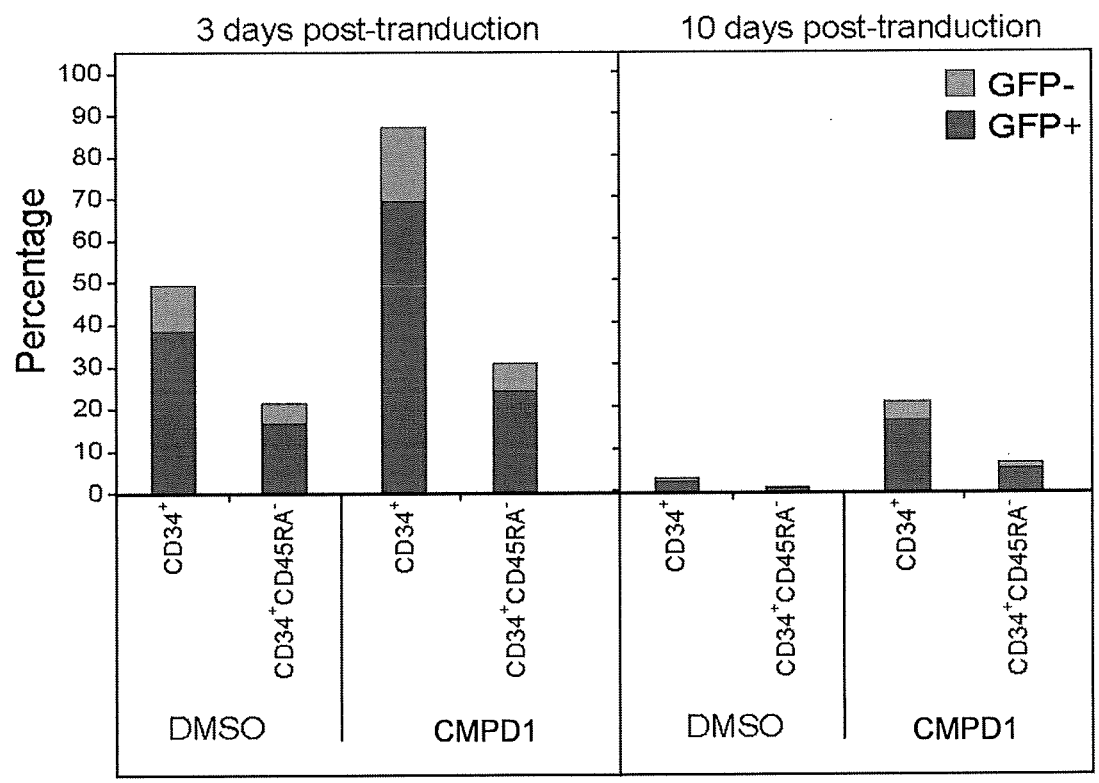
FIG. 2 shows that Cmpd1 treated cells showed higher percentages of the GFP-transduced CD34+ and CD34+ CD45RA-cells compared to DMSO controls. CD34+ CB cells were pre-stimulated for 48 hours and transduced with VSV-G or RDT114 lentivirus encoding GFP (MOI: 50 or 100) for 12 hours in the presence of vehicle (DMSO) or Cmpd1 (35 nM), respectively. Cells then were washed and cultured again in DMSO or Cmpd1. Flow cytometry analysis was performed to determine the GFP positive cells (dark gray) within the indicated population after 3 and 10 days post-transduction.
Figure 3A:
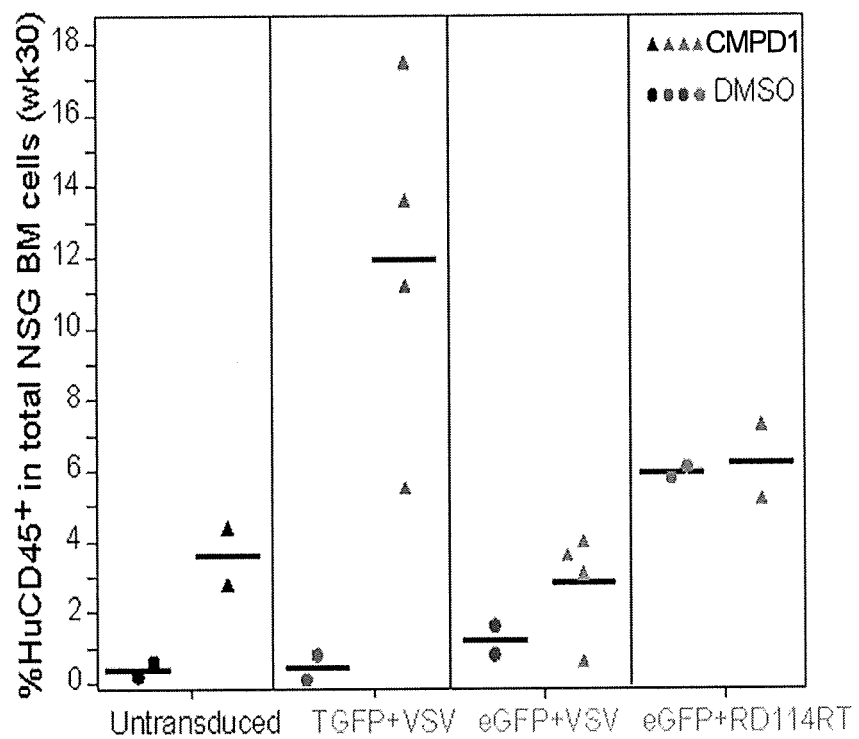
FIGS. 3A and 3B show that GFP-transduced and expanded Cmpd1-$CD34^+$CB cells exhibited a better engraftment potential of human CD45 engraftment compared to controls. The progeny of 1000 CD34+ CB cells transduced and expanded for 10 days with Cmpd1 (triangles) or DMSO (circles) controls (described in FIG. 2) were transplanted in sub-lethally irradiated (275 cGy) female NSG mice. Flow cytometry analysis of NSG bone marrow cells was performed after 30 weeks post-transplantation.
Figure 3B:
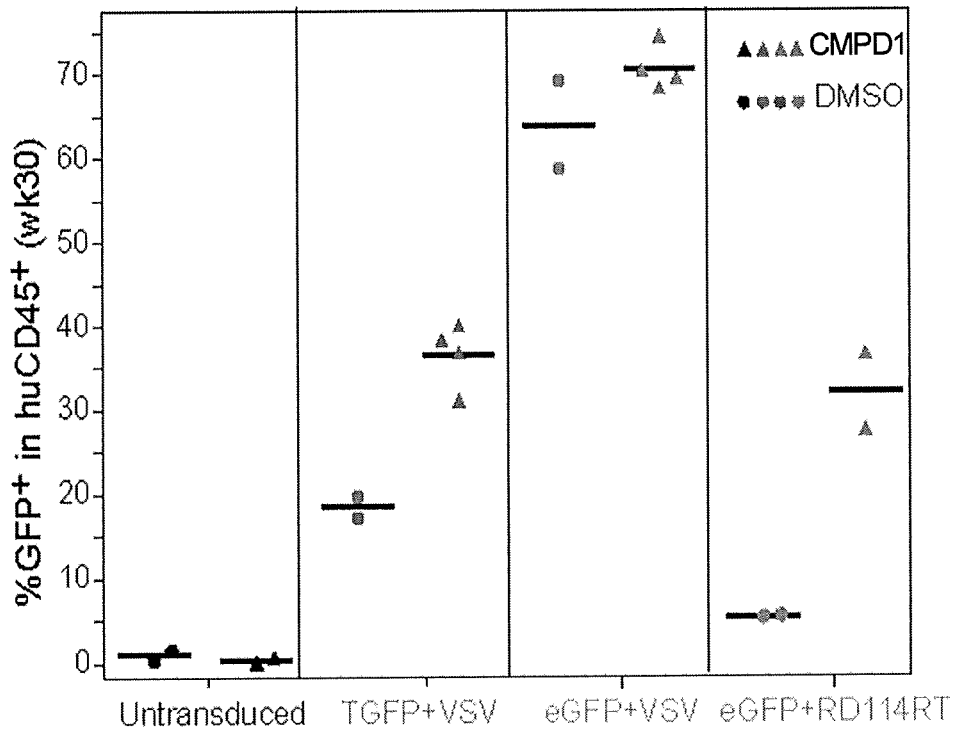

Example 1: Cmpd1 Enhances Lentiviral Gene Transfer Efficiency to Human Hematopoietic Cells FIG. 1 shows that human CD34+ cord blood (CB) cells expanded with Cmpd1 and SR1 were more efficiently transduced than unmanipulated cells. Cmpd1-treated cells showed higher percentages of the GFP-transduced CD34+ and CD34+CD45RA-cells compared to DMSO controls, both 3 days and 10 days post-transduction (FIG. 2). FIGS. 3 and 4 show that GFP-transduced and expanded Cmpd1-CD34+ CB cells showed a better engraftment potential of human CD45 engraftment compared to DMSO controls. Also, the data depicted in FIGS. 5A and 5B indicates that short term exposure of human hematopoietic cells to Cmpd1 can significantly enhance lentiviral-mediated gene transfer by some 70% as assessed 3 days post-infection on CD34+ stem/progenitor enriched cells from cord blood. This difference was statistically significant and not observed with SR1, another small molecule with capacity to stimulate expansion of primitive human hematopoietic cells.

Example 2: Short-Term Exposure to Cmpd1 During Only the Prestimulation or the Transduction Period was Sufficient to Enhance Lentiviral Mediated Gene Transfer to Primitive Human Hematopoietic Cells Over a Broad Range of Titres The results depicted in FIGS. 6A-6G demonstrate that the stimulatory effect of Cmpd1 on gene transfer is present across a wide range of viral titres. The effect is strong at lower viral concentrations. For example, gene transfer with viral concentration of $10^5$ is equivalent to that only achieved with ~100-fold higher viral concentrations in the absence of Cmpd1. Even at the highest viral concentrations used, there is an enhanced gene transfer when cells are exposed to Cmpd1 during prestimulation or transduction period. Importantly, this effect is evident on highly purified subsets of hematopoietic cells including CD34+CD38− and CD34+CD45RA− that include HSCs. Of further interest, even with this short term exposure to Cmpd1, there is an additional increase in the yield of various CD34+ subpopulations including transduced cells.

Example 3: Short-Term Exposure (22 h) to Cmpd1 Enhances Gene Transfer to Human HSCs The data depicted in FIGS. 7A to 7H shows that Cmpd1 enhances gene transfer to true lympho-myeloid long-term repopulating cells (HSC). By using a competitive transplantation approach, cells transduced with or without Cmpd1 were assessed for in vivo repopulation directly in the same recipient, providing unparalleled power to resolve differences. The magnitude of enhancement with Cmpd1 was 9-fold or even greater than evident from in vitro analysis of hematopoietic subpopulations. This may be due to an even greater impact of Cmpd1 on gene transfer to true HSC compared to later cells and a possible enhancement on yield of HSC even with the short (22 hr) culture period.

Example 4: Cmpd1 Stimulates the Enhancement of Gene Transfer to Human CD34+ CB Cells (In Vitro) and Human HSC in NSG Mice The results depicted in FIGS. 8A to 8E and FIGS. 9A to 9D confirms the significant impact of Cmpd1 on stimulating gene transfer to human cord blood HSC. FIGS. 9A to 9D confirm the enhancement of gene transfer to CB cells assessed in vitro and following transplantation using different source of CB and virus. Equivalent total levels of chimerism were observed in transplant recipients whether cells had been exposed to Cmpd1 or not and thus providing evidence that Cmpd1 did not have a significant effect on the yield of HSC. However, assessment of chimerism from marked, GFP cells, confirmed a significant increase when cells were transduced in the presence of Cmpd1. This increase was apparent over a range of transplant doses. The overall increase in gene transfer to HSC as assessed in this experiment was ~16-fold.

Example 5: Short Term Exposure to Cmpd1 for as Little as 2 Hours Increases Gene Transfer Efficiency to Primitive Human Hematopoietic Cells FIGS. 10A to 10Q shows that significant increases in gene transfer to CD34$^+$ cells and CD34$^+$ subsets were observed with exposure of cells for as little as 2 hrs at the beginning (condition IV) or end (condition V) of the transduction period. Maximum gene transfer and yield of transduced cells were achieved with exposure for 2 hrs at the end of the transduction period and were equivalent to that achieved with exposure during the whole prestimulation (16 hrs, condition III) period. Importantly these results were observed with bulk CD34$^+$ cells and subsets highly enriched for HSC/progenitors (CD34$^+$CD38$^-$CD45RA$^-$CD90$^+$). Also, the data depicted in FIGS. 11A and 11B shows that increased gene transfer and yields were observed under all conditions of exposure to Cmpd1 without prestimulation including as little as 2 hours exposure during the first 2 hours or last 2 hours of the transduction period.

Example 6: The Ability of Cmpd1 to Increase Gene Transfer Extends to Primitive Hematopoietic Cells of Adult Bone Marrow and Adult Mobilized Peripheral Blood Origins The data depicted in FIGS. 12A and 12B provides evidence that the ability of Cmpd1 to enhance gene transfer includes primitive hematopoietic cells of adult bone marrow and adult mobilized peripheral blood origins in addition to those in cord blood.

Example 7: Exposure to Cmpd1 Increases Gene Transfer Efficiency to CD34+ CB Cells Using Lentiviral Vectors with Different Envelopes, a Non-Integrating Lentivirus, and Under Different Conditions Cmpd1 enhanced gene transfer using lentiviruses pseudotyped (carrying envelope) with VSV-G and RD114 (FIGS. 13A and 13B), thus suggesting that Cmpd1 can enhance gene transfer over a broader range of pseudo typed virus. FIG. 13D further shows that Cmpd1 enhances the transient gene transfer efficiency of lentiviruses that are generated using catalytically inactive integrase and therefore rendering the lentivirus non-integrating (Integration Defective Lentivirus, IDLV). The results of FIGS. 14 and 14B demonstrate that the ability of Cmpd1 to stimulate gene transfer to primitive human hematopoietic cells is not restricted to a specific growth factor cocktail, but occurs in cells cultured in the presence of different growth factor combinations. Furthermore, the data depicted in FIGS. 15A to 15D demonstrates that the ability of Cmpd1 to stimulate gene transfer to primitive human hematopoietic cells extends to multiple lentiviral vectors, and thus is not restricted to a unique vector.

Example 8: Enhanced Gene Transfer to Primitive Human Hematopoietic Cells Correlates with Variants of Cmpd1 that are Active for Stimulation of Expansion FIGS. 16A and 16B shows that Cmpd1 and other variants of Cmpd1 known to be active for expansion of human CD34$^+$ cells (Cmpds 3 to 6) increase gene transfer efficiency to human CD34$^+$ CB cells and different CD34$^+$ subsets. Also, this enhancing effect was not observed with less active variants of Cmpd1 (Cmpds 7 and 8).

The following tables illustrate compounds and their efficacy in expanding human CD34$^+$ cells. Some of these compounds have been illustrated in WO 2013/110198 and PCT/ICA2015/050330.

TABLE 1

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 1 | [structure] | 1.72 | 454.2 | E |

TABLE 1-continued

Structure, analytical HPLC retention time, LCMS data and biological data of Examples.

| Cmpd number | Structure | HPLC $R_T$ (min) analytical | MS m/z (M + H)+ | Biological data (EC$_{50}$)* |
|---|---|---|---|---|
| 2 | [structure] | 1.38 | 368.2 | C |
| 3 | [structure] | 1.74 | 472.2717 | E |
| 4 | [structure] | 2.112 | 476.2499 | E |
| 5 | [structure] | 1.57 | 656.3529 | C |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 6 | 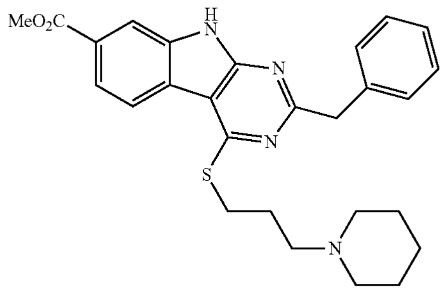 | 2.02 | 475.2155 | C |
| 7 | 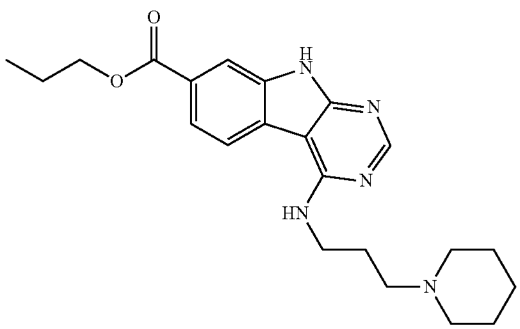 [SMILES: CCCOC(=O)c1ccc2c(c1)[nH]c1ncnc(NCCCN3CCCCC3)c12] | 1.67 | 396.2 | A |
| 8 | 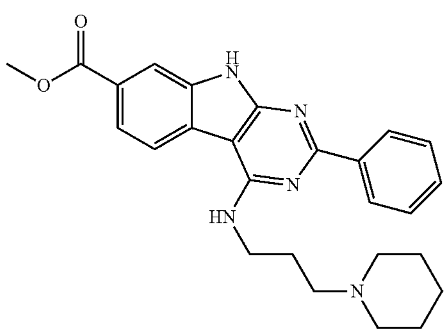 [SMILES: COC(=O)c1ccc2c(c1)[nH]c1nc(-c3ccccc3)nc(NCCCN3CCCCC3)c12] | 1.82 | 444.2435 | inactive |
| 9 | 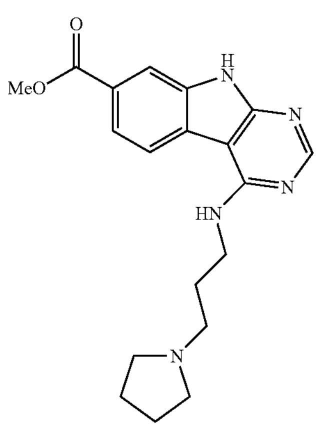 [SMILES: COC(=O)c1ccc2c(c1)[nH]c1ncnc(NCCCN3CCCC3)c12] | 1.35 | 354.2 | D |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 10 | 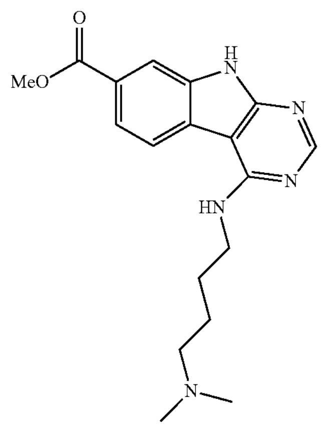 [SMILES: COC(=O)c1ccc2c(c1)[nH]c1ncnc(NCCCCN(C)C)c12] | 1.55 | 342.2 | C |
| 11 | 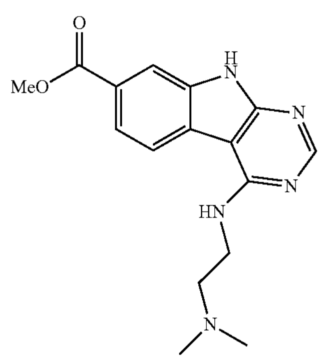 [SMILES: COC(=O)c1ccc2c(c1)[nH]c1ncnc(NCCN(C)C)c12] | 1.30 | 314.2 | D |
| 12 | 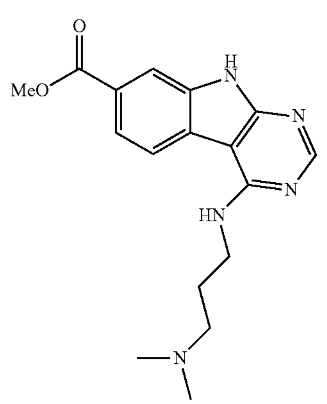 [SMILES: COC(=O)c1ccc2c(c1)[nH]c1ncnc(NCCCN(C)C)c12] | 1.29 | 328.2 | B |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 13 | 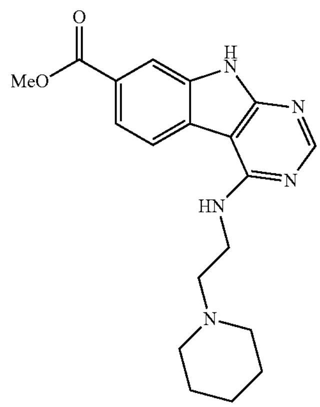 [SMILES: COC(=O)c1ccc2c(c1)[nH]c1ncnc(NCCN3CCCCC3)c12] | 1.41 | 354.2 | C |
| 14 | 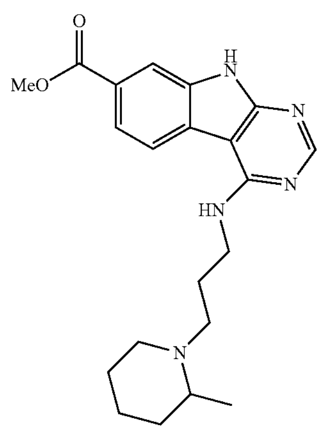 [SMILES: COC(=O)c1ccc2c(c1)[nH]c1ncnc(NCCCN3CCCCC3C)c12] | 1.43 | 382.2 | D |
| 15 | 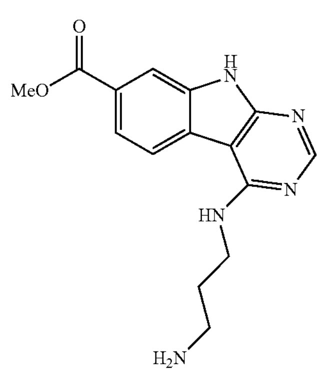 [SMILES: COC(=O)c1ccc2c(c1)[nH]c1ncnc(NCCCN)c12] | 1.34 | 300.2 | C |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 16 | 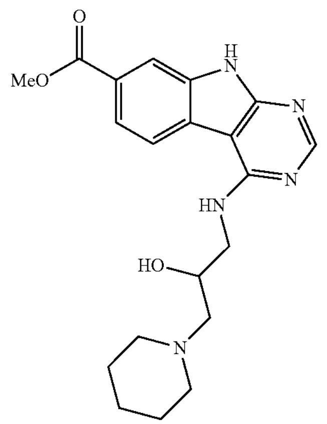 [SMILES: COC(=O)c1ccc2c(c1)[nH]c1ncnc(NCC(O)CN3CCCCC3)c12] | 1.35 | 384.2 | C |
| 17 | 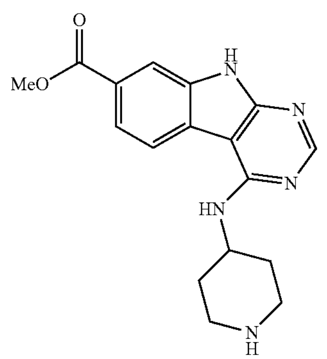 [SMILES: COC(=O)c1ccc2c(c1)[nH]c1ncnc(NC3CCNCC3)c12] | 1.34 | 326.2 | B |
| 18 | 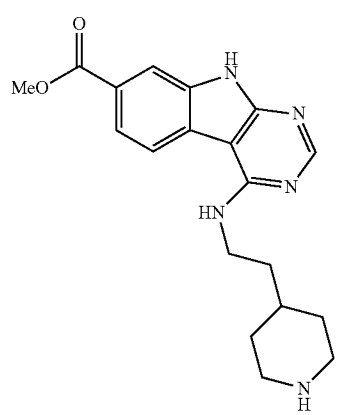 [SMILES: COC(=O)c1ccc2c(c1)[nH]c1ncnc(NCCC3CCNCC3)c12] | 1.40 | 354.2 | C |

TABLE 1-continued
Structure, analytical HPLC retention time, LCMS data and biological data of Examples.
| Cmpd number | Structure | HPLC R$_T$ (min) analytical | MS m/z (M + H)$^+$ | Biological data (EC$_{50}$)* |
|---|---|---|---|---|
| 19 | 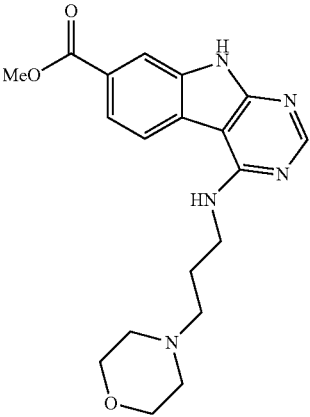 [SMILES: COC(=O)c1ccc2c(c1)[nH]c1ncnc(NCCCN3CCOCC3)c12] | 1.29 | 370.2 | A |
| 20 | 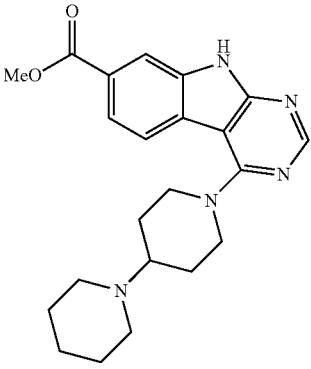 [SMILES: COC(=O)c1ccc2c(c1)[nH]c1ncnc(N3CCC(N4CCCCC4)CC3)c12] | 1.45 | 394.2 | D |
| 21 | 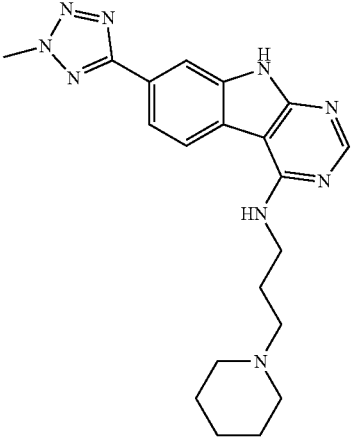 [SMILES: Cn1nnc(-c2ccc3c(c2)[nH]c2ncnc(NCCCN4CCCCC4)c23)n1] | 1.44 | 392.2 | D |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 22 | MeO$_2$C—[indole-pyrimidine core]—CH$_2$-(pyridin-3-yl); HN-(CH$_2$)$_3$-piperidine | 1.43 | 459.2 | E |
| 23 | MeO$_2$C—[indole-pyrimidine core]—CH$_2$-(pyridin-4-yl); HN-(CH$_2$)$_3$-piperidine | 1.78 | 459.2518 | C |
| 24 | MeO$_2$C—[indole-pyrimidine core]—CH$_2$-(pyrazin-2-yl); HN-(CH$_2$)$_3$-piperidine | 1.54 | 460.2 | B |
| 25 | MeO$_2$C—[indole-pyrimidine core]—CH$_2$-(thiophen-3-yl); HN-(CH$_2$)$_3$-piperidine | 2.068 | 464.2145 | E |
| 26 | MeO$_2$C—[indole-pyrimidine core]—CH$_2$-(3-iodo-5-bromophenyl); HN-(CH$_2$)$_3$-piperidine · TFA | 2.349 | 662.063 | E |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 27 | 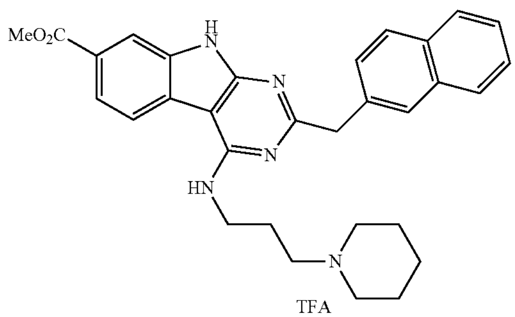 [SMILES: COC(=O)c1ccc2c(c1)[nH]c1nc(Cc3ccc4ccccc4c3)nc(NCCCN3CCCCC3)c12] | 2.206 | 508.2707 | D |
| 28 | 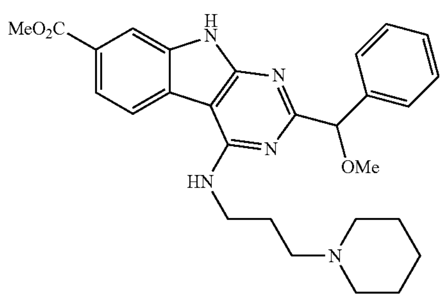 [SMILES: COC(=O)c1ccc2c(c1)[nH]c1nc(C(OC)c3ccccc3)nc(NCCCN3CCCCC3)c12] | 1.78 | 488.2665 | E |
| 29 | 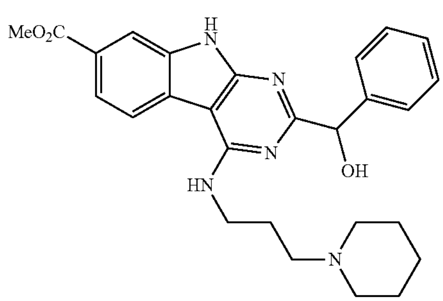 [SMILES: COC(=O)c1ccc2c(c1)[nH]c1nc(C(O)c3ccccc3)nc(NCCCN3CCCCC3)c12] | 1.68 | 474.2511 | F |
| 30 | 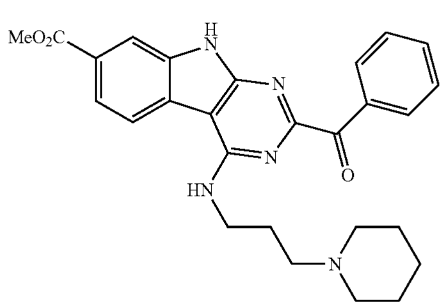 [SMILES: COC(=O)c1ccc2c(c1)[nH]c1nc(C(=O)c3ccccc3)nc(NCCCN3CCCCC3)c12] | 2.129 | 472.2342 | F |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 31 | 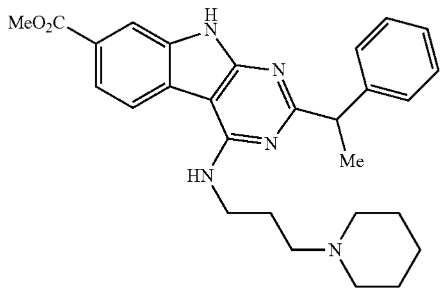 | 2.083 | 472.2724 | E |
| 32 | 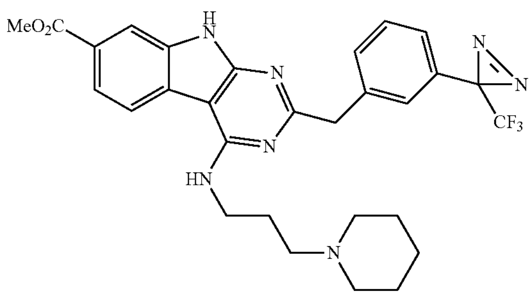 [SMILES: COC(=O)c1ccc2c(c1)[nH]c1nc(Cc3cccc(C4(C(F)(F)F)N=N4)c3)nc(NCCCN3CCCCC3)c12] | 2.05 | 566.2497 | E |
| 33 | 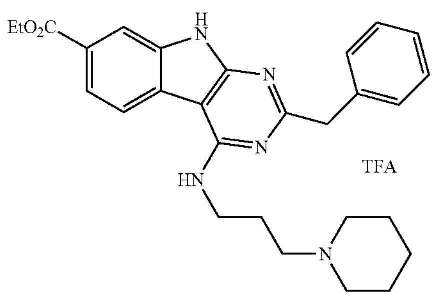 [SMILES: CCOC(=O)c1ccc2c(c1)[nH]c1nc(Cc3ccccc3)nc(NCCCN3CCCCC3)c12] | 2.152 | 472.2733 | F |
| 34 | 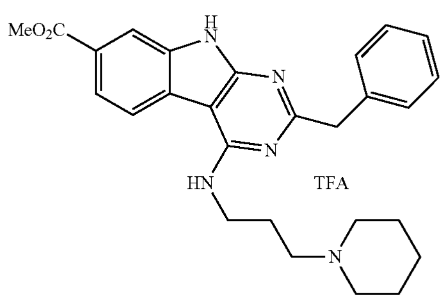 [SMILES: COC(=O)c1ccc2c(c1)[nH]c1nc(Cc3ccccc3)nc(NCCCN3CCCCC3)c12] | 2.052 | 458.2598 | E |
| 35 | 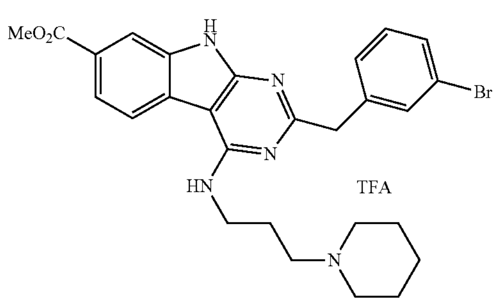 [SMILES: COC(=O)c1ccc2c(c1)[nH]c1nc(Cc3cccc(Br)c3)nc(NCCCN3CCCCC3)c12] | 2.194 | 538.1670 | E |

TABLE 1-continued

Structure, analytical HPLC retention time, LCMS data and biological data of Examples.

| Cmpd number | Structure | HPLC $R_T$ (min) analytical | MS m/z (M + H)⁺ | Biological data (EC$_{50}$)* |
|---|---|---|---|---|
| 36 | MeO₂C-[pyrimido-indole]-NH-(CH₂)₃-piperidine; 2-(2-methylbenzyl); TFA | 2.142 | 472.2756 | E |
| 37 | MeO₂C-[pyrimido-indole]-NH-(CH₂)₃-piperidine; 2-(4-methylbenzyl); TFA | 2.142 | 472.2740 | E |
| 38 | MeO₂C-[pyrimido-indole]-NH-(CH₂)₃-piperidine; 2-(3-methoxybenzyl); TFA | 2.070 | 488.2690 | E |
| 39 | MeO₂C-[pyrimido-indole]-NH-(CH₂)₃-piperidine; 2-(3-(trifluoroacetyl)benzyl) | 1.761.87 (hydrates) | 554.2384 | E |
| 40 | MeO₂C-[pyrimido-indole]-NH-(CH₂)₃-piperidine; 2-(3-(1-hydroxy-2,2,2-trifluoroethyl)benzyl) | 2.142 | 554.2 | E |

TABLE 1-continued
Structure, analytical HPLC retention time, LCMS data and biological data of Examples.
| Cmpd number | Structure | HPLC R$_T$ (min) analytical | MS m/z (M + H)$^+$ | Biological data (EC$_{50}$)* |
|---|---|---|---|---|
| 41 | 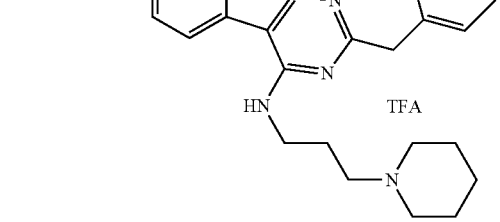 | 2.063 | 482.28 | E |
| 42 | 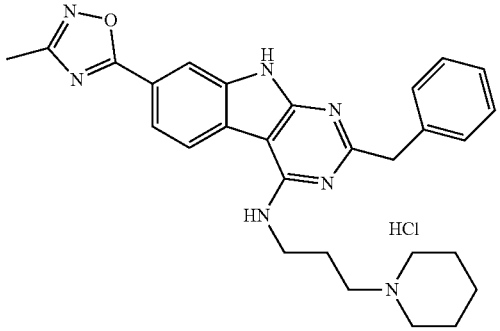 [SMILES: Cc1noc(-c2ccc3c(c2)[nH]c2nc(Cc4ccccc4)nc(NCCCN4CCCCC4)c23)n1 ; Cl] | 1.79 | 482.2663 | F |
| 43 | 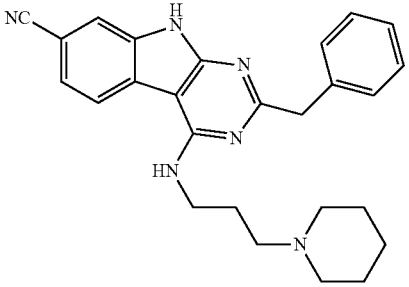 [SMILES: N#Cc1ccc2c(c1)[nH]c1nc(Cc3ccccc3)nc(NCCCN3CCCCC3)c12] | 1.68 | 425.2448 | C |
| 44 | 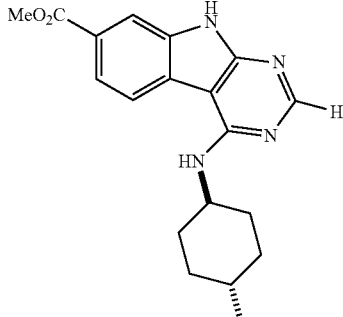 | 1.44 | 340.2 | D |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 45 | (structure) | 1.38 | 340.2 | C |
| 46 | (structure) •HCl | 1.71 | 482.2785 | E |
| 47 | (structure) | 1.92 | 459.2392 | B |
| 48 | (structure) | 1.75 | 457.2598 | F |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 49 | 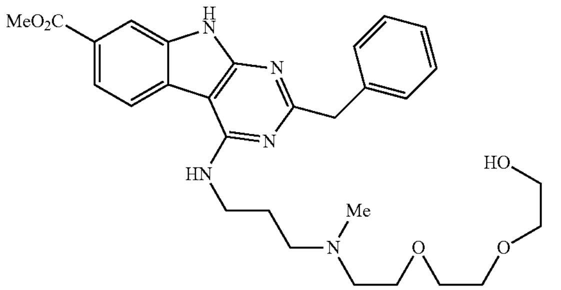 [SMILES: COC(=O)c1ccc2c(c1)[nH]c1nc(Cc3ccccc3)nc(NCCCN(C)CCOCCOCCO)c12] | 2.035 | 536.2867 | E |
| 50 | 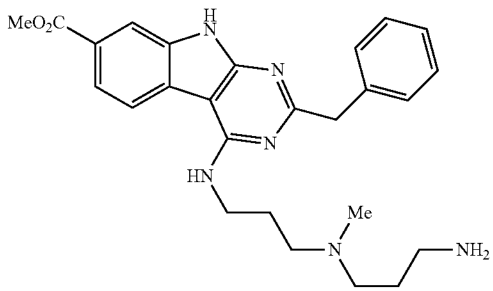 [SMILES: COC(=O)c1ccc2c(c1)[nH]c1nc(Cc3ccccc3)nc(NCCCN(C)CCCN)c12] | 1.63 | 461.2 | E |
| 51 | 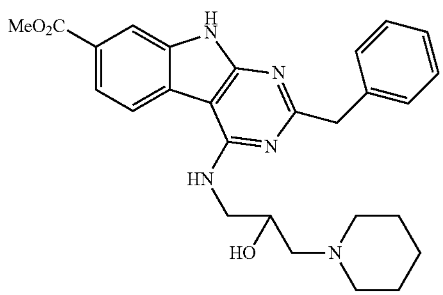 [SMILES: COC(=O)c1ccc2c(c1)[nH]c1nc(Cc3ccccc3)nc(NCC(O)CN3CCCCC3)c12] | 1.70 | 474.2476 | E |
| 52 | 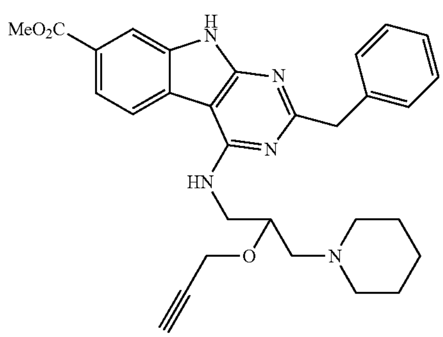 [SMILES: C#CCOC(CNc1nc(Cc2ccccc2)nc2[nH]c3cc(C(=O)OC)ccc3c12)CN1CCCCC1] | 1.85 | 512.2632 | E |
| 53 | 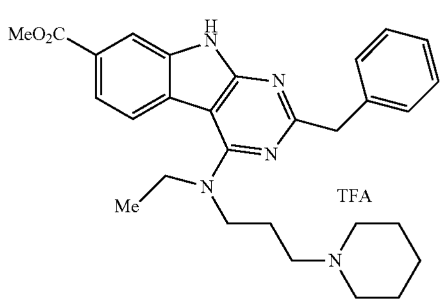 [SMILES: CCN(CCCN1CCCCC1)c1nc(Cc2ccccc2)nc2[nH]c3cc(C(=O)OC)ccc3c12] | 2.161 | 586.2839 | A |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 54 | 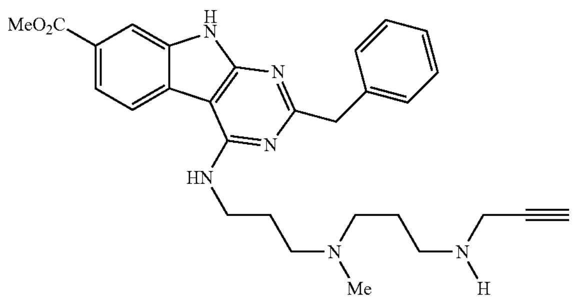 [SMILES: C#CCNCCCN(C)CCCNc1nc(Cc2ccccc2)nc2[nH]c3cc(C(=O)OC)ccc3c12] | 1.65 | 499.2823 | F |
| 55 | 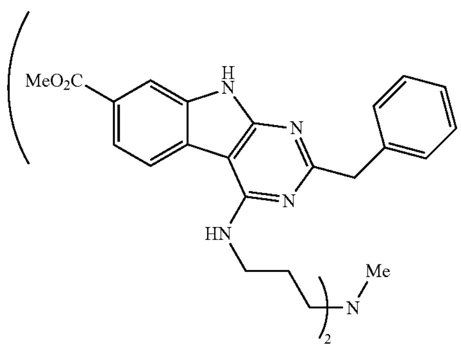 [SMILES: CNCCCNc1nc(Cc2ccccc2)nc2[nH]c3cc(C(=O)OC)ccc3c12] | 2.01 | 776.3 | E |
| 56 | 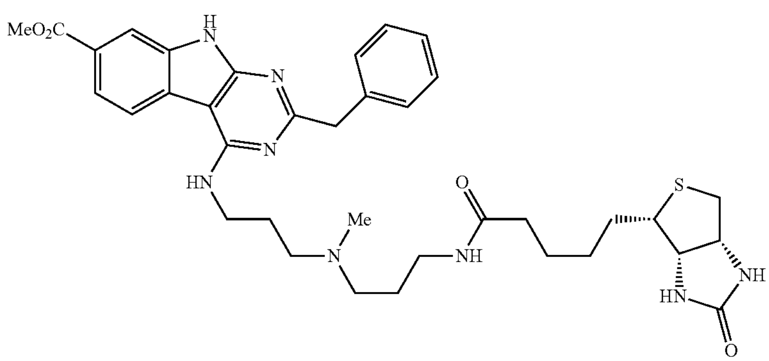 [SMILES: COC(=O)c1ccc2c(c1)[nH]c1nc(Cc3ccccc3)nc(NCCCN(C)CCCNC(=O)CCCC[C@@H]3SC[C@@H]4NC(=O)N[C@@H]43)c12] | 1.70 | 687.3 | C |
| 57 | 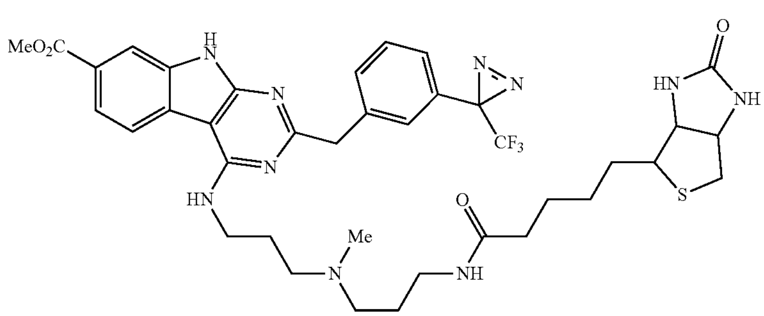 [SMILES: COC(=O)c1ccc2c(c1)[nH]c1nc(Cc3cccc(C4(C(F)(F)F)N=N4)c3)nc(NCCCN(C)CCCNC(=O)CCCCC3SCC4NC(=O)NC43)c12] | 2.06 | 795.3368 | F |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 58 | [Structure with MeO$_2$C group, indole-fused pyrimidine with Me substituent and HN-propyl-piperidine] | 1.46 | 382.2 | A |
| 59 | [Structure with MeHN-C(=O) group, indole-fused pyrimidine with benzyl substituent and HN-propyl-piperidine] | 1.53 | 457.2708 | A |
| 60 | [Structure with MeO$_2$C group, pyridine-fused pyrrolopyrimidine with CH$_2$Ph substituent and HN-propyl-piperidine] | 1.74 | 459.2 | C |
| 61 | [Structure with MeO$_2$C group, pyridine-fused pyrrolopyrimidine with thienylmethyl substituent and HN-propyl-piperidine] | 1.71 | 465.2 | C |
| 62 | [Structure with MeO$_2$C group, pyridine-fused pyrrolopyrimidine with thienylmethyl substituent and S-propyl-piperidine] | 1.82 | 482.2 | B |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 63 | 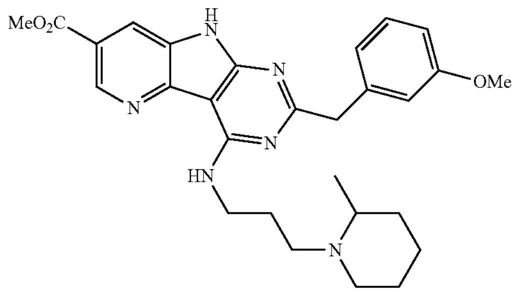 [SMILES: COC(=O)c1cnc2c(c1)[nH]c1nc(Cc3cccc(OC)c3)nc(NCCCN3CCCCC3C)c12] | 1.81 | 503.3 | C |
| 64 | 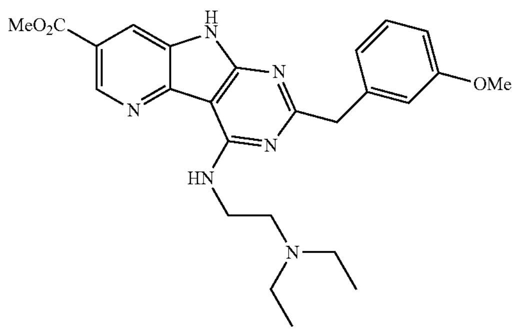 [SMILES: CCN(CC)CCNc1nc(Cc2cccc(OC)c2)nc2[nH]c3cc(C(=O)OC)cnc3c12] | 1.77 | 463.2 | B |
| 65 | 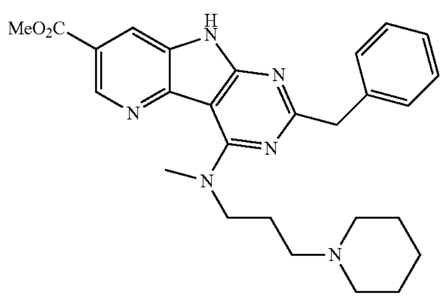 [SMILES: COC(=O)c1cnc2c(c1)[nH]c1nc(Cc3ccccc3)nc(N(C)CCCN3CCCCC3)c12] | 1.78 | 473.3 | E |
| 66 | 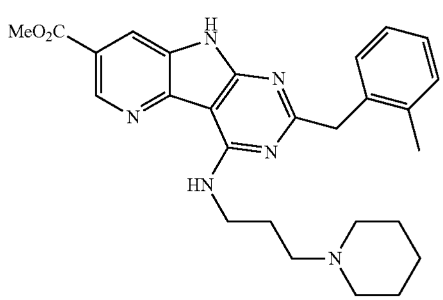 [SMILES: COC(=O)c1cnc2c(c1)[nH]c1nc(Cc3ccccc3C)nc(NCCCN3CCCCC3)c12] | 1.82 | 473.4 | C |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 67 | 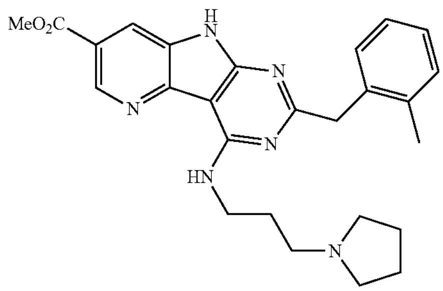 [SMILES: COC(=O)c1cnc2c(c1)[nH]c1nc(Cc3ccccc3C)nc(NCCCN3CCCC3)c12] | 1.78 | 459.3 | C |
| 68 | 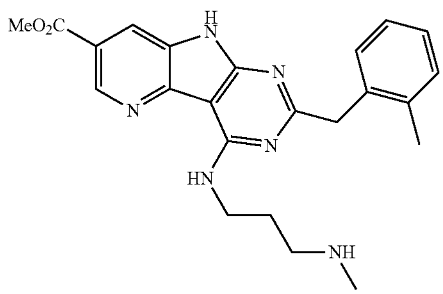 [SMILES: CNCCCNc1nc(Cc2ccccc2C)nc2[nH]c3cc(C(=O)OC)cnc3c12] | 1.81 | 419.3 | B |
| 69 | 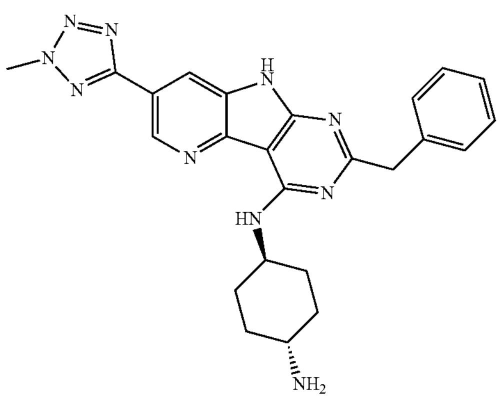 [SMILES: Cn1nnc(-c2cnc3c(c2)[nH]c2nc(Cc4ccccc4)nc(N[C@H]4CC[C@H](N)CC4)c23)n1] | 1.78 | 455.3 | C |
| 70 | 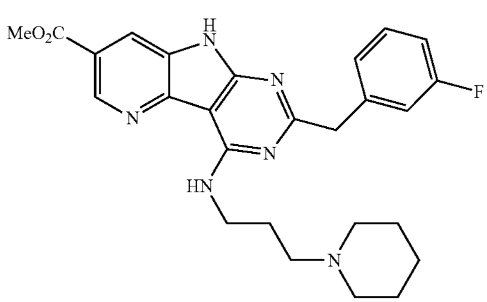 [SMILES: COC(=O)c1cnc2c(c1)[nH]c1nc(Cc3cccc(F)c3)nc(NCCCN3CCCCC3)c12] | 1.83 | 477.3 | A |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 71 | [structure] | 1.64 | 480.2 | C |
| 72 | [structure] | 1.78 | 423.2 | A |
| 73 | [structure] | 1.77 | 433.3 | B |
| 74 | [structure] | 1.76 | 445.3 | D |
| 75 | [structure] | 1.89 | 461.3 | C |

TABLE 1-continued

Structure, analytical HPLC retention time, LCMS data and biological data of Examples.

| Cmpd number | Structure | HPLC $R_T$ (min) analytical | MS m/z $(M + H)^+$ | Biological data $(EC_{50})$* |
|---|---|---|---|---|
| 76 | 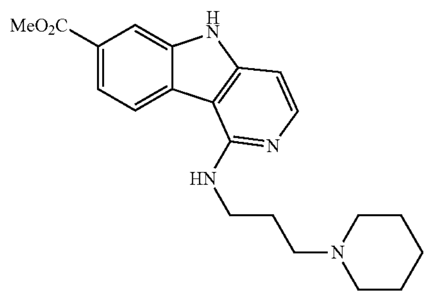 [SMILES: COC(=O)c1ccc2c(c1)[nH]c1ccnc(NCCCN3CCCCC3)c12] | 1.50 | 367.2 | A |
| 77 | 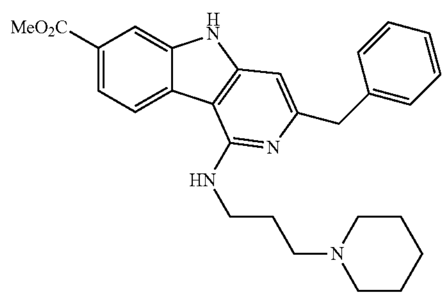 [SMILES: COC(=O)c1ccc2c(c1)[nH]c1cc(Cc3ccccc3)nc(NCCCN3CCCCC3)c12] | 1.64 | 457.2 | E |
| 78 | 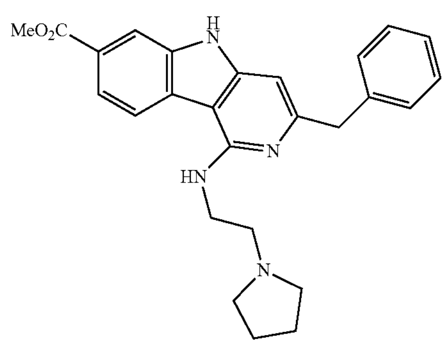 [SMILES: COC(=O)c1ccc2c(c1)[nH]c1cc(Cc3ccccc3)nc(NCCN3CCCC3)c12] | 1.62 | 429.2 | E |
| 79 | 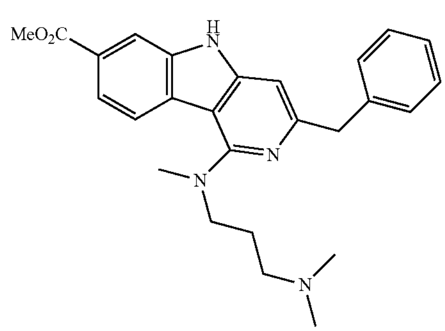 [SMILES: COC(=O)c1ccc2c(c1)[nH]c1cc(Cc3ccccc3)nc(N(C)CCCN(C)C)c12] | 1.63 | 431.2 | E |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 80 | 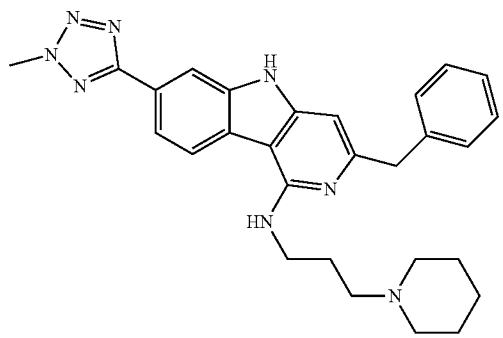 [SMILES: Cn1nnc(-c2ccc3c(c2)[nH]c2cc(Cc4ccccc4)nc(NCCCN4CCCCC4)c23)n1] | 1.63 | 481.4 | D |
| 81 | 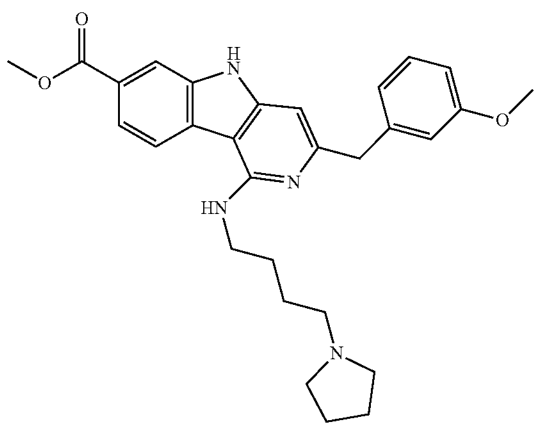 | 1.67 | 487.3 | E |
| 82 | 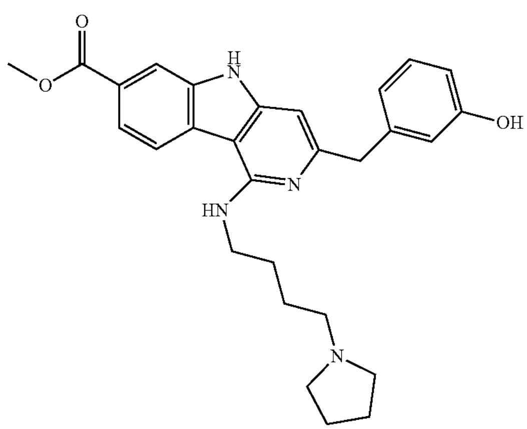 [SMILES: COC(=O)c1ccc2c(c1)[nH]c1cc(Cc3cccc(O)c3)nc(NCCCCN3CCCC3)c12] | 1.76 | 473.3 | E |
| 83 | 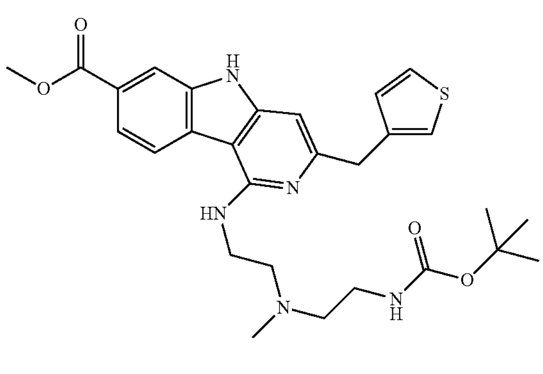 [SMILES: COC(=O)c1ccc2c(c1)[nH]c1cc(Cc3ccsc3)nc(NCCN(C)CCNC(=O)OC(C)(C)C)c12] | 1.72 | 538.2 | A |

TABLE 1-continued

Structure, analytical HPLC retention time, LCMS data and biological data of Examples.

| Cmpd number | Structure | HPLC $R_T$ (min) analytical | MS m/z (M + H)$^+$ | Biological data (EC$_{50}$)* |
|---|---|---|---|---|
| 84 | 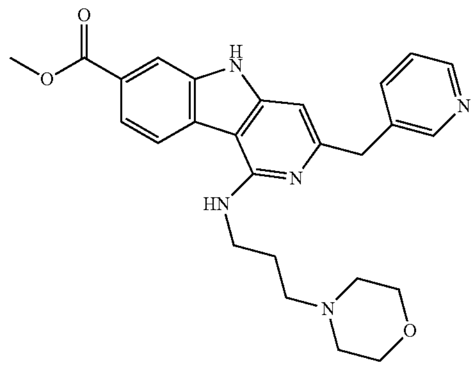 [SMILES: COC(=O)c1ccc2c(c1)[nH]c1cc(Cc3cccnc3)nc(NCCCN3CCOCC3)c12] | 1.12 | 460.3 | B |
| 85 | 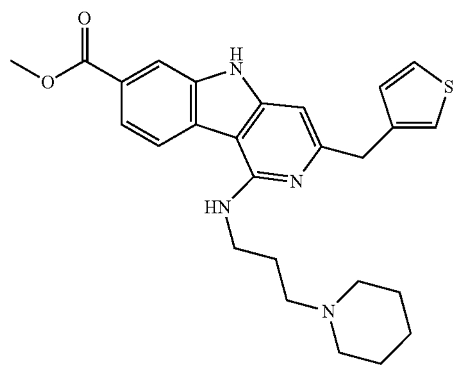 [SMILES: COC(=O)c1ccc2c(c1)[nH]c1cc(Cc3ccsc3)nc(NCCCN3CCCCC3)c12] | 1.58 | 463.2 | D |
| 86 | 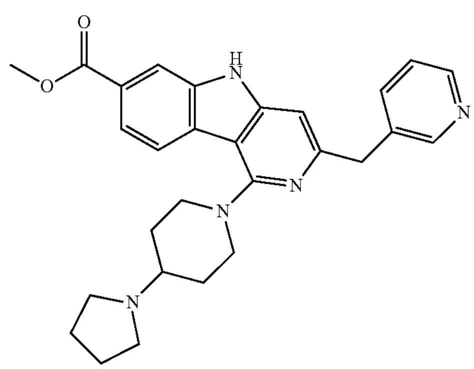 [SMILES: COC(=O)c1ccc2c(c1)[nH]c1cc(Cc3cccnc3)nc(N3CCC(N4CCCC4)CC3)c12] | 1.22 | 470.2 | A |
| 87 | 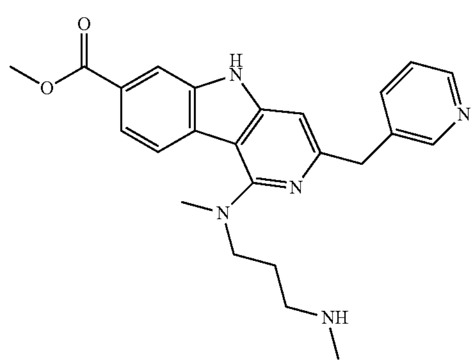 [SMILES: CNCCCN(C)c1nc(Cc2cccnc2)cc2[nH]c3cc(C(=O)OC)ccc3c12] | 1.18 | 418.2 | A |

TABLE 1-continued

Structure, analytical HPLC retention time, LCMS data and biological data of Examples.

| Cmpd number | Structure | HPLC R$_T$ (min) analytical | MS m/z (M + H)$^+$ | Biological data (EC$_{50}$)* |
|---|---|---|---|---|
| 88 | 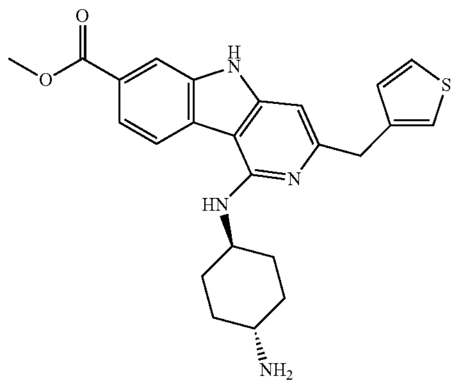 [SMILES: COC(=O)c1ccc2c(c1)[nH]c1cc(Cc3ccsc3)nc(N[C@H]3CC[C@H](N)CC3)c12] | 1.64 | 435.1 | D |
| 89 | 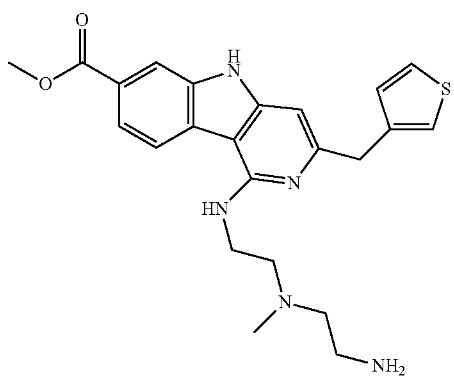 [SMILES: COC(=O)c1ccc2c(c1)[nH]c1cc(Cc3ccsc3)nc(NCCN(C)CCN)c12] | 1.56 | 438.2 | C |
| 90 | 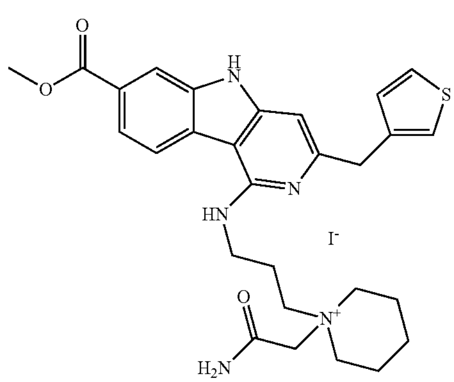 [SMILES: COC(=O)c1ccc2c(c1)[nH]c1cc(Cc3ccsc3)nc(NCCC[N+]3(CC(N)=O)CCCCC3)c12 ; [I-]] | 1.90 | 473.2 | E |

The EC$_{50}$ is defined as the concentration that results in a 50% increase in CD34$^+$CD45RA$^-$ cell count compared to vehicle cultures (DMSO).

*EC$_{50}$: A >1000 nM; B = 500-1000 nM; C = 250-500 nM; D = 100-250; E = <100 nM; F = compound showed >1.3 fold expansion.

Example 9: Cmpd1 Enhances the Transduction and Expansion of Gene-Modified CD34+ and LT-HSC Like Cells from Macaque Bone Marrow FIGS. 17A to 17C show that the proportion of primate CD45+ cells in the blood of transplanted mice after transplantation is increased in the presence of Cmpd1, an effect that is not obtained with SR1. FIGS. 18A to 18G and 19A to 19E show that there is an enhanced percentage of marked monkey cells after transduction in the presence of Cmpd1; increased yield of transduced CD34+ cells when cell infected and then culture for 7 days in presence of Cmpd1; and increased proportions of marked cells in monkeys transplanted with cells transduced and expanded in vitro in the presence of Cmpd1.

Example 10: Cmpd1 Cooperates with Rapamycin to Enhance Lentiviral Gene Transfer Efficiency to Human Hematopoietic Cells FIGS. 20A to 20E show that the increase in lentiviral gene transfer to CD34+ cells and CD34+ subsets is higher in cells treated with a combination of Cmpd1 and Rapamycin, relative to cells treated with Cmpd1 only or Rapamycin only, indicating that these two compounds cooperate to enhance lentiviral gene transfer efficiency to human hematopoietic cells.

Example 11: Synthetic Methodology

The synthetic methodology of Compounds 1 to 4 is presented in WO 2013/110198. For compounds 5 to 8, the following synthetic methodology applies. The synthetic methodology outlined below relates to embodiments of the invention wherein substituent Z is at the 7-position of the pyrimido indole nucleus. As will be understood by a skilled person, a similar synthetic methodology can be performed, with variations that are apparent to such person, for embodiments of the invention wherein substituent Z is at a different position, such as for example at the 5, 8 or 6-position, particularly at the 6-position.

Scheme 1 describes the synthesis of the common precursor (1-VI) to the compounds of the present invention. In the first step an aryl fluoride 1-I is treated with an alkyl cyanoacetate 1-II in the presence of a base such as, but not limited to, sodium hydride. The resulting product 1-III is then treated with a reducing agent such as, but not limited to, zinc dust in acetic acid to provide amino indoles 1-IV which are converted to the pyrimidines 1-V upon treatment with formamide and ammonium formate. Compounds 1-V are treated with reagents such as phosphoryl chloride or phosphoryl bromide to provide the reactive intermediates 1-VI which are treated with amines 1-VII to provide the compounds 1-VIII of the present invention.

Scheme 1

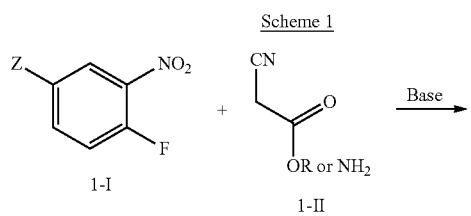

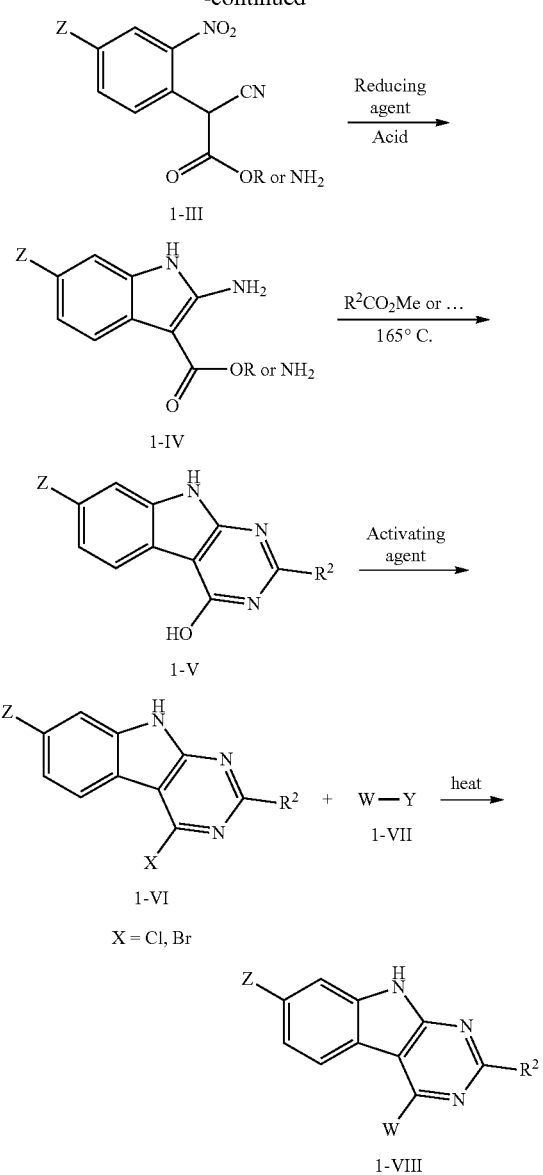

Examples

General

Reported HPLC retention time are for reverse-phase HPLC (Agilent, 1200 series) using the following conditions Solvent A: MeOH:$H_2O$:TFA (5:95:0.05); Solvent B: MeOH:$H_2O$:TFA (95:5:0.05); flow: 3.0 mL/min; gradient 0 to 100% B in 2.0 minutes; column: ZorbaxC18, 3.5 microns, 4.6×30 mm: wavelength 220 nm.

Mass spectra were recorded on a 6210 G1969A LC/MSD TOF spectrometer from Agilent Technologies or on a Quadrupole LC/MS Model G6120B from Agilent Technologies using the following LC conditions: Solvent A: AcCN:$H_2O$: HCOOH (5:95:0.05); Solvent B: AcCN:$H_2O$:HCOOH (95:5:0.05); gradient 0 to 100% B in 2.0 minutes; flow: 0.3 mL/min; column: ZorbaxC18, 3.5 microns, 2.1×30 mm; wavelength 220 nm.

Compound 5

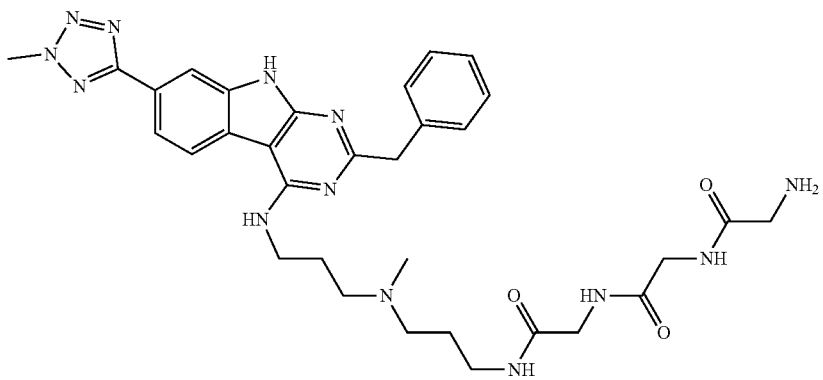 [SMILES: CN(CCCNC(=O)CNC(=O)CNC(=O)CN)CCCNc1nc(Cc2ccccc2)nc2[nH]c3cc(-c4nnn(C)n4)ccc3c12]

A mixture of 4-fluorobenzonitrile (5 g, 41.3 mmol), dibutyltin oxide (2.055 g, 8.26 mmol), and trimethylsilyl azide (8.22 mL, 61.9 mmol) in toluene (165 mL) was heated to 100° C. and stirred for 16.5 hours. After cooling to room temperature, the organic layer was extracted with NaOH 1M (83 mL) and the aqueous layer was washed with EtOAc (2×85 mL). The aqueous layer was acidified with HCl 2M (41.3 mL) to pH 2. The aqueous mixture was extracted twice with EtOAc (200 mL then 100 mL) and the combined organic layers were washed with brine (60 mL), dried over anh. MgSO$_4$, filtered and concentrated to dryness to give Intermediate 1A, (5-(4-fluorophenyl)-2H-tetrazole, 6.61 g, 98% yield) as a white solid; $^1$H NMR (400 MHz, DMSO-d$_6$) δ ppm 7.42-7.53 (m, 2H) 8.04-8.14 (m, 2H); MS m/z 165.2 (M+H)$^+$; HPLC>99.5%, RT=1.96 minutes.

A mixture of Intermediate 1A (6.61 g, 40.3 mmol), K$_2$CO$_3$ (6.68 g, 48.3 mmol), and iodomethane (3.02 mL, 48.3 mmol) in acetonitrile (115 mL) was heated to reflux (ca. 82° C.) for one hour. After cooling, the mixture was concentrated to dryness and the residue was partitioned between water (75 mL) and EtOAc (100 mL). The layers were separated, the aqueous layer was back-extracted with EtOAc (50 mL) and the combined organic layers were washed with water (50 mL) and brine (50 mL). The organic layer was dried over anh. MgSO$_4$, filtered and concentrated to give 9.5 g as a colorless oil that solidified upon standing. The residue was purified by flash chromatography to give 2 main products: Intermediate 1B (N2 isomer): 5-(4-fluorophenyl)-2-methyl-2H-tetrazole (5.09 g, 70.9% yield) as a white solid: No NOE observed between the methyl group at 4.42 ppm and the aromatic protons; $^1$H NMR (400 MHz, DMSO-d$_6$) δ ppm 4.42 (s, 3H) 7.33-7.45 (m, 2H) 8.03-8.14 (m, 2H); MS m/z 179.2 (M+H)$^+$; HPLC>99.5%, RT=1.75 minutes.

The N1 isomer: 5-(4-fluorophenyl)-1-methyl-1H-tetrazole (1.87 g, 26.1% yield) as a white solid: the NOE observed between the methyl group at 4.16 ppm and the two aromatic protons at 7.89-7.97 ppm confirms the structure; $^1$H NMR (400 MHz, DMSO-d$_6$) δ ppm 4.16 (s, 3H) 7.43-7.53 (m, 2H) 7.89-7.97 (m, 2H); MS m/z 179.2 (M+H)$^+$; HPLC>99.5%, RT=1.29 minutes.

A solution of Intermediate 1B (1 g, 5.61 mmol) in sulfuric acid (16.45 mL, 309 mmol) was cooled to 0° C. and then fuming nitric acid (0.288 mL, 6.17 mmol) was added dropwise. After 2.5 hours, more fuming nitric acid was added (0.065 mL, 1.403 mmol) and the mixture allowed to warm to 20° C. After 5 hours, the mixture was poured into a 2:1 ice-water mixture (150 mL) leading to the formation of a white suspension. After 30 minutes, the solid was filtered, washed with water (4×10 mL, until neutral pH of the washes), dried at 25° C. under high vacuum until constant weight to give 5-(4-fluoro-3-nitrophenyl)-2-methyl-2H-tetrazole (1.16 g, 93% yield) as an off-white solid; $^1$H NMR (400 MHz, DMSO-d$_6$) δ ppm 4.47 (s, 3H) 7.81 (dd, J=11.2, 8.8 Hz, 1H) 8.44 (ddd, J=8.7, 4.2, 2.3 Hz, 1H) 8.68 (dd, J=7.2, 2.2 Hz, 1H); MS m/z 224.2 (M+H)$^+$; HPLC 98.3%, RT=1.72 minutes.

To a cold (0° C.) suspension of sodium hydride 60% wt. in mineral oil (0.443 g, 11.08 mmol) in DMF (5.67 mL) was added a solution of 2-cyanoacetamide (0.888 g, 10.56 mmol) in DMF (2.268 mL) (Note: Hydrogen gas evolution). The resulting mixture was stirred at 0° C. for 30 minutes. Then a solution of 5-(4-fluoro-3-nitrophenyl)-2-methyl-2H-tetrazole (1.15 g, 5.15 mmol) in DMF (2.3 mL) was added to give a deep purple solution. After 3 hours, the reaction mixture was slowly poured into an ice-water mixture (33.0 mL) and conc. HCl (0.952 mL). The resulting yellow slurry was stirred for 30 minutes, the solid was filtered, washed with water (3×5 mL) and then with Hexane (2×5 mL), dried at 40° C. under high vacuum until constant weight to give Intermediate 1C (2-cyano-2-(4-(2-methyl-2H-tetrazol-5-yl)-2-nitrophenyl)acetamide) (1.41 g, 95% yield) as a yellow solid; $^1$H NMR (400 MHz, DMSO-d$_6$) δ ppm 4.49 (s, 3H) 5.77 (s, 1H) 7.77 (s, 1H) 7.95 (d, J=8.2 Hz, 1H) 8.03 (s, 1H) 8.51 (dd, J=8.2, 1.8 Hz, 1H) 8.70 (d, J=1.8 Hz, 1H); MS m/z 288.1 (M+H)$^+$; HPLC 96.4% @ 220 nm, RT=1.31 minutes.

Ferric chloride hexahydrate (2.82 g, 10.44 mmol) and zinc (2.276 g, 34.8 mmol) were added portionwise to a mixture of 2-cyano-2-(4-(2-methyl-2H-tetrazol-5-yl)-2-nitrophenyl)acetamide (1 g, 3.48 mmol) in DMF (8.71 mL) and water (8.71 mL) to give a yellow suspension which was heated to 100° C. for 1.25 hour. The mixture was then cooled to 20° C., diluted with MeOH (50.0 mL), filtered over Celite and concentrated under reduced pressure to ca. 20 mL (to remove most of the MeOH). Then the mixture was diluted with water (50 mL) and EtOAc (100 mL), stirred vigorously and filtered. The aqueous layer was extracted with EtOAc (2×50 mL) and the combined organic layers were washed with sat. NaHCO$_3$ (50 mL) and brine (50 mL). The organic layer was dried over anh. MgSO$_4$, filtered and concentrated to give 489 mg as a purple solid which was purified by flash chromatography to give Intermediate 1D (2-amino-6-(2-methyl-2H-tetrazol-5-yl)-1H-indole-3-carboxamide) (356 mg, 39.7% yield) as a purple solid; $^1$H NMR (400 MHz, DMSO-d$_6$) δ ppm 4.38 (s, 3H) 6.57 (s, 2H) 7.01 (s, 2H) 7.61-7.69 (m, 2H) 7.81 (s, 1H) 10.77 (s, 1H); MS m/z 258.2 (M+H)$^+$; HPLC ca. 78%, RT=1.34 minutes.

A mixture of Intermediate 1D (2-amino-6-(2-methyl-2H-tetrazol-5-yl)-1H-indole-3-carboxamide, 0.35 g, 1.361 mmol), methyl 2-phenylacetate (0.288 mL, 2.041 mmol) and sodium methoxide 25% wt. in MeOH (0.467 mL) in methanol (3.03 mL) was heated in a microwave oven to 140° C. for one hour. After cooling to room temperature and dilution with water (1 mL) and AcOH (4 mL) the mixture was stirred for 30 minutes to allow crystallization. The solid was filtered, washed with MeOH (5×1 mL) and dried at 40° C. under high vacuum until constant weight to give 2-benzyl-7-(2-methyl-2H-tetrazol-5-yl)-9H-pyrimido[4,5-b]indol-4-ol (220 mg, 45.2% yield) as a brown solid; $^1$H NMR (400 MHz, DMSO-d$_6$) δ ppm 4.03 (s, 2H) 4.43 (s, 3H) 7.24-7.29 (m, 1H) 7.34 (t, J=7.8 Hz, 2H) 7.37-7.43 (m, 2H) 7.92 (dd, J=8.0, 1.4 Hz, 1H) 8.04-8.10 (m, 2H) 12.38 (s, 1H) 12.47 (s, 1H); MS m/z 358.2 (M+H)$^+$; HPLC 82.9%, RT=1.89 minutes.

In a 2-5 mL microwave vial was added the crude product 2-benzyl-7-(2-methyl-2H-tetrazol-5-yl)-9H-pyrimido[4,5-b]indol-4-ol (0.220 g, 0.616 mmol) and POCl$_3$ (3.90 mL, 41.9 mmol) to give a brown suspension. The vial was placed in the microwave oven and heated to 175° C. for 15 minutes, then allowed to cool. The reaction mixture was then poured into water and ice mixture (80 ml), basified to pH 8 by slow addition of NaOH 50% wt (11 mL) and then EtOAc (80 mL). Some solids were filtered and the layers separated. The aqueous layer was extracted with EtOAc (80 mL) and the organic layer was dried over anh. MgSO$_4$, filtered and concentrated to dryness to give the corresponding chloro derivative: 2-benzyl-4-chloro-7-(2-methyl-2H-tetrazol-5-yl)-9H-pyrimido[4,5-b]indole (189 mg, 82% yield) as a brown solid; $^1$H NMR (400 MHz, DMSO-d$_6$) δ ppm 4.31 (s, 2H) 4.46 (s, 3H) 7.20-7.26 (m, 1H) 7.28-7.39 (m, 4H) 8.09 (dd, J=8.2, 1.2 Hz, 1H) 8.21-8.25 (m, 1H) 8.39 (d, J=8.2 Hz, 1H) 12.93 (s, 1H); MS m/z 376.2 (M+H)$^+$; HPLC 95.6%, RT=2.30 minutes.

A mixture of 2-benzyl-4-chloro-7-(2-methyl-2H-tetrazol-5-yl)-9H-pyrimido[4,5-b]indole prepared as described above (0.865 g, 2.302 mmol) and 3,3'-Diamino-N-methyl-dipropylamine (2.60 mL, 16.11 mmol) in MeOH (17.4 mL) was heated 30 minutes to 140° C. in a microwave oven. After cooling and evaporation of the solvent, the residue was purified by flash chromatography to give N1-(3-aminopropyl)-N3-(2-benzyl-7-(2-methyl-2H-tetrazol-5-yl)-9H-pyrimido[4,5-b]indol-4-yl)-N1-methylpropane-1,3-diamine (832 mg, 74% yield) as a yellow solid; $^1$H NMR (400 MHz, DMSO-d6) δ ppm 1.52 (quin, J=6.85 Hz, 2H) 1.80 (quin, J=6.85 Hz, 2H) 2.18 (s, 3H) 2.36 (t, J=7.24 Hz, 2H) 2.41 (t, J=6.65 Hz, 2H) 2.53-2.61 (m, 2H) 3.64 (q, J=6.52 Hz, 2H) 4.04 (s, 2H) 4.43 (s, 3H) 7.14-7.23 (m, 1H) 7.28 (t, J=7.43 Hz, 2H) 7.38 (d, J=7.43 Hz, 2H) 7.49 (t, J=5.09 Hz, 1H) 7.91 (d, J=8.22 Hz, 1H) 8.08 (s, 1H) 8.32 (d, J=8.22 Hz, 1H); HPLC 99.4% at 254 nm, RT 1.608 minutes; HRMS m/z 485.2884 (M+H)$^+$.

To a solution of 2,2-dimethyl-4,7,10-trioxo-3-oxa-5,8,11-triazatridecan-13-oic acid (0.224 g, 0.774 mmol) in DMF (3.00 mL) was added HATU (0.294 g, 0.774 mmol) and DIPEA (0.270 ml, 1.548 mmol). The solution was stirred for 10 minutes then N1-(3-aminopropyl)-N3-(2-benzyl-7-(2-methyl-2H-tetrazol-5-yl)-9H-pyrimido[4,5-b]indol-4-yl)-N1-methylpropane-1,3-diamine (0.300 g, 0.619 mmol) was added. Stirred at 20° C. for 3 hours. Added 2,2-dimethyl-4,7,10-trioxo-3-oxa-5,8,11-triazatridecan-13-oic acid (0.112 μg, 0.387 mmol), HATU (0.147 g, 0.387 mmol) and DIPEA (0.135 ml, 0.774 mmol) and stirred at 20° C. for 16 hours. The reaction mixture was poured into Water (30 mL). Extracted the aqueous layer with EtOAc (2×30 mL). The combined organic layers were washed with Water (20 mL) then with Brine (20 mL). The organic layer was dried over anh. MgSO$_4$, filtered and concentrated to give 764 mg as a yellow foam. The residue was purified by flash chromatography to give tert-butyl (16-((2-benzyl-7-(2-methyl-2H-tetrazol-5-yl)-9H-pyrimido[4,5-b]indol-4-yl)amino)-13-methyl-2,5,8-trioxo-3,6,9,13-tetraazahexadecyl)carbamate (380 mg, 81% yield) as a yellow solid; $^1$H NMR (400 MHz, DMSO-d6) δ ppm 1.36 (s, 9H) 1.52-1.65 (m, 2H) 1.73-1.86 (m, 2H) 2.18 (br. s., 3H) 2.33 (br. s., 2H) 2.41 (br. s., 2H) 3.02-3.14 (m, 2H) 3.57 (d, J=5.87 Hz, 2H) 3.65 (m, J=5.50 Hz, 4H) 3.72 (d, J=5.48 Hz, 2H) 4.05 (s, 2H) 4.43 (s, 3H) 7.01 (t, J=5.48 Hz, 1H) 7.15-7.22 (m, 1H) 7.28 (t, J=7.63 Hz, 2H) 7.37 (d, J=7.43 Hz, 2H) 7.43 (t, J=5.28 Hz, 1H) 7.72 (br. s., 1H) 7.91 (dd, J=8.22, 1.17 Hz, 1H) 8.08 (s, 3H) 8.33 (d, J=8.22 Hz, 1H) 12.00 (s, 1H); HPLC 98.1% at 254 nm, Rt 1.74 minutes; MS m/z 756.4 (M+H)$^+$.

To a solution of tert-butyl (16-((2-benzyl-7-(2-methyl-2H-tetrazol-5-yl)-9H-pyrimido[4,5-b]indol-4-yl)amino)-13-methyl-2,5,8-trioxo-3,6,9,13-tetraazahexadecyl)carbamate (0.380 μg, 0.503 mmol) in CH$_2$Cl$_2$ (8.00 ml) was added trifluoroacetic acid (2.000 ml, 26.0 mmol). The reaction mixture was stirred for 30 minutes. Toluene (5 mL) was added and the mixture concentrated to dryness to give 580 mg as a yellow foam. The residue was purified by flash chromatography to give 2-amino-N-(2-((2-((3-((3-((2-benzyl-7-(2-methyl-2H-tetrazol-5-yl)-9H-pyrimido[4,5-b]indol-4-yl)amino)propyl)(methyl)amino)propyl)amino)-2-oxoethyl)amino)-2-oxoethyl)acetamide (340 mg, 100% yield) as a yellow foam; $^1$H NMR (400 MHz, DMSO-d6) δ ppm 1.63 (dt, J=14.28, 6.95 Hz, 2H) 1.87 (dt, J=13.99, 6.90 Hz, 2H) 2.33 (s, 3H) 2.52-2.56 (m, 2H) 2.61 (br. t, J=6.70, 6.70 Hz, 2H) 3.05-3.14 (m, 2H) 3.55 (s, 2H) 3.60-3.71 (m, 4H) 3.83 (d, J=5.48 Hz, 2H) 4.05 (s, 2H) 4.43 (s, 3H) 7.15-7.23 (m, 1H) 7.28 (t, J=7.43 Hz, 2H) 7.38 (d, J=7.43 Hz, 2H) 7.43 (t, J=5.48 Hz, 1H) 7.87 (t, J=5.67 Hz, 1H) 7.91 (dd, J=8.22, 1.17 Hz, 1H) 8.08 (d, J=1.20 Hz, 1H) 8.22 (t, J=5.67 Hz, 1H) 8.35 (d, J=8.22 Hz, 1H) 8.55 (t, J=5.48 Hz, 1H) 12.02 (br. s., 1H); HPLC 99.4% at 254 nm, Rt 1.57 minutes; HRMS m/z 656.3529 (M+H)$^+$.

Compound 6

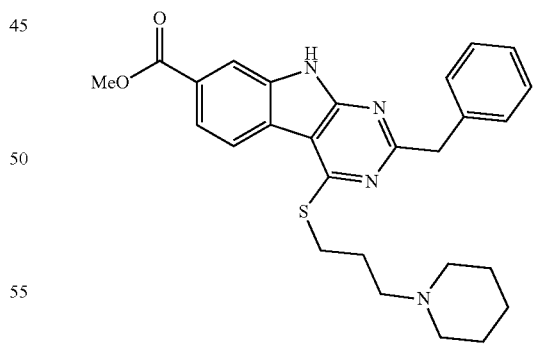

To a suspension of 1-(3-chloropropyl)piperidine hydrochloride (0.500 g, 2.52 mmol) in THF (14.83 ml, 181 mmol) was added triisopropylsilanethiol (1.092 ml, 5.05 mmol) and tetrabutylammonium iodide (0.093 g, 0.252 mmol). Sodium hydride 60% wt. in Mineral Oil (0.252 g, 6.31 mmol) was added portionwise. The resulting white suspension was heated to 50° C. and stirred for 18.5 hours. Cooled to 20° C. and diluted the reaction mixture with Water (15 mL). The mixture was extracted with EtOAc (4×15 mL). The combined organic layers were washed with Water (2×15 mL) then with Brine (15 mL). The organic layer was dried over anh. MgSO$_4$, filtered and concentrated to give 1.51 g as an orange oil. The residue was purified by flash chromatography to give Intermediate 2A, 1-(3-((triisopropylsilyl)thio) propyl)piperidine (714 mg, 90% yield) as a colorless oil. $^1$H NMR (400 MHz, DMSO-d$_6$) δ ppm 1.06 (d, J=7.0 Hz, 18H) 1.14-1.29 (m, 3H) 1.36 (m, J=5.1 Hz, 2H) 1.46 (quin, J=5.4 Hz, 4H) 1.65 (quin, J=7.0 Hz, 2H) 2.29 (m, J=6.7 Hz, 6H) 2.53 (t, J=7.3 Hz, 2H); MS m/z 316.2 (M+H)$^+$; HPLC>95%, RT=2.19 minutes.

NaH 60% wt. in mineral oil (3.41 g, 85 mmol) was added portionwise to a cold solution of 2-cyanoacetamide (7.18 g, 85 mmol) in DMF (53 mL). After 30 minutes at room temperature, a solution of methyl 4-fluoro-3-nitrobenzoate (8.5 g, 42.7 mmol) in DMF (15 mL) was added dropwise. After 3 hours, a mixture of ice, water and 12 mL HCl (10%) were added. The resulting solid was filtered, rinsed with water and dried under high vacuum to give 9.1 g of methyl 4-(2-amino-1-cyano-2-oxoethyl)-3-nitrobenzoate: $^1$H NMR (400 MHz, DMSO-d$_6$) δ ppm 3.93 (s, 3H) 5.78 (s, 1H) 7.77 (s, 1H) 7.91 (d, J=7.83 Hz, 1H) 8.04 (s, 1H) 8.39 (dd, J=8.02, 1.76 Hz, 1H) 8.56 (d, J=1.56 Hz, 1H).

Ferric chloride hexahydrate (1.540 g, 5.70 mmol) and zinc (1.242 g, 19.00 mmol) were added to a solution of the crude cyano-amide prepared above (0.5 g, 1.900 mmol) in DMF (4.75 mL) and water (4.75 mL) to give a yellow suspension. After the exotherm, the mixture was heated to 100° C. for 45 minutes and then slowly cooled to 20° C. and stirred for 22 hours. The solid was filtered, washed with DMF (3×3 mL) and the filtrate was diluted with water (40 mL) while stirring at 0° C. The solid was filtered and the cake washed with water (2×5 mL). The solid contains mostly impurities. The aqueous layer was extracted with EtOAc (3×50 mL) and the combined organic layers were washed with water (50 mL) and then with brine (30 mL). The organic layer was dried over anh. MgSO$_4$, filtered and concentrated to give 287 mg as a brown solid which was treated with acetone (6 mL) to give a solid suspension which was diluted with hexane (5 mL). Then the solid was collected and dried at 40° C. under high vacuum until constant weight to give Intermediate 2C methyl 2-amino-3-carbamoyl-1H-indole-6-carboxylate (162 mg, 36.6% yield) as an off-white solid: $^1$H NMR (400 MHz, DMSO-d$_6$) δ ppm 3.80 (s, 3H) 6.62 (br. s., 2H) 7.04-7.18 (m, 2H) 7.53-7.63 (m, 2H) 7.72 (s, 1H) 10.80 (s, 1H); MS m/z 232.2 (M+H)$^+$; HPLC ca. 96%, RT=1.37 minutes.

A mixture of Intermediate 2C (0.100 g, 0.429 mmol), methyl 2-phenylacetate (0.302 mL, 2.14 mmol) and sodium methoxide 30% wt in MeOH (0.402 mL, 2.14 mmol) in methanol (1.0 mL) was placed in the microwave oven and heated to 140° C. for 30 minutes. After cooling, AcOH (0.125 mL, 2.19 mmol) was added and the resulting slurry was stirred at 20° C. for 1 hour. The solids were filtered, washed with MeOH (3×0.5 mL) and dried at 20° C. under high vacuum until constant weight to give Intermediate 2D (methyl 2-benzyl-4-hydroxy-9H-pyrimido[4,5-b]indole-7-carboxylate) (91 mg, 63.7% yield) as a tan solid; $^1$H NMR (400 MHz, DMSO-d$_6$) δ ppm 3.87 (s, 3H) 4.03 (s, 2H) 7.22-7.29 (m, 1H) 7.29-7.42 (m, 4H) 7.83 (dd, J=8.2, 1.6 Hz, 1H) 7.98-8.04 (m, 2H) 12.46 (br. s, 1H) 12.50 (br. s., 1H); MS m/z 334.2 (M+H)$^+$; HPLC 88.5% @ 220 nm and 86.3% @ 254 nm, RT=1.96 minutes.

A mixture of methyl 2-benzyl-4-hydroxy-9H-pyrimido[4,5-b]indole-7-carboxylate (0.685 g, 2.05 mmol) in POCl$_3$ (12.64 mL, 136 mmol) was heated to 90° C. for 16 hours. After cooling, the reaction mixture was concentrated to dryness. Suspended the resulting solid in sat. NaHCO$_3$ (50 mL) and EtOAc (75 mL). Stirred vigorously for 15 minutes then filtered the mixture. The layers were separated. The aqueous layer was extracted with EtOAc (2×50 mL). The combined organic layers were dried over anh. MgSO$_4$, filtered and concentrated to dryness to give methyl 2-benzyl-4-chloro-9H-pyrimido[4,5-b]indole-7-carboxylate (621 mg, 86% yield) as a tan solid; $^1$H NMR (400 MHz, DMSO-d$_6$) δ ppm 3.92 (s, 3H) 4.31 (s, 2H) 7.19-7.26 (m, 1H) 7.28-7.39 (m, 4H) 7.99 (dd, J=8.2, 1.2 Hz, 1H) 8.14 (d, J=1.2 Hz, 1H) 8.34 (d, J=8.2 Hz, 1H) 12.97 (s, 1H); MS m/z 352.2 (M+H)$^+$; HPLC 92%, RT=2.39 minutes.

To a solution of methyl 2-benzyl-4-chloro-9H-pyrimido [4,5-b]indole-7-carboxylate (0.050 g, 0.142 mmol) and 1-(3-((triisopropylsilyl)thio)propyl)piperidine (0.058 g, 0.185 mmol) in NMP (0.750 ml) was added tetrabutylammonium fluoride trihydrate (0.056 g, 0.178 mmol) and stirred at 20° C. for 6 hours. Additional 1-(3-((triisopropylsilyl)thio)propyl)piperidine (0.033 g, 0.104 mmol) and tetrabutylammonium fluoride trihydrate (0.029 g, 0.092 mmol) were added and continued stirring for 4 days. The reaction mixture was diluted with CH$_2$Cl$_2$ (25 mL). Washed with Water (3×7.5 mL). The organic layer was dried over anh. MgSO$_4$, filtered and concentrated to dryness. The residue was purified by flash chromatography to give the compound 6, methyl 2-benzyl-4-((3-(piperidin-1-yl)propyl)thio)-9H-pyrimido[4,5-b]indole-7-carboxylate (53 mg, 79% yield) as a tan solid; $^1$H NMR (400 MHz, DMSO-d$_6$) δ ppm 1.30-1.44 (m, 2H) 1.51 (br. s., 4H) 1.81-1.96 (m, 2H) 2.17-2.47 (m, 6H) 3.43 (t, J=7.2 Hz, 2H) 3.90 (s, 3H) 4.26 (s, 2H) 7.17-7.25 (m, 1H) 7.30 (t, J=7.6 Hz, 2H) 7.34-7.41 (m, 2H) 7.95 (dd, J=8.2, 1.6 Hz, 1H) 8.07-8.14 (m, 2H) 12.56 (s, 1H); HPLC 95.1% at 254 nm, RT 2.02 minutes; HRMS m/z 475.2155 (M+H)$^+$.

Compound 7

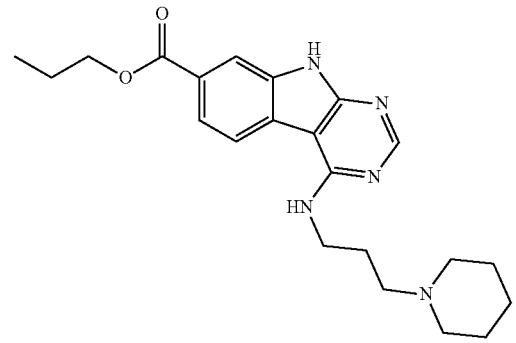 [SMILES: CCCOC(=O)c1ccc2c(c1)[nH]c1ncnc(NCCCN3CCCCC3)c12]

Ethyl 2-cyanoacetate (10.9 mL, 102 mmol) was slowly added to a suspension of sodium hydride 60% wt. in mineral oil (4.10 g, 102 mmol) in DMF (125 mL) at 0° C. The mixture was stirred at 0° C. for 15 minutes and methyl 4-fluoro-3-nitrobenzoate (10.2 g, 51 mmol) in DMF (125 mL) was added. The resulting deep red mixture was stirred at 0° C. for 30 minutes and then at room temperature for 3 hours. The reaction mixture was diluted with 1N HCl (40 mL) and EtOAc (40 mL). The separated aqueous layer was extracted with EtOAc (3×50 mL). The organic layers were combined and dried over anhydrous sodium sulfate, filtered and concentrated to afford a residue (26 g) which was purified by flash chromatography to give methyl 4-(1-cyano-2-ethoxy-2-oxoethyl)-3-nitrobenzoate (14.9 g, 100% yield); $^1$H NMR (400 MHz, DMSO-d$_6$) δ 1.19 (t, J=7.0 Hz, 3H) 3.93 (s, 3H) 4.23 (q, J=7.0 Hz, 2H) 6.38 (s, 1H)

7.87-7.99 (m, 1H) 8.42 (d, J=7.8 Hz, 1H) 8.64 (br. s., 1H); LCMS m/z 291.0 (M−H)⁻, HPLC>95%, RT 1.76 minutes.

To a solution of methyl 4-(1-cyano-2-ethoxy-2-oxoethyl)-3-nitrobenzoate (14.9 g, 51.0 mmol) in acetic acid (255 mL) was added zinc dust (16.7 g, 255 mmol) in portions over 35 minutes. The mixture was heated to 100° C. for 15 hours. The mixture was allowed to cool to room temperature, filtered through Celite and rinsed with ethyl acetate. Evaporation of the solvent gave a residue which was triturated in a mixture of dichloromethane and hexanes. The solids were filtered, washed with hexanes (3×15 mL) and dried at 20° C. under high vacuum until constant weight to give Intermediate 3A (3-ethyl 6-methyl 2-amino-1H-indole-3,6-dicarboxylate) (6.3 g, 47.1% yield) as a purple solid; $^1$H NMR (400 MHz, DMSO-d$_6$) δ ppm 1.32 (t, J=7.0 Hz, 3H) 3.81 (s, 3H) 4.24 (q, J=7.0 Hz, 2H) 6.99 (s, 2H) 7.55-7.64 (m, 2H) 7.74 (s, 1H) 10.84 (s, 1H); LCMS m/z 263.2 (M+H)⁺, HPLC 70%, RT 1.90 minutes.

A suspension of 3-ethyl 6-methyl 2-amino-1H-indole-3,6-dicarboxylate (1.1 g, 4.19 mmol), ammonium formate (0.53 g, 8.39 mmol) in formamide (16.7 mL, 419 mmol) was heated to 165° C. for 12 hours. The mixture was allowed to cool to room temperature and water was added. The resulting precipitate was filtered, air-dried and dried under high vacuum to give methyl 4-hydroxy-9H-pyrimido[4,5-b]indole-7-carboxylate (1.1 g, 108% yield) as a grey solid; $^1$H NMR (400 MHz, DMSO-d$_6$) δ ppm 3.89 (s, 3H) 7.86 (dd, J=8.2, 1.6 Hz, 1H) 8.05-8.08 (m, 2H) 8.21 (d, J=3.9 Hz, 1H) 12.36 (br. s., 1H) 12.51 (br. s, 1H); LCMS m/z 244.2 (M+H)⁺; HPLC 71%, RT 1.51 minutes.

A mixture of methyl 4-hydroxy-9H-pyrimido[4,5-b]indole-7-carboxylate (1.1 g, 4.5 mmol) and phosphorous oxychloride (15 mL, 161 mmol) was heated to 90° C. for 16 hours. The reaction mixture was cooled to room temperature and evaporated under reduced pressure. The residue was suspended in CH$_2$Cl$_2$ (20 mL) and filtered through Celite. The filtrate was concentrated to dryness to give methyl 4-chloro-9H-pyrimido[4,5-b]indole-7-carboxylate (360 mg, 30.4% yield) as an orange solid; $^1$H NMR (400 MHz, DMSO-d$_6$) δ ppm 3.93 (s, 3H) 8.02 (dd, J=8.20, 1.20 Hz, 1H) 8.19 (s, 1H) 8.40 (d, J=8.22 Hz, 1H) 8.86 (s, 1H) 13.07 (s, 1H); LCMS m/z 262.0 (M+H)+, HPLC 71%, RT 2.02 minutes.

A mixture of methyl 4-chloro-9H-pyrimido[4,5-b]indole-7-carboxylate (86 mg, 0.33 mmol), triethylamine (0.09 mL, 0.66 mmol) and 3-(piperidin-1-yl)propan-1-amine (0.078 mL, 0.49 mmol) in methanol (2 mL) was heated to 140° C. for 15 minutes in a microwave reactor. The mixture was allowed to cool to room temperature and evaporated under reduced pressure. The crude material purified by flash chromatography to give Intermediate 3B (methyl 4-((3-(piperidin-1-yl)propyl)amino)-9H-pyrimido[4,5-b]indole-7-carboxylate) (40 mg, 33.1% yield) as an off-white solid; $^1$H NMR (400 MHz, DMSO-d$_6$) δ ppm 1.38 (m, J=4.70 Hz, 2H) 1.49 (quin, J=5.48 Hz, 4H) 1.82 (quin, J=7.04 Hz, 2H) 2.21-2.45 (m, 6H) 3.64 (q, J=6.52 Hz, 2H) 3.89 (s, 3H) 7.42 (t, J=5.67 Hz, 1H) 7.84 (dd, J=8.20, 1.20 Hz, 1H) 8.04 (d, J=1.20 Hz, 1H) 8.38 (s, 1H) 8.41 (d, J=8.22 Hz, 1H) 12.15 (br. s., 1H); LCMS m/z 368.2 (M+H)⁺, HPLC 96.8% @ 254 nm; RT 1.38 minutes.

A mixture of methyl 4-((3-(piperidin-1-yl)propyl)amino)-9H-pyrimido[4,5-b]indole-7-carboxylate (40 mg, 0.109 mmol) and H$_2$SO$_4$ (87 μL, 1.633 mmol) in propanol (1 mL) was heated to 70° C. for 3 days. Concentrated to ca. 0.5 mL and diluted with EtOAc (10 mL) and water (10 mL). Neutralized to pH 7-8 with solid K$_2$CO$_3$ (ca. 100 mg). The layers were separated. The aqueous layer was extracted with EtOAc (10 mL). The combined organic layers were dried over anh. MgSO$_4$, filtered and concentrated to dryness to give compound 7, propyl 4-((3-(piperidin-1-yl)propyl)amino)-9H-pyrimido[4,5-b]indole-7-carboxylate (17 mg, 40% yield) as a white solid; $^1$H NMR (400 MHz, Methanol-d$_4$) δ ppm 8.36 (s, 1H), 8.24 (d, J=8.2 Hz, 1H), 8.19 (s, 1H), 7.97 (dd, J=8.2, 1.2 Hz, 1H), 4.33 (t, J=6.7 Hz, 2H), 3.74 (t, J=6.8 Hz, 2H), 2.41-2.59 (m, 6H), 1.93-2.05 (m, 2H), 1.78-1.92 (m, 2H), 1.56-1.68 (m, 4H), 1.49 (br. s., 2H), 1.08 (t, J=7.4 Hz, 3H); HPLC>95% at 254 nm, Rt 1.67 minutes; LCMS m/z 396.2 (M+H)⁺.

Compound 8

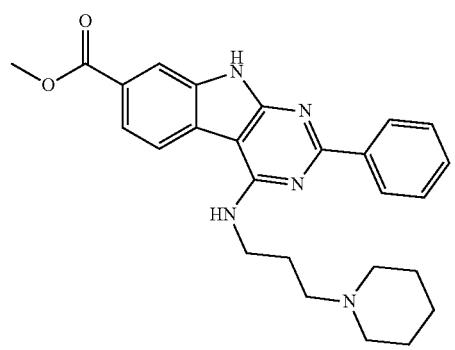 [SMILES: COC(=O)c1ccc2c(c1)[nH]c1nc(-c3ccccc3)nc(NCCCN3CCCCC3)c12]

A mixture of Intermediate 2C (80 mg, 0.343 mmol) and benzaldehyde (70 μL, 0.686 mmol) in acetic acid (1 mL) was heated to 110° C. for 22 hours. The reaction mixture was cooled to 20° C. and diluted with diethyl ether (10 mL). The solids were filtered, washed with Et$_2$O (3×1 mL), dried at 20° C. under high vacuum until constant weight to give Intermediate 4A, methyl 4-hydroxy-2-phenyl-9H-pyrimido[4,5-b]indole-7-carboxylate (47 mg, 42.9% yield) as a tan solid; $^1$H NMR (400 MHz, DMSO-d$_6$) δ ppm 3.89 (s, 3H) 7.53-7.65 (m, 3H) 7.87 (dd, J=8.22, 1.56 Hz, 1H) 8.06-8.12 (m, 2H) 8.18-8.24 (m, 2H) 12.55 (br. s., 2H); LCMS m/z 320.2 (M+H)⁺.

A mixture of methyl 4-hydroxy-2-phenyl-9H-pyrimido[4,5-b]indole-7-carboxylate (0.050 g, 0.157 mmol) in POCl$_3$ (1 mL, 10.73 mmol) was heated to 95° C. for 16 hours. After cooling, the reaction mixture was concentrated to dryness. Suspended the resulting solid in sat. NaHCO3 (10 mL) and stirred for 30 minutes. The solids were filtered, washed with Et$_2$O (3×1 mL), dried at 20° C. under high vacuum until constant weight to give methyl 4-chloro-2-phenyl-9H-pyrimido[4,5-b]indole-7-carboxylate (40 mg, 75% yield) as a tan solid; $^1$H NMR (400 MHz, DMSO-d$_6$) δ ppm 3.93 (s, 3H) 7.51-7.64 (m, 3H) 7.95-8.06 (m, 1H) 8.13-8.20 (m, 1H) 8.38 (d, J=8.22 Hz, 1H) 8.42-8.51 (m, 1H) 13.08 (s, 1H); MS m/z 338.2 (M+H)⁺; HPLC 99.2% @254 nm, RT=2.48 minutes.

A mixture of methyl 4-chloro-2-phenyl-9H-pyrimido[4,5-b]indole-7-carboxylate (0.043 g, 0.127 mmol), triethylamine (35 μL, 0.255 mmol) and 3-(piperidin-1-yl)propan-1-amine (32 μL, 0.191 mmol) in MeOH (0.6 ml) was heated 25 minutes to 140° C. in a microwave oven. Cooled to 20° C. and concentrated to dryness.

Purification on prep HPLC to give compound 8, methyl 2-phenyl-4-((3-(piperidin-1-yl)propyl)amino)-9H-pyrimido[4,5-b]indole-7-carboxylate 2,2,2-trifluoroacetate (32 mg, 45.0% yield) as a light yellow solid; $^1$H NMR (400 MHz, DMSO-d6) δ ppm 1.35 (br. s., 1H) 1.51-1.70 (m, 3H) 1.70-1.85 (m, 2H) 2.08-2.28 (m, 2H) 2.76-2.97 (m, 2H)

3.33-3.50 (m, 2H) 3.50-3.66 (m, 2H) 3.79-3.98 (m, 5H) 7.40-7.58 (m, 3H) 7.63 (br. s., 1H) 7.77-7.95 (m, 1H) 8.06 (br. s., 1H) 8.40-8.56 (m, 3H) 8.89-9.24 (m, 1H) 12.28 (br. s., 1H); HPLC 99.9% at 254 nm, Rt 1.82 minutes; HRMS m/z 444.2435 (M+H)$^+$.

The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for transducing a viral vector into cells, said method comprising contacting said cells with a compound of general formula I; and transducing said cells with a viral vector,

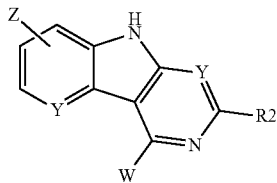

I or a salt thereof,
wherein:
each Y is independently selected from N and CH;
Z is
1) —CN
2) —C(O)OR1,
3) —C(O)N(R1)R3,
4) —C(O)R1, or
5) -heteroaryl optionally substituted with one or more RA or R4 substituents,
wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is
1) —CN,
2) —N(R1)R3,
3) —C(O)OR1,
4) —C(O)N(R1)R3,
5) —NR1C(O)R1,
6) —NR1C(O)OR1,
7) —OC(O)N(R1)R3,
8) —OC(O)R1,
9) —C(O)R1,
10) —NR1C(O)N(R1)R3,
11) —NR1S(O)$_2$R1,
12) -benzyl optionally substituted with 1, 2 or 3 RA or R1 substituents,
13) —X-L-(X-L)n-N(R1)R3,
14) —X-L-(X-L)n-heteroaryl optionally substituted with one or more RA or R4 substituents attached on either or both the L and heteroaryl groups,
15) —X-L-(X-L)n-heterocyclyl optionally substituted with one or more RA or R4 substituents attached on either or both the L and heterocyclyl groups,
16) —X-L-(X-L)n-aryl optionally substituted with one or more RA or R4 substituents,
17) —X-L-(X-L)$_n$-NR1RA or
18) —(N(R1)-L)$_n$-N$^+$R1R3R5 R6$^-$
wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from O, S, and NR1;
each L is independently
1) —C$_{1-6}$alkylene,
2) —C$_{2-6}$alkenylene,
3) —C$_{2-6}$alkynylene,
4) —C$_{3-7}$cycloalkylene, which optionally includes one or more other heteroatom selected from N, O and S or
5) —C3-7 cycloalkenylene, which optionally includes one or more other heteroatom selected from N, O and S
wherein the alkylene, the alkenylene, the alkynylene the cycloalkylene and the cycloalkenylene groups are each independently optionally substituted with one or two R4 or RA substituent;
R1 is each independently
1) —H,
2) —C$_{1-6}$alkyl,
3) —C$_{2-6}$ alkenyl,
4) —C$_{2-6}$alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl,
wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is
1) —H,
2) —C$_{1-6}$ alkyl, optionally substituted with one more RA substituents
3) —C(O)R4,
4) -L-heteroaryl optionally substituted with one or more RA or R4 substituents
5) -L-heterocyclyl optionally substituted with one or more RA or R4, or
6) -L-aryl optionally substituted with one or more RA or R4 substituents;
R3 is each independently
1) —H,
2) —C$_{1-6}$alkyl,
3) —C$_{2-6}$ alkenyl,
4) —C$_{2-6}$alkynyl,
5) —C$_{3-7}$cycloalkyl,
6) —C$_{3-7}$cycloalkenyl,
7) —C$_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently
1) —H,
2) —$C_{1-6}$alkyl,
3) —$C_{2-6}$ alkenyl,
4) —$C_{2-6}$alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl, or
11) -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently
1) —$C_{1-6}$alkyl,
2) —$C_{1-6}$ alkylene-$C_{2-6}$alkenyl which optionally includes one or more other heteroatom selected from N, O and S
3) —$C_{1-6}$ alkylene-$C_{2-6}$alkynyl which optionally includes one or more other heteroatom selected from N, O and S
4) -L-aryl which optionally includes one or more RA or R4 substituents
5) -L-heteroaryl which optionally includes one or more RA or R4 substituents
6) —$C_{1-6}$alkylene-C(O)O—
7) —$C_{1-6}$alkylene-C(O)OR1
8) —$C_{1-6}$alkylene-CN
9) —$C_{1-6}$ alkylene-C(O)NR1R3, wherein R1 and R3 optionally they join together with the nitrogen atom to form a 3 to 7-membered ring which optionally includes one or more other heteroatom selected from N, O and S; or
10) —$C_{1-6}$alkylene-OH;

R6 is
1) Halogen
2) OC(O)$CF_3$ or
3) OC(O)R1;

RA is each independently
1) -halogen,
2) —$CF_3$,
3) —OR1,
4) -L-OR1,
5) —$OCF_3$,
6) —SR1,
7) —CN,
8) —$NO_2$,
9) —NR1R3,
10) -L-NR1R1,
11) —C(O)OR1,
12) S(O)$_2$R4
13) —C(O)N(R1)R3,
14) —NR1C(O)R1,
15) —NR1C(O)OR1,
16) —OC(O)N(R1)R3,
17) —OC(O)R1,
18) —C(O)R4,
19) —NHC(O)N(R1)R3,
20) —NR1C(O)N(R1)R3, or
21) —$N_3$; and Rd is each independently
1) —H,
2) —$C_{1-6}$alkyl,
3) —$C_{2-6}$ alkenyl,
4) —$C_{2-6}$ alkynyl,
5) —$C_{3-7}$cycloalkyl,
6) —$C_{3-7}$cycloalkenyl,
7) —$C_{1-5}$ perfluorinated
8) -benzyl or
9) -heterocyclyl.

2. The method according to claim 1, wherein the compound is of formula IA

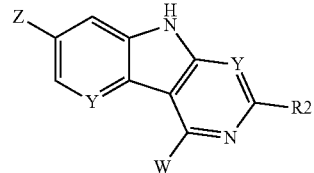

IA or a salt thereof,
wherein W, Y, Z and R2 are each as defined in claim 1.

3. The method according to claim 2, wherein
each Y is independently selected from N and CH;
Z is —CN, —C(O)OR1, —C(O)N(R1)R3, or -heteroaryl optionally substituted with one or more RA or R4 substituents,
W is —CN, —N(R1)R3, -benzyl optionally substituted with 1, 2 or 3 RA or R1 substituents, —X-L-(X-L)n-N(R1)R3, —X-L-(X-L)$_n$-NR1RA or —(N(R1)-L)$_n$-N$^+$R1R3R5R6$^-$
wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently O, S, or NR1,
L is each independently —$C_{1-6}$ alkylene, —$C_{2-6}$ alkenylene, —$C_{2-6}$ alkynylene, —C3-7 cycloalkylene, which optionally includes one or more other heteroatom selected from N, O and S or -C3-7 cycloalkenylene, which optionally includes one or more other heteroatom selected from N, O and S,
wherein the alkylene, the alkenylene, the alkynylene the cycloalkylene and the cycloalkenylene are each independently optionally substituted with one or two R4 or RA substituent;
R1 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -heteroaryl, or -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is —H, —$C_{1-6}$ alkyl, optionally substituted with one more RA substituents, —C(O)R4, -L-heteroaryl optionally substituted with one or more RA or R4 substituents, -L-heterocyclyl optionally substituted with one or more RA or R4, or -L-aryl optionally substituted with one or more RA or R4 substituents;

R3 is each independently —H, —C$_{1-6}$ alkyl, —C$_{2-6}$ alkenyl, —C$_{2-6}$ alkynyl, or —C$_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently —C$_{1-6}$ alkyl, -L-aryl which optionally includes one or more RA or R4 substituents, -L-heteroaryl which optionally includes one or more RA or R4 substituents, —C$_{1-6}$ alkylene-C(O)O—, —C$_{1-6}$ alkylene-C(O)OR1, —C$_{1-6}$ alkylene-CN, —C$_{1-6}$ alkylene-C(O)NR1R3, or —C$_{1-6}$ alkylene-OH;

R6 is Halogen, —OC(O)CF$_3$ or OC(O)R1;

RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$;

Rd is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -benzyl or -heterocyclyl.

4. The method according to claim 1, wherein the compound is of formula IIA:

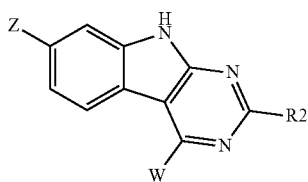

IIA or a salt prodrug thereof, wherein Z, W and R2 are each as defined in claim 1.

5. The method according to claim 4, wherein

Z is —CN, —C(O)O—C$_{1-6}$alkyl, —C(O)NH—C$_{1-6}$ alkyl, or -heteroaryl optionally substituted with one or more RA or R4 substituents, W is —N(R1)R3, —NR1-C$_{1-6}$ alkylene-N(R1)R3, —O—C$_{1-6}$ alkylene-N(R1)R3, —S—C$_{1-6}$ alkylene-N(R1)R3, —NR1-C$_{1-6}$ alkylene-NR1RA, —NR1-C$_{1-6}$ alkylene-(NR1-C$_{1-6}$ alkylene)$_n$-NR1R3 or —NR1-C$_{1-6}$ alkylene-(NR1-C$_{1-6}$ alkylene)$_n$-NR1RA;

wherein n is an integer equal to either 0, 1, 2, or 3 and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

R1 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is —H, —C$_{1-6}$ alkyl, —C(O)R4, —C$_{1-6}$ alkylene-heteroaryl optionally substituted with one or more RA or R4 substituents either on the alkylene or the heteroaryl, —C$_{1-6}$ alkylene-heterocyclyl optionally substituted with one or more RA or R4, or —C$_{1-6}$ alkylene-aryl optionally substituted with one or more RA or R4 substituents either on the alkylene or the heteroaryl;

R3 is each independently —H, —C$_{1-6}$ alkyl, —C$_{2-6}$ alkenyl, —C$_{2-6}$ alkynyl, or —C$_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$;

Rd is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -benzyl or -heterocyclyl.

6. The method according to claim 5, wherein:

Z is CO$_2$Me or 2-methyl-2H-tetrazol-5-yl;

R2 is benzyl, or H; and

W is NH-L-N(R1)R3 wherein L is C2-4 alkylene or C3-7 cycloalkylene and R1 and R3 is C1-4 alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

7. The method according to claim 6, wherein W is

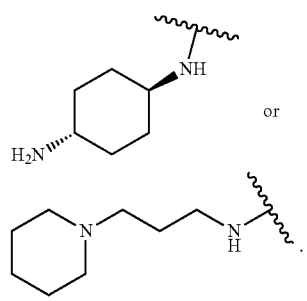

8. The method of claim 1, wherein the compound is of formula IIA

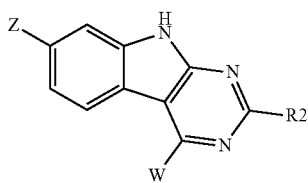

or a salt thereof,
wherein
Z is —C(O)O—$C_{1-4}$ alkyl, or -heteroaryl, preferably a 5-membered ring heteroaryl comprising 2-4 heteroatoms selected from N and O, optionally substituted with one or more RA or R4 substituents,
W is —N(R1)R3, —NR1-$C_{1-6}$ alkylene-N(R1)R3, —O—$C_{1-6}$ alkylene-N(R1)R3, —S—$C_{1-6}$ alkylene-N(R1)R3, or —NR1-$C_{1-6}$alkylene-(NR1-$C_{1-6}$alkylene)$_n$-NR1R3, wherein n is an integer equal to either 0, 1, 2, or 3 and wherein, when R1 and R3 are attached to the same nitrogen atom, optionally they join together with the nitrogen atom to form a 5 to 6-membered ring which optionally includes one or more other heteroatom selected from N and O, optionally the ring is substituted with one or more RA or R4;

R1 is each independently —H, —$C_{1-6}$ alkyl, —$C_{3-7}$ cycloalkyl, or -heterocyclyl,
wherein the alkyl, the cycloalkyl, the heterocyclyl are each independently optionally substituted with 1, 2 or 3 RA or Rd substituents;
R2 is —H, —$C_{1-6}$ alkyl, —$C_{1-6}$ alkylene-heteroaryl optionally substituted with one or more RA or R4 substituents either on the alkylene or the heteroaryl; or —$C_{1-6}$ alkylene-aryl optionally substituted with one or more RA or R4 substituents either on the alkylene or the aryl;
R3 is each independently —H, —$C_{1-6}$ alkyl, wherein the alkyl group is optionally substituted with 1, 2 or 3 RA or Rd substituents;
R4 is each independently H, —$C_{1-6}$ alkyl, wherein the alkyl is optionally substituted with 1, 2 or 3 RA or Rd substituents;
RA is each independently -halogen, —$CF_3$, —OR1, —$OCF_3$, —SR1, —CN, —$NO_2$, —NR1R3, —C(O)OR1, $S(O)_2$R4, —C(O)N(R1)R3, —NR1C(O)R1, —NR1C(O)OR1, —OC(O)N(R1)R3, —OC(O)R1, —C(O)R4, —NHC(O)N(R1)R3, or —NR1C(O)N(R1)R3, and
Rd is each independently —H, or —$C_{1-6}$ alkyl.
9. The method of claim 1, wherein said compound is

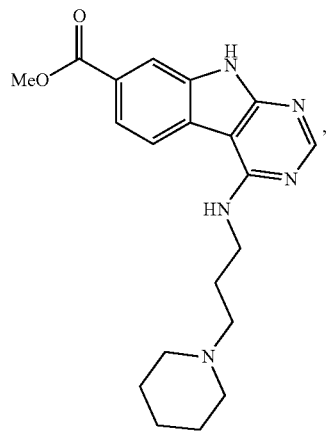

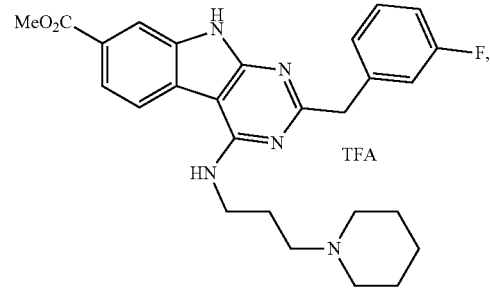

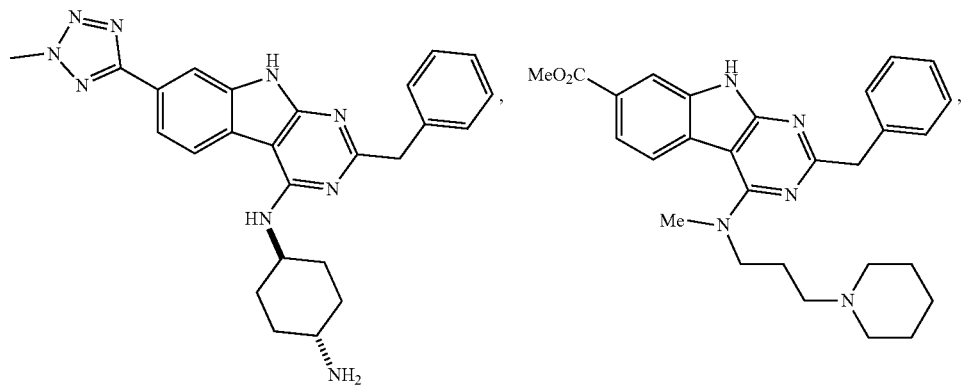

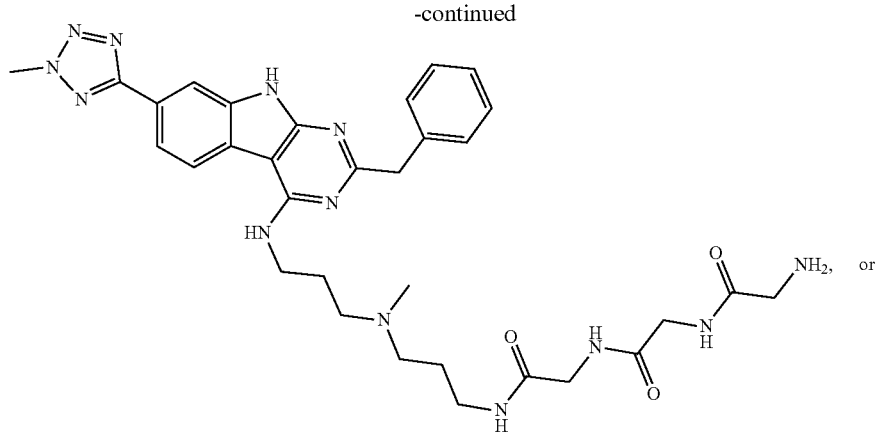

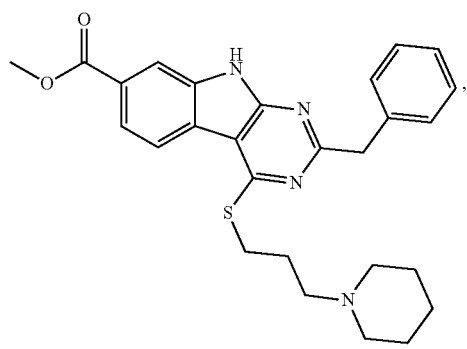

or a salt thereof.

10. The method of claim 1, wherein said cells comprise stem cells and/or progenitor cells.

11. The method of claim 10, wherein said cells are derived from cord blood, bone marrow or peripheral blood.

12. The method of claim 1, wherein said viral vector is an integration defective viral vector.

13. The method of claim 12, wherein said viral vector is a lentiviral vector.

14. The method of claim 13, wherein the lentiviral vector is pseudotyped with a vesicular stomatitis virus G-protein (VSV-G) or a RAD114 envelope protein.

15. The method of claim 10, wherein said cells are contacted with said compound prior to said transducing.

16. The method of claim 10, wherein said cells are contacted with said compound prior to and during said transducing.

17. A population of transduced cells obtained by the method of claim 1.

18. A method of treating a subject in need of a treatment with cell gene therapy, said method comprising administering to said subject an effective amount of the population of transduced cells of claim 17.

19. The method of claim 18, wherein said subject suffers from a hematologic or lysosomal storage disease selected from Wiskott-Aldrich syndrome (WAS), metachromatic leukodystrophy (MLD), Leukocyte adherence deficiency, X-linked CGD, Fanconi anemia, adrenoleukodystrophy, Mucopolysaccharidosis IIIA, severe combined immunodeficiency (SCID) and adenosine deaminase (ADA) deficiency.

20. The method of claim 9, wherein said compound is

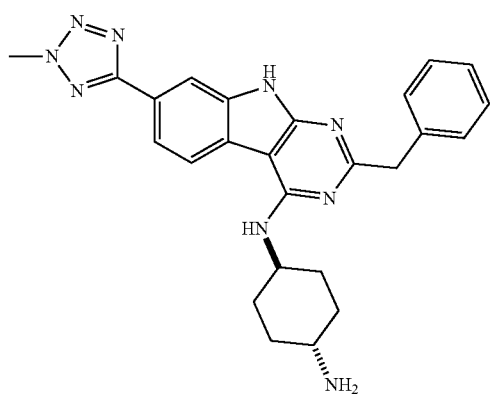

21. The population of transduced cells of claim 17, wherein said compound is
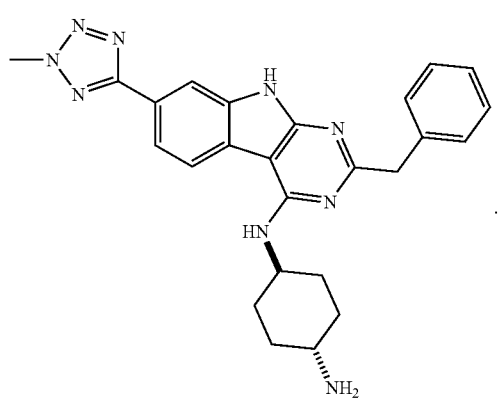
22. The method of claim 18, wherein said compound is
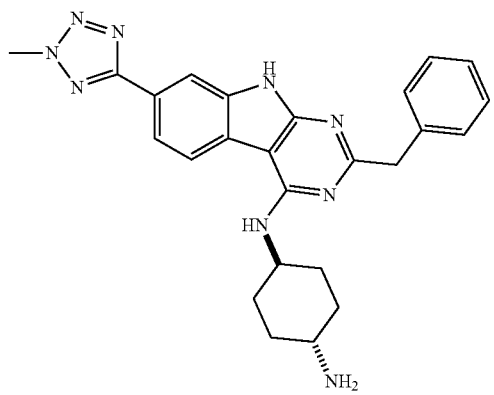
* * * * *